US009724404B2

(12) United States Patent
Coursaget et al.

(10) Patent No.: US 9,724,404 B2
(45) Date of Patent: Aug. 8, 2017

(54) HPV PARTICLES AND USES THEREOF

(75) Inventors: Pierre L. Coursaget, Paris (FR); Antoine A. Touzé, Tours (FR); Maxime J. J. Fleury, Tours (FR); Nicolas Combelas, Tours (FR); Elisabet de los Pinos, Brookline, MA (US)

(73) Assignees: INSERM (Institut National de la Santé et de la Recherche Médicale), Paris (FR); Aura Biosciences, Inc., Cambridge, MA (US)

( * ) Notice: Subject to any disclaimer, the term of this patent is extended or adjusted under 35 U.S.C. 154(b) by 272 days.

(21) Appl. No.: 13/264,213

(22) PCT Filed: Jul. 24, 2009

(86) PCT No.: PCT/US2009/004299
§ 371 (c)(1),
(2), (4) Date: Mar. 2, 2012

(87) PCT Pub. No.: WO2010/120266
PCT Pub. Date: Oct. 21, 2010

(65) Prior Publication Data
US 2012/0171290 A1 Jul. 5, 2012

Related U.S. Application Data

(60) Provisional application No. 61/168,914, filed on Apr. 13, 2009.

(51) Int. Cl.
| | | |
|---|---|---|
| *A01N 63/00* | (2006.01) | |
| *A61K 39/00* | (2006.01) | |
| *A61K 39/12* | (2006.01) | |
| *C07K 14/005* | (2006.01) | |
| *C07K 16/08* | (2006.01) | |
| *C12N 7/00* | (2006.01) | |
| *C12N 15/11* | (2006.01) | |
| *C12N 15/88* | (2006.01) | |

(52) U.S. Cl.
CPC .......... *A61K 39/12* (2013.01); *A61K 39/0011* (2013.01); *C07K 14/005* (2013.01); *C07K 16/084* (2013.01); *C12N 7/00* (2013.01); *C12N 15/111* (2013.01); *C12N 15/88* (2013.01); *A61K 2039/5258* (2013.01); *C07K 2317/34* (2013.01); *C12N 2310/11* (2013.01); *C12N 2310/14* (2013.01); *C12N 2320/32* (2013.01); *C12N 2710/14143* (2013.01); *C12N 2710/20022* (2013.01); *C12N 2710/20023* (2013.01); *C12N 2710/20034* (2013.01); *C12N 2800/22* (2013.01)

(58) Field of Classification Search
CPC .... C07K 16/084; C07K 14/005; C12N 15/88; C12N 15/111; C12N 7/00; A61K 39/0011; A61K 39/12; A61K 39/001
USPC ....................................................... 424/93.1
See application file for complete search history.

(56) References Cited

U.S. PATENT DOCUMENTS

| | | | |
|---|---|---|---|
| 4,625,014 A | 11/1986 | Senter et al. | |
| 4,659,839 A | 4/1987 | Nicolotti | |
| 5,334,711 A | 8/1994 | Sproat | |
| 5,716,824 A | 2/1998 | Beigelman | |
| 6,022,522 A | 2/2000 | Sweet et al. | |
| 6,180,389 B1 | 1/2001 | Douglas et al. | |
| 6,416,945 B1 | 7/2002 | McCarthy et al. | |
| 6,599,739 B1 | 7/2003 | Lowy et al. | |
| 6,984,386 B2 | 1/2006 | Douglas et al. | |
| 6,991,795 B1 | 1/2006 | Lowe et al. | |
| 7,205,126 B2 | 4/2007 | Qiao et al. | |
| 7,351,533 B2 * | 4/2008 | McCarthy .......... | A61K 47/4833 435/235.1 |
| 7,951,379 B2 | 5/2011 | Kuroda et al. | |
| 8,394,411 B2 | 3/2013 | Roberts et al. | |
| 2003/0206887 A1 | 11/2003 | Morrissey et al. | |
| 2004/0005338 A1 * | 1/2004 | Bachmann et al. ....... | 424/204.1 |
| 2004/0028694 A1 | 2/2004 | Young et al. | |
| 2004/0115132 A1 | 6/2004 | Young et al. | |
| 2004/0121465 A1 | 6/2004 | Robinson | |
| 2004/0146531 A1 * | 7/2004 | Antonsson et al. ....... | 424/204.1 |
| 2004/0152181 A1 | 8/2004 | McCarthy et al. | |
| 2005/0118191 A1 | 6/2005 | Robinson et al. | |
| 2005/0181064 A1 | 8/2005 | Kuroda | |
| 2006/0088536 A1 | 4/2006 | Kuroda | |
| 2006/0141042 A1 | 6/2006 | Kuroda | |
| 2006/0166913 A1 | 7/2006 | Suzuki | |
| 2006/0204444 A1 | 9/2006 | Young et al. | |

(Continued)

FOREIGN PATENT DOCUMENTS

| | | |
|---|---|---|
| CN | 1904012 A | 1/2007 |
| EP | 1491210 A1 | 12/2004 |

(Continued)

OTHER PUBLICATIONS

Varsani et al., 2003, J. Virol. 77:8386-8393.*
Xu et al., 2006, Arch. Virol. 151:2133-2148.*
Wang et al 2003, J. General Virology 84:1493-1497.*
Carter-b et al 2006, J. Virol. 80:4664-4672).*
Sadeyen et al 2003, Virol. 309:32-40.*
International Preliminary Report on Patentability for PCT/IB2010/002654 mailed Apr. 12, 2012.

(Continued)

*Primary Examiner* — Christopher M Babic
*Assistant Examiner* — Kelaginamane T Hiriyanna
(74) *Attorney, Agent, or Firm* — Wolf, Greenfield & Sacks, P.C.

(57) ABSTRACT

The invention relates to modified HPV particles that can be used therapeutically. Modified HPV particles may be used to deliver therapeutic agents, including siRNA molecules. Modified HPV particles may be used for the treatment of diseases or conditions of mucosal tissue, including HPV (human papilloma virus) infection and HPV-related tumors.

13 Claims, 19 Drawing Sheets

(56) References Cited

U.S. PATENT DOCUMENTS

Figure 1:
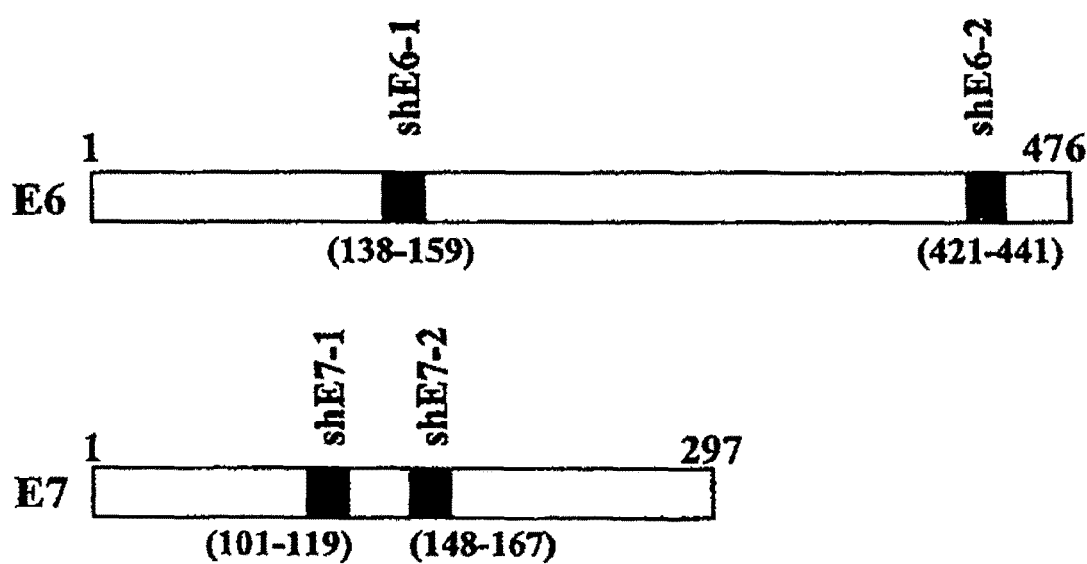

| | | |
|---|---|---|
| 2006/0269954 A1 | 11/2006 | Lowy et al. |
| 2007/0059245 A1 | 3/2007 | Young et al. |
| 2007/0059746 A1 | 3/2007 | Kuroda |
| 2007/0258889 A1 | 11/2007 | Douglas et al. |
| 2009/0012022 A1 | 1/2009 | Milner et al. |
| 2009/0041671 A1 | 2/2009 | Young et al. |
| 2010/0135902 A1 | 6/2010 | Roberts et al. |
| 2011/0052496 A1 | 3/2011 | Cid-Arregui |
| 2012/0015899 A1 | 1/2012 | Lomonossoff et al. |
| 2012/0171290 A1 | 7/2012 | Coursaget et al. |
| 2013/0115247 A1 | 5/2013 | de los Pinos et al. |
| 2013/0116408 A1 | 5/2013 | de los Pinos |
| 2014/0377170 A1 | 12/2014 | de los Pinos et al. |
| 2016/0228568 A1 | 8/2016 | de los Pinos et al. |

FOREIGN PATENT DOCUMENTS

| | | |
|---|---|---|
| JP | 2007-065646 A | 3/2007 |
| WO | WO 91/03162 A1 | 3/1991 |
| WO | WO 92/07065 A1 | 4/1992 |
| WO | WO 93/15187 A1 | 8/1993 |
| WO | WO 97/26270 A2 | 7/1997 |
| WO | WO 99/15630 A1 | 4/1999 |
| WO | WO 00/09673 A1 | 2/2000 |
| WO | WO 03/008573 A2 | 1/2003 |
| WO | WO 2005/051431 A1 | 6/2005 |
| WO | WO 2005/086667 A2 | 9/2005 |
| WO | WO 2006/125997 A1 | 11/2006 |
| WO | WO 2008/048288 A2 | 4/2008 |
| WO | WO 2008/054184 A1 | 5/2008 |
| WO | WO 2008/103920 A2 | 8/2008 |
| WO | WO 2010/120266 A1 | 10/2010 |
| WO | WO 2011/039646 A2 | 4/2011 |
| WO | WO 2013/080187 A1 | 6/2013 |
| WO | WO 2013/119877 A1 | 8/2013 |

OTHER PUBLICATIONS

Carter et al., Identification of a human papillomavirus type 16-specific epitope on the C-terminal arm of the major capsid protein L1. J Virol. Nov. 2003;77(21):11625-32.

Kawana et al., In vitro construction of pseudovirions of human papillomavirus type 16: incorporation of plasmid DNA into reassembled L1/L2 capsids. J Virol. Dec. 1998;72(12):10298-300.

U.S. Appl. No. 13/125,482, filed Sep. 12, 2011, George Lomonossoff et al.

U.S. Appl. No. 13/302,390, filed Nov. 22, 2011, Johannes Fruehauf et al.

PCT/IB2010/002654, mailed Aug. 18, 2011, International Search Report and Written Opinion.

PCT/IB2010/002654, mailed Apr. 8, 2011, Invitation to Pay Additional Fees.

PCT/US2009/004299, mailed Oct. 27, 2011, International Preliminary Report on Patentability.

PCT/US2009/004299, mailed Sep. 24, 2010, International Search Report and Written Opinion.

PCT/US2009/005808, mailed Mar. 5, 2010, International Search Report and Written Opinion.

PCT/US2009/005808, mailed May 5, 2011, International Preliminary Report on Patentability.

[No Author Listed] Bac-to-Bac Baculovirus Expresion System. An efficient site-specific transposition system to generate baculovirus for high-level expression of recombinant proteins. Sep. 4, 2010. Retrieved from the Internet on Sep. 23, 2013. 80 pages.

Carpentier et al. Mutations on the FG surface loop of human papillomavirus type 16 major capsid protein affect recognition by both type-specific neutralizing antibodies and cross-reactive antibodies. J Med Virol. Dec. 2005;77(4):558-65. Abstract only.

Christensen et al. Surface conformational and linear epitopes on HPV-16 and HPV-18 L1 virus-like particles as defined by monoclonal antibodies. Virology. Sep. 1, 1996;223(1):174-84.

Ewers et al., GM1 structure determines SV40-induced membrane invagination and infection. Nat Cell Biol. Jan. 2010;12(1):11-20; sup pp. 1-12. doi: 10.1038/ncb1999. Epub Dec. 20, 2009.

Finnen et al., Interactions between papillomavirus L1 and L2 capsid proteins. J Virol. Apr. 2003;77(8):4818-26.

Hagensee et al. Self-assembly of human papillomavirus type 1 capsids by expression of the L1 protein alone or by coexpression of the L1 and L2 capsid proteins. Journal of virology. Jan. 1, 1993;67(1):315-22.

Kirnbauer et al. Efficient self-assembly of human papillomavirus type 16 L1 and L1-L2 into virus-like particles. Journal of virology. Dec. 1, 1993;67(12):6929-36.

Kirnbauer et al. Papillomavirus L1 major capsid protein self-assembles into virus-like particles that are highly immunogenic. Proceedings of the National Academy of Sciences. Dec. 15, 1992;89(24):12180-4.

Leong et al., Intravital imaging of embryonic and tumor neovasculature using viral nanoparticles. Nat Protoc. Aug. 2010;5(8):1406-17. doi: 10.1038/nprot.2010.103. Epub Jul. 8, 2010.

Li et al, Expression of the human papillomavirus type 11 L1 capsid protein in *Escherichia coli*: characterization of protein domains involved in DNA binding and capsid assembly. J Virol. Apr. 1997;71(4):2988-95.

Li et al, Trackable and Targeted Phage as Positron Emission Tomography (PET) Agent for Cancer Imaging. Theranostics. 2011;1:371-80. Epub Nov. 18, 2011.

Oh et al., Enhanced mucosal and systemic immunogenicity of human papillomavirus-like particles encapsidating interleukin-2 gene adjuvant. Virology. Oct. 25, 2004;328(2):266-73.

Pedersen et al. Immunization of early adolescent females with human papillomavirus type 16 and 18 L1 virus-like particle vaccine containing AS04 adjuvant. Journal of Adolescent Health. Jun. 30, 2007;40(6):564-71.

Pinto et al. Cellular immune responses to human papillomavirus (HPV)-16 L1 in healthy volunteers immunized with recombinant HPV-16 L1 virus-like particles. Journal of Infectious Diseases. Jul. 15, 2003;188(2):327-38.

Raja et al., Hybrid virus-polymer materials. 1. Synthesis and properties of PEG-decorated cowpea mosaic virus. Biomacromolecules. May-Jun. 2003;4(3):472-6.

Rose et al. Expression of human papillomavirus type 11 L1 protein in insect cells: in vivo and in vitro assembly of viruslike particles. Journal of Virology. Apr. 1, 1993:67(4):1936-44.

Wang et al., Expression of Human Papillomavirus Type 6 L1 and L2 Isolated in China and Self Assembly of Virus-like Particles by the Products. Acta Biochimica et Biophysica Sinica. 2003; 35(1):27-34. 10 pages.

Zhang et al. Expression of Human Papillomavirus Type 16 L1 Protein in *Escherichia coli*: Denaturation, Renaturation, and Self-Assembly of Virus-like Particles in Vitro. Virology. Apr. 10, 1998;243(2):423-31.

Zhou et al. Expression of vaccinia recombinant HPV 16 L1 and L2 ORF proteins in epithelial cells is sufficient for assembly of HPV virion-like particles. Virology. Nov. 1, 1991;185(1):251-7.

U.S. Appl. No. 14/376,408, filed Aug. 1, 2014.

U.S. Appl. No. 15/023,169, filed Mar. 18, 2016.

PCT/US2013/025230, mailed Jun. 5, 2013, International Search Report and Written Opinion.

PCT/US2013/025230, mailed Aug. 21, 2014, International Preliminary Report on Patentability.

PCT/US2012/063603, mailed Feb. 22, 2013, International Search Report and Written Opinion.

PCT/US2012/063603, mailed May 14, 2015, International Preliminary Report on Patentability.

PCT/US2014/056412, mailed Dec. 29, 2014, International Search Report and Written Opinion.

PCT/US2014/056412, mailed Mar. 31, 2016, International Preliminary Report on Patentability.

Alvarez, Insertion de sequences peptidiques dans la proteine majeure de capside du papillomavirus de type 16: application au ciblage pulmonaire de vecteurs derives et a la production d'un vaccine chimerique. Thesis. Universite Francois Rabelais. Jun. 20, 2006. 203 pages.

(56) References Cited

OTHER PUBLICATIONS

Bergsdorf et al., Highly efficient transport of carboxyfluorescein diacetate succinimidyl ester into COS7 cells using human papillomavirus-like particles. FEBS Lett. Feb. 11, 2003;536(1-3):120-4.
Bousarghin et al., Inhibition of cervical cancer cell growth by human papillomavirus virus-like particles packaged with human papillomavirus oncoprotein short hairpin RNAs. Mol Cancer Ther. Feb. 2009;8(2):357-65. Epub Jan. 27, 2009.
Brumfield et al., Heterologous expression of the modified coat protein of Cowpea chlorotic mottle brotnovirus results in the assembly of protein cages with altered architectures and function. J Gen Virol. Apr. 2004;85(Pt 4):1049-53.
Buck et al., Efficient intracellular assembly of papillomaviral vectors. J Virol. Jan. 2004;78(2):751-7.
Buck et al., Production of papillomavirus-based gene transfer vectors. Current Protocols in Cell Biology. 26.1.1-26.1.19, Dec. 2007.
Butz et al., siRNA targeting of the viral E6 oncogene efficiently kills human papillomavirus-positive cancer cells. Oncogene. Sep. 4, 2003;22(38):5938-45.
Carpentier et al., Cell targeting for CF gene therapy: Identification of a new specific cell ligand and selection of infectious papillomavirus mutants. J Cystic Fibro. Jun. 1, 2009;8:S31.
Carpentier, Retargeting human papillomavirus-mediated gene transfer to human airway epithelial cells. J Cystic Fibro. Jun. 1, 2010;9:S17.
Combita et al., Gene transfer using human papillomavirus pseudovirions varies according to virus genotype and requires cell surface heparan sulfate. FEMS Microbiol Lett. Oct. 16, 2001;204(1):183-8.
Cook et al., Purification of virus-like particles of recombinant human papillomavirus type 11 major capsid protein L1 from *Saccharomyces cerevisiae*. Protein Expr Purif. Dec. 1999;17(3):477-84.
Douglas et al., Protein engineering of a viral cage for constrained nanomaterials synthesis. Adv Mater. Mar. 12, 2002;14(6):415-8.
Elbashir et al., Analysis of gene function in somatic mammalian cells using small interfering RNAs. Methods. Feb. 2002;26(2):199-213.
Fleury et al., Identification of neutralizing conformational epitopes on the human papillomavirus type 31 major capsid protein and functional implications. Protein Sci. Jul. 2009;18(7):1425-38.
Gaden et al., Gene transduction and cell entry pathway of fiber-modified adenovirus type 5 vectors carrying novel endocytic peptide ligands selected on human tracheal glandular cells. J Virol. Jul. 2004;78(13):7227-47.
Gillitzer et al., Controlled ligand display on a symmetrical protein-cage architecture through mixed assembly. Small. Aug. 2006;2(8-9):962-6.
Jiang et al., Gel-based application of siRNA to human epithelial cancer cells induces RNAi-dependent apoptosis. Oligonucleotides. 2004 Winter; 14(4):239-48.
Jiang et al., Selective silencing of viral gene E6 and E7 expression in HPV-positive human cervical carcinoma cells using small interfering RNAs. Methods Mol Biol. 2005;292:401-20.
Jiang et al., Selective silencing of viral gene expression in HPV-positive human cervical carcinoma cells treated with siRNA, a primer of RNA interference. Oncogene. Sep. 5, 2002;21(39):6041-8.
Jost et al., A novel peptide, THALWHT, for the targeting of human airway epithelia. FEBS Lett. Feb. 2, 2001;489(2-3):263-9.
Lavelle et al., The disassembly, reassembly and stability of CCMV protein capsids. J Virol Methods. Dec. 2007;146(1-2):311-6. Epub Sep. 4, 2007.
Lee et al., Adaptations of nanoscale viruses and other protein cages for medical applications. Nanomedicine. Sep. 2006;2(3):137-49.
Pyeon et al., Production of infectious human papillomavirus independently of viral replication and epithelial cell differentiation. Proc Natl Acad Sci U S A. Jun. 28, 2005;102(26):9311-6. Epub Jun. 15, 2005.
Ryding et al., Deletion of a major neutralizing epitope of human papillomavirus type 16 virus-like particles. J Gen Virol. Mar. 2007;88(Pt 3):792-802.
Sadeyen et al., Insertion of a foreign sequence on capsid surface loops of human papillomavirus type 16 virus-like particles reduces their capacity to induce neutralizing antibodies and delineates a conformational neutralizing epitope. Virology. Apr. 25, 2003;309(1):32-40.
Schädlich et al., Refining HPV 16 L1 purification from *E. coli*: reducing endotoxin contaminations and their impact on immunogenicity. Vaccine. Mar. 4, 2009;27(10):1511-22. Epub Jan. 25, 2009.
Speir et al., Structures of the native and swollen forms of cowpea chlorotic mottle virus determined by X-ray crystallography and cryo-electron microscopy. Structure. Jan. 15, 1995;3(1):63-78.
Touze et al., In vitro gene transfer using human papillomavirus-like particles. Nucleic Acids Res. Mar. 1, 1998;26(5):1317-23.
Touze et al., The L1 major capsid protein of human papillomavirus type 16 variants affects yield of virus-like particles produced in an insect cell expression system. J Clin Microbiol. Jul. 1998;36(7):2046-51.
Touzé et al., The nine C-terminal amino acids of the major capsid protein of the human papillomavirus type 16 are essential for DNA binding and gene transfer capacity. FEMS Microbiol Lett. Aug. 1, 2000;189(1):121-7.
Uchida et al., Biological Containers: Protein Cages as Multifunctional Nanoplatforms. Adv Mater. 2007;19:1025-42.
Vaysse et al., Improved transfection using epithelial cell line-selected ligands and fusogenic peptides. Biochim Biophys Acta. Jul. 26, 2000;1475(3):369-76.
Wang et al., Insertion of a targeting peptide on capsid surface loops of human papillomavirus type-16 virus-like particles mediate elimination of anti-dsDNA Abs-producing B cells with high efficiency. J Immunother. Jan. 2009;32(1):36-41.
White et al., Genetic modification of adeno-associated viral vector type 2 capsid enhances gene transfer efficiency in polarized human airway epithelial cells. Hum Gene Ther. Dec. 2008;19(12):1407-14.
Willits et al., Effects of the cowpea chlorotic mottle bromovirus beta-hexamer structure on virion assembly. Virology. Feb. 15, 2003;306(2):280-8.
Yoshinouchi et al., In vitro and in vivo growth suppression of human papillomavirus 16-positive cervical cancer cells by E6 siRNA. Mol Ther. Nov. 2003;8(5):762-8.

\* cited by examiner

A

B

A

E7-1 shRNA HPV pseudovirions

VLPs alone

Figure 8

```
                        263-DPASRE (HBc)-264 (SEQ ID NO: 65)
HPV31L1-HBc    257-FVRHFFNRSGTVGESVPTDLYIKGSGSTATLANSTYFPT-295 (SEQ ID NO: 2
H31.D24                                   DLYIK (SEQ ID NO: 46)
H31.F7                  RHFFNRSGTV (SEQ ID NO: 45)
H31.B1                       RSGTVGESV (SEQ ID NO: 50)
H31.F16                       SGTVGESVP (SEQ ID NO: 48)
H31.H12                      RSGTVG (SEQ ID NO: 49)
```

Figure 13

```
16  256-FVRHLFNRAGAVGENVPDDLYIKGSGSTANLASSNYFPT-294 (SEQ ID NO: 1)
X        ------------------T------------T--N------
Y        ----F---S-T---S--T------------T--N------
31  257-FVRHFFNRSGTVGESVPTDLYIKGSGSTATLANSTYFPT-295 (SEQ ID NO: 2)
```

Figure 15

Antibody titers observed in immunized mice (GMT)

| ELISA with HPV | Mice immunized with HPV | | | |
|---|---|---|---|---|
| | 16 | 31 | X | Y |
| 16 | 2,016 | 11 | 28 | 32 |
| 31 | 13 | 1,903 | <10 | <10 |
| X | 18 | <10 | 1,838 | 538 |
| Y | 36 | <10 | 857 | 2,111 |

A

B

HPV PARTICLES AND USES THEREOF

RELATED APPLICATIONS

This application is a 35 U.S.C. §371 National Phase Application of International Application No. PCT/US2009/004299, filed Jul. 24, 2009, which claims priority from U.S. Provisional Patent Application No. 61/168,914, filed Apr. 13, 2009, the contents of both of which are incorporated herein by reference.

FIELD OF THE INVENTION

The invention relates to human papillomavirus like particles (VLPs) and their use as therapeutic agents.

BACKGROUND OF THE INVENTION

Cervical cancer is one of the leading causes of cancer deaths in women world-wide, killing more than 233,000 women each year. Cervical cancer was the most common malignancy in both incidence and mortality among women prior to the 20th century. The reduction in the incidence of cervical cancer is one of the major public health achievements in developed nations, largely due to the implementation of population-based screening, detection and treatment programs for pre-invasive disease. However, while the incidence of cervical cancer in developed nations has fallen, the disease continues to be the second most common cancer in women worldwide.

Papanicolaou (Pap) smears can detect cervical cancer or pre-cancerous changes in the cervix, many of which are related to HPV. These Pap smears have greatly reduced the incidence and mortality of cervical cancer in developed countries where widespread screening procedures occur. In developing countries where screening procedures are still limited, cervical cancer is the most frequently reported cancer in women, and the incidence continues to rise.

All current treatments for cervical intraepithelial abnormalities, including cryotherapy, laser ablation, excisional conization and loop electrosurgical excision procedure (LEEP), are invasive surgical procedures that often lead to significant side effects including excessive discharge, infection, bleeding, cramping, and cervical incompetence, which may lead to miscarriage, loss of cervical integrity and inability to become pregnant. In addition, these procedures must be performed in an outpatient facility, increasing the cost of treatment.

Cervical intraepithelial neoplasia (CIN) refers to a pre-invasive pathological intermediate to cervical cancer. The abnormalities observed on a cytologic smear or tissue biopsy of the cervix represent alterations in the degree of differentiation of cervical epithelial cells. This cellular dysplasia is categorized into three different groups of severity: CIN I refers to mild dysplasia confined to the basal third of the epithelium; CIN II refers to lesions confined to the basal two-thirds of the epithelium; and CIN III refers to cellular dysplasia encompassing greater than two-thirds of the epithelial thickness.

Approximately 3.5 million women in the United States will have abnormal Pap smear tests each year. Approximately 1.2 million of these women have a squamous intra-epithelial lesion (SIL) of which 200,000 to 300,000 are classified as high-grade. The incidence of high-grade CIN in Latin America is more than 3 times that seen in the US. Table 1 provides a summary of the prevalence of HPV infections and CIN worldwide.

TABLE 1

Worldwide Prevalence of HPV and CIN

|  | Incidence High-Risk HPV | Incidence CIN 2/3 |
| --- | --- | --- |
| US | 1,750,000 | 250,000 |
| Europe | 1,839,200 | 275,880 |
| Latin America | 5,884,110 | 882,616 |
| Japan | 1,173,480 | 176,022 |

HPV infection is endemic among sexually active individuals. Women who have multiple sexual partners have a higher chance of acquiring HPV and consequently, an HPV-related cervical infection. Infection with high-risk HPV types increases the odds that a woman will develop cervical cancer. Screening for and subsequently treating pre-cancerous cervical conditions is highly effective in the prevention of cervical cancer in HPV-infected women. However, current treatments often require surgical intervention and alternative therapeutic options are needed.

SUMMARY OF INVENTION

Aspects of the invention relate to HPV-based particles and uses thereof for treating diseases and/or delivering therapeutic agents. In some embodiments, compositions and methods of the invention are useful for treating mucosal conditions (e.g., diseases and/or infections of mucosal tissue, for example of mucosal epithelial cells).

In some embodiments, aspects of the invention relate to modified HPV-based particles that can deliver a therapeutic agent to mucosal tissue (e.g., topically). In some embodiments, the therapeutic agent can be an antiviral agent. The antiviral agent may be used to treat a viral infection by, for example, a human papilloma virus, a Herpes virus, or other virus that targets mucosal tissue. In some embodiments, the therapeutic agent can be an anticancer agent. The anticancer agent may be used to treat, for example, cervical cancer or any other cancer of a mucosal tissue. In some embodiments, the invention provides methods for treating human papilloma virus (HPV) infection and methods for treating HPV-associated diseases including, but not limited to, cervical cancer in a subject. However, it should be appreciated that modified viral particles of the invention may be used to deliver other types of therapeutic and/or medical agents (e.g., imaging or contrast agents).

In some embodiments, particles of the invention may be delivered topically (e.g., in the form of a cream, foam, spray, aerosol, or other formulation suitable for topical delivery) to any mucosal tissue (e.g., to cervical, nasal, oral, or other mucosal tissue). However, aspects of the invention are not limited to topical delivery and modified particles may be delivered subcutaneously, intravenously, parenterally, and/or via any other suitable delivery route.

Methods provided herein comprise administering to the subject one or more therapeutic agents delivered by a virus-like particle (VLP)-based delivery system. In certain embodiments, the VLP-based delivery system comprises human papilloma virus (HPV)-like nanoparticles. In some embodiments, HPV nanoparticles comprise viral L1 protein. In some embodiments, HPV nanoparticles comprise viral L1 protein and viral L2 protein. The L1 and/or L2 proteins may, in some embodiments be wild-type viral proteins. In some embodiments, L1 and/or L2 proteins may be altered by mutation and/or insertion/deletion. In certain embodiments, amino acids in surface-exposed loops of the HPV nanoparticle comprising L1 and/or L2 are mutated, inserted and/or deleted. In certain embodiments, mutation, deletion and/or insertion of amino acids in surface-exposed loops leads to changes in immunogenicity of the HPV nanoparticle. In certain embodiments, immunogenicity can be altered in such way that HPV nanoparticles of a certain serotype are no longer recognized by antibodies raised against this serotype. In these embodiments, the altered HPV nanoparticle is immuno-silent in the host harboring the serotype specific antibodies.

Accordingly, in some embodiments, HPV-based particles of the invention may be modified to have reduced or altered immunogenicity. Such particles may be selected for delivery to patients that have a neutralizing anti-HPV response. In some embodiments, a series of HPV-based particles that have different serotypes are administered to a subject for therapeutic purposes to reduce the effect of a neutralizing immune response against any one of the serotypes. For example, a first serotype may be used for a first set (e.g., 1, 2, 3, 4, 5, 5-10, or more) of administrations to a subject. Subsequently, a second serotype may be used for a second set (e.g., 1, 2, 3, 4, 5, 5-10, or more) of administrations to reduce the impact of a neutralizing immune response that the subject develops against the first serotype. It should be appreciated that further sets of administration may involve a third, fourth, fifth, etc. serotype. The different serotypes may be naturally occurring serotypes, chimeric serotypes, other mutant serotypes, or any combination thereof. It should be appreciated that such serial or sequential applications may be used for chronic administration (e.g., treatment) of a particular compound (e.g., the same one in each of the different serotypes), or a series of different compounds, over a time period of months and/or years.

In some embodiments, mutation, deletion and/or insertion of amino acids are introduced in the viral capsid proteins L1 and/or L2 in such a way that the resulting HPV nanoparticle does not lose the ability to deliver therapeutic agents to the target cell. In some embodiments, the HPV nanoparticle does not lose the ability to transfer nucleic acids (e.g., siRNA or shRNA) into target cells.

In some embodiments, immunogenicity can be altered in such way that HPV nanoparticles of a certain serotype induce an immune response that produces cross-specific neutralizing antibodies. In these embodiments, the HPV nanoparticle is altered in such way that it exhibits multiple sero-specific epitopes on its surface (for example by insertion of epitopes in surface-exposed loops) or that it exhibits epitopes that are more conserved between serotypes (for example by insertion of portions of the L2 protein in surface-exposed loops, or by linking conserved epitopes to the surface of the HPV nanoparticle). In some embodiments, production of cross-specific neutralizing antibodies are induced in an HPV-infected individual that have undergone treatment to eliminate or reduce the number of HPV-infected cells. In some embodiments, the HPV-infected individual has undergone treatment to eliminate or reduce the size of a HPV-associated tumor. In these embodiments, production of cross-specific neutralizing antibodies may be induced to generate an immune response that is sufficient for immune-surveillance of the HPV-infected cells that may remain after treatment. The resulting immune-surveillance, in some embodiments, is sufficient to prevent new infection of HPV or repopulation of HPV-infected cells or recurrence of HPV-infected tumors. In some embodiments, cross-specific neutralizing antibodies are effective against one or more HPV serotypes.

In certain embodiments, the therapeutic agents delivered by the VLP-based delivery system are nucleic acids. Therapeutic agents that are nucleic acids can be, for example, siRNA or shRNA molecules or plasmids encoding them. Other therapeutic agents can be, for example, small molecules, such as small molecules with anti-viral or anti-cancer activity.

In certain embodiments, administering to a subject having a HPV infection or a HPV-associated cancer, such as a cervical cancer, or lesion one or more therapeutic agents delivered by a VLP-based delivery system leads to killing and/or clearance of HPV-infected cells. HPV-infected transformed cells are thought to be causative for HPV-associated cancers or lesions. In some embodiments, killing and/or clearance of the HPV-infected cells leads to partial or complete remission of the HPV-associated cancer.

In some embodiments, the treatment methods described herein can be combined with the administration of other therapeutic agents (e.g., anti-cancer agents and/or antiviral agents) and/or immune-modulators and/or radiotherapy or immunotherapy either before, concurrently or after treatment with HPV-nanoparticles comprising therapeutic agents. In some embodiments, the anti-cancer and/or anti-viral agents can be delivered by the HPV nanoparticles. In some embodiments, the anti-cancer and/or anti-viral agents can be administered together with the HPV nanoparticles or can be administered separately, e.g., at a different time or a different site of administration or via a different route of administration.

In some embodiments, most or all HPV-infected cells in a subject treated according to the methods described herein are killed and cleared and HPV is no longer detectable in the HPV-infected subject. In other embodiments, some HPV-infected cells in a subject are killed or cleared and HPV is still detectable in the HPV-infected subject. In some embodiments, a subject having a HPV-associated lesion or cancer may experience partial or complete remission of the cancer or lesion. In some embodiments, subjects do not experience a recurrence of the lesion or cancer or viral infection. In other embodiments, subjects experience a recurrence of the lesion or cancer or viral infection. In some embodiments, the methods of treatment described herein are further combined with anti-viral treatment during and/or after treatment with HPV nanoparticles comprising therapeutic agents. Anti-viral treatment may be given to prevent, for example, HPV replication, viral spreading and/or repopulation of cells with HPV that has survived the initial treatment or that have entered the body of the subject as a new infection.

In other embodiments, altered HPV nanoparticles are administered at the end of the initial treatment regimen. The HPV nanoparticles are altered in such way that they exhibit multiple sero-specific epitopes on its surface or that they exhibit epitopes that are more conserved between serotypes. In some embodiments, administration of such altered HPV nanoparticles may induce a local immune response directed against the administered epitopes, for example inducing an increase in cross-specific neutralizing antibodies, that is sufficient for immune-surveillance capable of detecting and killing newly HPV-infected cells. In some embodiments, prevention of new viral infection and/or spreading and repopulation is sufficient inhibits recurrence of the HPV-associated cancer or lesion.

In certain embodiments, the methods described herein comprise administration of HPV nanoparticles comprising one or more therapeutic agents via different routes. In some embodiments, HPV nanoparticles are administered via topical application. In some embodiments, topical administration is targeted to mucosal membranes. For example, the HPV nanoparticle comprising one or more therapeutic agents can be applied topically to or adjacent to an epithelium such as the cervical epithelial or topically to or adjacent to an epithelial lesion such as cervical or anal epithelial carcinoma.

In certain embodiments, HPV nanoparticles comprising altered viral capsid proteins are provided, wherein the viral capsid proteins are altered by mutations of wild-type amino acids, insertions of additional amino acids, an/or deletion of wilt-type amino acids, as described herein. In certain embodiments, the altered HPV nanoparticles are more or less immunogenic in a subject or have an altered immunogenicity. In some embodiments, the altered HPV nanoparticles maintain the ability to deliver or transfer therapeutic agents to a target cell.

Accordingly, aspects of the invention relate to methods and compositions for delivering one or more compounds to a subject. In some embodiments, a modified human papilloma virus (HPV)-like particle is used, wherein the particle comprises one or more heterologous compounds packaged in an HPV-like particle comprising a surface protein having altered immunogenicity. The heterologous compounds are non-HPV molecules (e.g., a compound that is not an HPV genome, not an HPV nucleic acid, and/or not an other HPV molecule). Such compounds may be therapeutic or other medical compounds. In some embodiments, the compound may be one or more of: a therapeutic or medical agent, a nucleic acid or a small molecule, or an imaging or contrast agent. In some embodiments, the therapeutic agent is an siRNA, an shRNA, an antisense nucleic acid, or a nucleic acid encoding an siRNA, an shRNA, or an antisense nucleic acid. In some embodiments, the siRNA, shRNA, or antisense nucleic acid targets HPV-E6 and/or HPV-E7. In some embodiments, the small molecule is an anti-viral agent. In some embodiments, the small molecule is an anti-cancer agent (e.g., Gemcitabine).

It should be appreciated that methods and compositions of the invention may be provided along with one or more other agents (e.g., an anti-viral agent, an anti-cancer agent, for example Gemcitaine, or any combination thereof).

In some embodiments of methods and compositions of the invention, the HPV-like particle comprises an L1 protein or an L1 protein and an L2 protein. In some embodiments of methods and compositions of the invention, the surface protein is a modified L1 protein with a modified FG loop sequence. In some embodiments, the L1 protein has a sequence of an HPV16, HPV31, HPV33, HPV34, HPV35, HPV52, HPV58, HPV73, or HPV91 serotype, and wherein the FG loop of the L1 protein has one or more amino acid changes that alter the immunogenicity of the protein in a human subject. In some embodiments, the one or more amino acid changes are at one or more of positions $X_1$-$X_{17}$ of SEQ ID NO: 11. In some embodiments, the amino acid at position $X_{16}$ is not altered. In some embodiments, one or more of positions $X_1$, $X_2$, $X_3$, $X_5$, $X_6$, $X_{11}$, and $X_{14}$ of SEQ ID NO: 11 are modified. In some embodiments, 2-3 of positions $X_1$, $X_2$, $X_3$, $X_5$, $X_6$, $X_{11}$, and $X_{14}$ of SEQ ID NO: 11 are modified. In some embodiments, 4-7 of positions $X_1$, $X_2$, $X_3$, $X_5$, $X_6$, $X_{11}$, and $X_{14}$ of SEQ ID NO: 11 are modified. In some embodiments, 3 of positions $X_1$, $X_2$, $X_3$, $X_5$, $X_6$, $X_{11}$, and $X_{14}$ of SEQ ID NO: 11 are modified. In some embodiments, positions $X_6$, $X_{11}$, and $X_{14}$ of SEQ ID NO: 11 are modified. In some embodiments, all of positions $X_1$, $X_2$, $X_3$, $X_5$, $X_6$, $X_{11}$, and $X_{14}$ of SEQ ID NO: 11 are modified. In some embodiments, the L1 protein has a sequence of an HPV16 serotype with positions $X_6$, $X_{11}$, and $X_{14}$ of SEQ ID NO: 11 changed to T, T, and N, respectively, and the remainder of the positions of SEQ ID NO: 11 having an amino acid characteristic of an HPV16 serotype. In some embodiments, the L1 protein has a sequence of an HPV16 serotype with positions $X_1$, $X_2$, $X_3$, $X_5$, $X_6$, $X_{11}$, and $X_{14}$ changed to F, S, T, S, T, T, and N, respectively, and the remainder of the positions of SEQ ID NO: 11 having an amino acid characteristic of an HPV16 serotype.

It should be appreciated that in some embodiments, an HPV-like particle is administered to a subject that does not have a neutralizing immune response against the serotype of the surface protein, for example when the subject has not been immunized against the serotype of the surface protein, or when the subject has not been infected with an HPV having the same serotype as the serotype of the surface protein in the HPV-like particle. In some embodiments, the immune response of the subject is evaluated prior to selecting an HPV-like particle for administration.

In some embodiments, an HPV-like particle is administered to a mucosal tissue. The mucosal tissue may be at any locus as described herein (e.g., cervical, urogenital, oral, etc.). Furthermore, in some embodiments, an HPV-like particle is administered to an epidermal locus (e.g., to treat an epidermal or skin cancer or infection).

It should be appreciated that compositions of the invention may be administered topically and/or via any other suitable route (e.g., via injection, aerosol, spray, or other form of administration).

Compositions of the invention may be administered to a tissue infected with a virus, bacteria, and/or other microbes or parasites. In some embodiments, a site of infection may be infected with several different organisms (e.g., multiple viruses and/or other microbes, for example HPV and a herpes virus, for example HSV). Accordingly, a composition of the invention may include a compound that broadly targets several different organisms, or several different compounds that are each targeted to a different organism, or a combination thereof. In some embodiments, the same HPV-like particle may contain different therapeutic compounds. In some embodiments, a composition or treatment regimen may include two or more different HPV-like particles each containing a compound that is targeted to a particular infection.

Compositions of the invention may be administered to a subject to treat a cancer (e.g., at or near the site of administration). In some embodiments, the cancer may be associated with an infection (e.g., an HPV or HSV infection). In some embodiments, the cancer may not be associated with an infection. Accordingly, aspects of the invention may be used to treat skin cancer (e.g., non-melanoma skin cancer).

In some embodiments, compositions of the invention may be administered to a subject having an immune system deficiency to treat a condition (e.g., infection, cancer, or other condition) associated with the immune system deficiency. The immune system deficiency may be caused by an infection (e.g., an HIV infection, AIDS) or other condition (e.g., cancer).

In some embodiments, an HPV-like particle of the invention may be administered along with a composition that promotes a non-specific immune response (e.g., at or near the site of administration). The non-specific immune response may be helpful to treat the infection and/or a cancer or other condition. In some embodiments, an increased immune response in response to the administration of several HPV-like particles with different serotypes may be beneficial. Accordingly, some compositions of the invention comprise several different serotypes.

In some embodiments, a chronic administration of a composition may be accomplished by administering a first HPV-like particle comprising a compound to a subject for a first period of time, and administering a second HPV-like particle comprising the compound to the subject for a second period of time, wherein the first and second HPV-like particles have different serotypes. Further administrations may be made using further serotypes. In some embodiments, the serotypes of the first and second HPV-like particles are independently naturally occurring or altered serotypes. In some embodiments, the serotype of the first and/or second HPV-like particle is a chimeric serotype.

In some embodiments, a composition or method of the invention may involve administering an HPV-like particle that has a chimeric serotype by including an L2 sequence fused in an L1 loop. In some embodiments, the L2 sequence is attached to the surface of an L1 particle. In some embodiments, the L2 sequence consists of residues 13 to 88 of the HPV31 L2 protein.

These and other aspects of the invention are described in more detail in the following non-limiting examples and the description.

BRIEF DESCRIPTION OF THE DRAWINGS

FIG. 1 depicts the location of siRNAs on E6 and E7 genes of HPV-16.

FIG. 2 depicts a bar graph showing the role of $ZnCl_2$ in the production of pseudovirions coding for luciferase. The luciferase gene expression was evaluated in 293FT cells transfected with pseudovirions reassembled without $ZnCl_2$ and in 293FT, TC1, C33, and CaSki cells transfected by pseudovirions generated in the presence of $ZnCl_2$.

FIG. 3 depicts A) a photograph of reverse transcribed mRNA extracted from CaSki cells that were transfected with LacZ, E6-1, E6-2, E7-1, and E7-2 shRNA. cDNA was PCR amplified with E6 and E7 gene-specific primers and glyceraldehyde-3-phosphate dehydrogenase (GAPDH) primers as control. B) a photograph of a western blot of cells extracts from CaSki cells (Mock) that were transfected with LacZ, E6-2, E6-1, E7-2, and E7-1 shRNAs. Extracts were analyzed usingp53 and β-actin antibodies.

FIG. 4 shows a bar graph depicting effects of E6 and E7 shRNAs on C33 (gray columns), CaSki (black columns) and TC1 (white columns) cells growth. Cells (C) were transfected with LacZ, E6-1, E6-2, E7-1, and E7-2 shRNAs.

FIG. 5 depicts a photograph showing inhibition of TC1 tumor growth in C57 BL6 mice. TC1 cells were transfected in vitro. A) comparison of tumors obtained after injection of TC1 cells treated with VLPs alone (bottom) and E7-1 pseudovirions (top). B) bar graph quantification of the comparison of the weight of tumors after different treatments with shRNA pseudovirions and shRNA lentivirus.

FIG. 6 depicts graphs showing inhibition of TC1 tumor growth in C57 BL6 mice after intratumoral injection of control shRNA and E7-1 shRNA pseudovirions (Pv). A) evolution of tumor size (mean diameter) after the first injection of control shRNA or E7-1 shRNA pseudovirions. B) weight of tumors at 3 weeks in mice treated with control shRNA and E7-1 shRNA pseudovirions.

FIG. 7 (a) depicts graphs of representative surface plasmon resonance data. (b) depicts an epitope map constructed from the interaction studies between the 15 HPV31 MAbs that recognized conformation epitopes by SPR. Antibodies that neutralized internalization are in black and those that neutralized cell attachment are underlined. The H31.D24 antibody was non-neutralizing (boxed). (c) The AQ5 antibodies that inhibited VLP binding to heparin are underlined.

FIG. 8 depicts the mapping the HPV31 L1 protein epitopes recognized by a non-neutralizing MAb (H31.D24) and four neutralizing MAbs (H31.B1, H31.F7, H31.F16, and H31.H12) using the bacterial display method.

FIG. 9 depicts MAb neutralization of pseudovirions pre- and postattachment. (a) Inhibition of HPV31 pseudovirion entry by HPV31 MAbs. HPV31 pseudovirions were preincubated with HPV31 MAbs and then added to cells. (b) Inhibition of HPV31 pseudovirion internalization by HPV31 MAbs. HPV31 pseudovirions were preattached to cells and then HPV31 MAbs were added. The five MAbs investigated using the bacterial display method are grouped at the right of the figure. Gray columns, neutralizing type-specific MAbs; black column, cross neutralizing F7 MAb.

FIG. 10 depicts VLP binding to HS and ECM: effects of HPV31 MAbs and L1 C-terminal deletion. (a) Inhibition of heparin binding after preincubation of VLPs with MAbs. (b) Inhibition of ECM binding after preincubation of VLPs with MAbs. The five MAbs investigated using the bacterial display method are grouped at the right of the figure. Gray columns: neutralizing type-specific MAbs; black column: F7 cross neutralizing MAb; open column: D24 non-neutralizing MAb. The values are the percentage of inhibition with SD. Inhibition greater than 50% was considered positive.

FIG. 11 depicts heparin binding of native VLPs (black columns) and denatured VLPs (grey columns) for type 16 and type 31 with or without C-terminal deletions (D9 and D31).

FIG. 12 depicts the localization of the epitopes recognized by five monoclonal antibodies on the FG loop of HPV31. Position of the epitopes recognized on the FG loop of the HPV31 L1 protein by four MAbs.

FIG. 13 depicts a sequence alignment of the FG loops of HPV16 and HPV31, respectively, and mutations inserted in the HPV16 FG loop wild-type sequence to generate chimeras (X and Y).

FIG. 14 depicts a graph showing luciferase activity (counts per minute, CPM) extracts from COS-7 cells transfected with wt HPV16, and chimeras HPV X and HPV Y.

FIG. 15 depicts a table showing titers (geometric mean titers, GMT) of HPV16, HPV31, HPV X, and HPV Y-specific antibodies measured in an ELISA assay from mice immunized with HPV16, HPV31, HPV X or HPV Y.

FIG. 16 depicts electron micrographs of chimeric VLPs L1STII (A) and 31L1-16L2 (13-88) (B) (bar=200 nm).

FIG. 17 depicts bar graphs showing analysis of the antigenicity of chimeric HPV16 L1-STII, HPV16 L1STIIL2SA and HPV31 L1-16 L213-88 VLP particles by ELISA. Results were adjusted to the L1 reactivity using CamVir-1 Mab. Results are presented as relative reactivity, i.e. the ratio between the OD obtained with the antigen considered and the OD obtained with the reference antigen (*). Particles were analyzed in native conditions using monoclonal antibodies directed against conformational (C) epitopes, and StrepTagII or L2 exposure. HPV16 L1 STII and HPV16 L1STII L2SA were analyzed with H16.V5 (C), a monoclonal antibody directed against the StrepTagII sequence and a polyclonal HPV16 L2 antiserum. HPV16 L1 VLPs and L1L2 31 VLPs were used as controls. HPV31 L1-16 L213-88VLPs were analyzed using H31.F16 (C), and a polyclonal HPV16 L2 antiserum. Results are means of duplicates.

FIG. 18 depicts a photograph of a Western blot analysis of the expression of L2 protein. 1) purified L2SA fusion protein, 2) after interaction with L1STII VLPs and 3) with L1 VLPs; 4) in Cos-7 cells transduced with HPV58 pseudovirions encoding GFP and 5) with HPV58 pseudovirion encoding L2.

Figure 19:
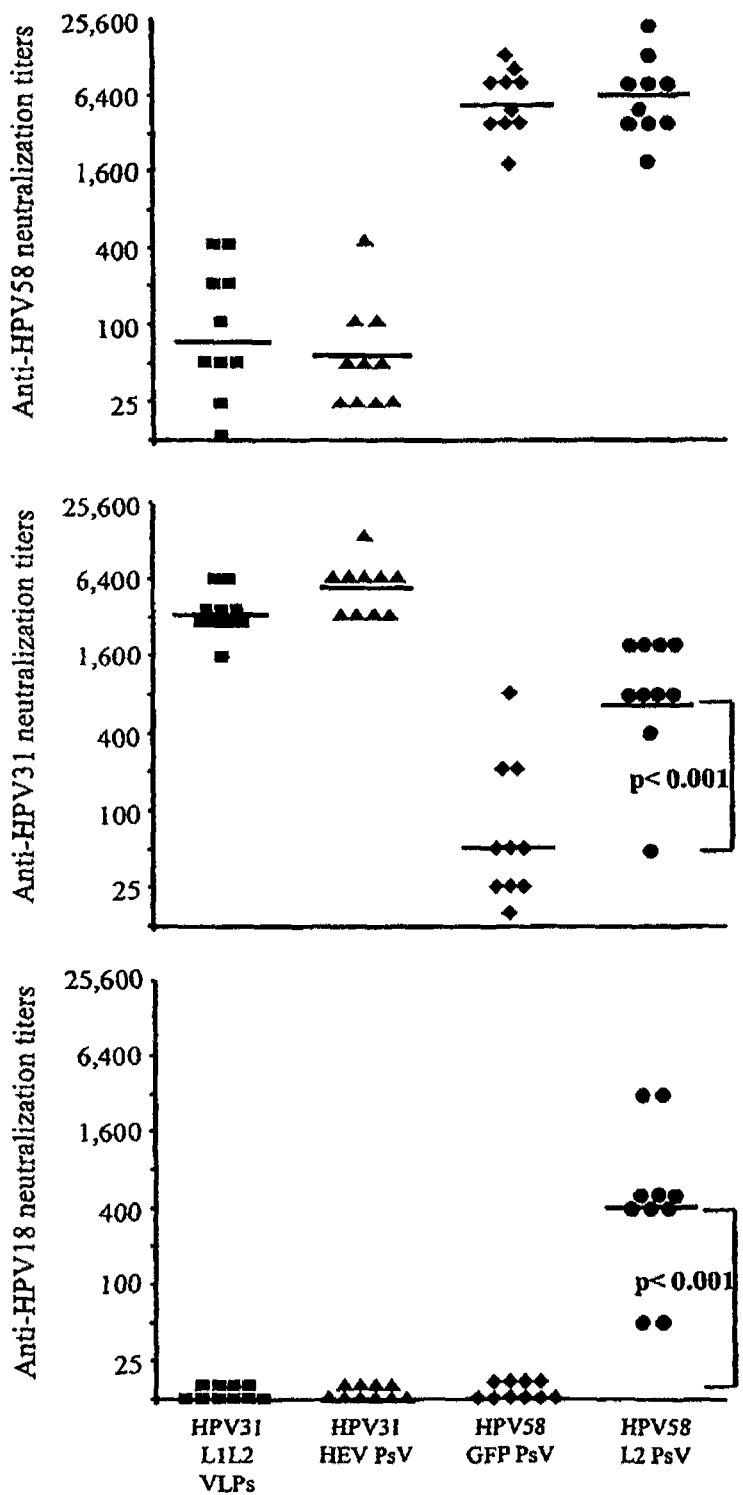

FIG. 19 depicts a graph showing detection of HPV31, HPV58 and HPV18 neutralizing antibodies. The individual mouse neutralizing titers are the means of the last reciprocal dilution providing more than 50% inhibition of luciferase expression. Geometric mean titers are indicated by bars.

DETAILED DESCRIPTION OF THE INVENTION

Aspects of the invention relate to methods and compositions based on HPV particles and their use for medical and/or therapeutic applications. In some embodiments, HPV-based particles are used to deliver one or more agents (e.g., therapeutic agents, imaging agents, and/or other medical agents) to a target cell or tissue (e.g., a mucosal tissue, for example a mucosal tissue surface).

In some embodiments, aspects of the invention relate to an HPV particle that contains one or more naturally occurring HPV surface proteins (e.g., L1 and/or L2 proteins) and that is loaded with one or more medical and/or therapeutic agents, or a combination of two or more thereof. In some embodiments, aspects of the invention relate to modified HPV-based particles that contain one or more variant surface proteins (e.g., variant L1 and/or L2 proteins) that have reduced or modified immunogenicity in a subject. The modification may be an amino acid sequence change that reduces or avoids neutralization by the immune system of the subject. In some embodiments a modified HPV-based particle is a particle that contains a recombinant HPV protein (e.g., a recombinant L1 and/or L2 protein) that includes one or more amino acid changes that alter the immunogenicity of the protein in a subject (e.g., in a human subject). In some embodiments, a modified HPV-based particle has an altered immunogenicity but retains the ability to package and deliver molecules to a subject. Accordingly, modified HPV particles of the invention may be loaded with one or more agents (e.g., instead of an HPV nucleic acid). Such particles may be delivered to a subject without inducing an immune response that would be induced by a naturally-occurring HPV particle.

Certain embodiments of the invention are useful for delivering one or more therapeutic agents to diseased tissue (e.g., diseased mucosal tissue). In some embodiments, a diseased tissue (e.g., mucosal tissue, epithelial tissue, or endothelial tissue) may be an infected tissue (e.g., infected with a virus such as HPV or HSV). In some embodiments, the mucosal tissue is cervical tissue and the disease is dysplasia or cancer (e.g., cervical dysplasia, cervical cancer, for example associated with persistent HPV infection). However, in some embodiments, HPV-based particles may be used to deliver compositions to other tissues (e.g., epidermis). In some embodiments, HPV-based particles may be used to treat HPV. However, in some embodiments, HPV-based particles may be used to deliver therapeutic agents to treat other diseases or conditions.

Some embodiments of the invention are useful for delivering one or more imaging or contrast agents to a subject. For example, quantum dots, metals, and/or other imaging agents may be delivered. In some embodiments, agents may be used to track early stage diseases (e.g., early stage metastasis). In some embodiments, radiosensitive agents may be used to enhance the effects of radiotherapy. In some embodiments, agents may be delivered to induce tumor cells to express different receptors or sugars on their membrane. For example, aspects of the invention may be used to deliver an agent that promotes the expression in a tumor cell of a signal that would enhance the immune system recognition of the tumor (e.g., an agent that would make the tumor cell look like a bacteria, or a virus). In some embodiments, an agent may be delivered to block the uptake of a sugar by a tumor cell. However, it should be appreciated that any suitable therapeutic and/or other medical agent may be delivered according to aspects of the invention.

In some embodiments, aspects of the invention relate to HPV-based particles that are modified to display epitopes from two or more different naturally-occurring HPV variants. Such modified particles may be used to provide immunization against infection by any of two or more naturally occurring HPV variants.

In some embodiments, aspects of the invention relate to protocols for administering one or more different HPV particles for therapeutic applications. The different HPV particles may be any combination of different HPV variants, HPV-based particles containing different agents, and HPV particles that have modified immunogenicity.

In certain embodiments, HPV nanoparticles may be used to deliver one or more therapeutic agents to mucosal cells (e.g., HPV-infected cells). In other embodiments, altered HPV nanoparticles may be used to deliver the one or more therapeutic agents to target cells. In certain embodiments, the altered HPV nanoparticle is immune-silent in the host harboring serotype specific antibodies. For example, a subject infected with a first HPV serotype (e.g., HPV-16) develops antibodies against that serotype. In such subject, viral particles having the first serotype (e.g., wild-type HPV16-based VLPs) may induce an immune-response that reduces the efficacy of the VLP-based drug delivery.

In another example, a subject may be immunized against HPV (e.g., with GARDASIL and CERVARIX) and has developed neutralizing antibodies against a first and/or second serotype (e.g., HPV-16 and HPV18). In such a subject, viral particles having the first and/or serotype (e.g., wild-type HPV16- or HPV18-based VLPs) may induce an immune-response that drastically reduces the efficacy of the VLP-based drug delivery.

However, HPV nanoparticles can be altered by methods described herein so that the altered HPV nanoparticle is not recognized by the first serotype-specific antibodies in the host (e.g., the HPV-16 serotype-specific antibodies in the host) and/or the second serotype-specific antibodies in the host (e.g., the HPV-18 serotype-specific antibodies in the host). Such altered HPV or HPV nanoparticles comprising L1 and/or L2 proteins from a different serotype may be used therapeutically. For example, such altered HPV nanoparticles or VLP based on a different serotype may be used to deliver one or more therapeutic agents to an HPV-immunized or HPV-infected host without inducing a serotype-specific immune response and/or without being neutralized by a host response and without losing efficacy. Such altered HPV nanoparticles or VLP based on a different serotype may be used repeatedly (e.g., for 1, 2, 3, 4, 5, 6, 7, 8, 9, 10 or more administrations) to deliver therapeutic agents. In certain embodiments, the subject will develop new antibodies that will recognize the altered HPV nanoparticle or VLP based on a different serotype. Also, a subject that is not infected with HPV may develop an immune response against the serotype of an HPV-based particle that is administered to the subject for therapeutic purposes. In these cases, a second differently altered HPV nanoparticle or a second HPV nanoparticle comprising L1 and/or L2 proteins from a further different serotype may be used for continued delivery of therapeutic agents to a subject (e.g., to HPV-infected cells or cells within a subject that has been immunized against HPV or treated with HPV-based compositions of the invention) without inducing an immune response (e.g., a neutralizing immune response) specific to the original HPV serotype and the second altered HPV nanoparticle. In the event that a subject develops an immune response (or in order to prevent the development of an immune response) against the second altered HPV nanoparticle or the second VLP containing second L1 and/or L2 proteins, a third altered HPV nanoparticle or a third VLP containing third L1 and/or L2 proteins may be used. This process may be repeated several times with a series of different altered HPV nanoparticles and/or different VLPs containing a series of different L1 and/or L2 proteins may be used. It should be appreciated that in some embodiments, the switch from one set of particles to a different one may be made when the first set looses efficacy in a subject, when an immune response to the first set is detected in the subject, or at a predetermined time (e.g., after a predetermined number of administrations or a predetermined time period of administration of the first set) after treatment is initiated.

In certain embodiments, the VLP based on a different serotype is chosen on the basis of genotype and/or serotype similarity of the HPV. In some embodiments, the VLP based on a different serotype is chosen on the basis of neutralizing cross-reactivity of antibodies. In some embodiments, a VLP based on a different serotype is chosen that is most distantly related to the first and/or second serotype against which the subject has developed neutralizing antibodies. For example, HPV18 and HPV45 are closely related and show a high degree of cross-protection of neutralizing antibodies. HPV16 and HPV31 are closely related and show a high degree of cross-protection of neutralizing antibodies. HPV58 is more distantly related to HPV16 and HPV18 and little or no cross-protection by neutralizing antibodies is observed.

Accordingly, a treatment series may involve administering a series of VLP compositions of the invention (e.g., containing one or more therapeutic agents), wherein each successive VLP composition is based on a VLP from a different HPV serotype, for example, from remotely related serotypes. For example, in a subject immunized against HPV16 and HPV18, a suitable VLP based on a different serotype can be a particle comprising L1 and/or L2 proteins from wild-type HPV58.

In another embodiment, the VLP distantly related to the first and/or second serotype against which the subject has developed neutralizing antibodies may be selected from papilloma viruses that are not HPV. In some embodiments, VLP may comprise capsid proteins from a papilloma virus that infects a mammal that is not human, e.g., bovine papilloma virus (BVP) or cottontail rabbit papilloma virus (CRVP) or Shope papilloma virus. It should be appreciated that a treatment series may involve a series of VLPs based on different HPV serotypes and/or different papilloma viruses that infect other non-human hosts.

The differently altered HPV nanoparticle or the HPV nanoparticle of a different serotype may be used for delivery of therapeutic agents until the subject develops antibodies to the differently altered HPV nanoparticle or the HPV nanoparticle of a different serotype. In certain embodiments, using the method described above, altering VLPs based on serotype-differences and/or immune response altering mutations, subjects may be treated for multiple rounds with therapeutic agents without the loss of efficacy of the delivery system due to immune responses of the subject. In some embodiments, such regimens allow repeated or continued treatment of the HPV infection and/or HPV-associated cancer until essentially all HPV-infected cells are eliminated and/or remission (partial or complete) of the cancer or lesion has occurred. However, it should be appreciated that such regimens may be used for repeated or continued treatment of other conditions according to aspects of the invention.

In some embodiments, a subject is vaccinated using a HPV vaccine (such a those commercially available, e.g., GARDASIL and CERVARIX). In these embodiments, the immunization protects the subject from becoming infected with the viruses that are targeted by the vaccine (for example, the viruses for which the subject has raised an immune response upon vaccination) and from developing HPV-associated diseases caused by these vaccine-specific viruses. However, it will be appreciated that the currently available vaccines will not protect against infection of all HPV genotypes and/or serotypes. In some embodiments, HPV-vaccinated subjects will become infected with an HPV (e.g., a high-risk HPV) that is not targeted by the vaccine, for example, for which the vaccinated subject has not developed an immune response. In some embodiments, the vaccinated subject encounters multiple incidences of infection with different HPV types. In some embodiments, subjects may become infected with one, two, three, four, five, six, seven, eight, nine, ten, or more different HPV types that infect—and are harbored in—different cells in the subject. In some embodiments, a vaccinated subject becoming infected with a high-risk HPV for which the vaccinated subject has not developed an immune response may develop a HPV-associated disease, e.g., a HPV-associated dysplasia or cancer, caused by the high-risk HPV for which the vaccinated subject has not developed an immune response. In these embodiments, the subject may be treated with the VLPs described herein using the methods described herein.

For example, a subject immunized with one of the commercially available vaccines may develop neutralizing antibodies against HPV16 and 18 and may also develop neutralizing antibodies against HPV6 and 11. The immunized subject is protected against the development of cervical pre-cancers and/or genital warts caused by these HPV-types (HPV 16, 18 (cancer), and HPV 6, 11 (warts)). A subject having developed neutralizing antibodies against HPV16 and 18 upon immunization may develop some neutralizing antibodies that display cross-reactivity with other HPV types (such as, e.g., HPV 31, for neutralizing antibodies that are raised against HPV 16, and HPV 45 for neutralizing antibodies that are raised against HPV 18). However, immunized subjects will still be susceptible to infection with other high-risk HPV types for which cross-neutralizing antibodies are not developed by the subject (such as, e.g., HPV58, or others). Additional high-risk HPV types that may infect the immunized subject can be, for example, HPV-33, HPV-35, HPV-39, HPV-51, HPV-52, HPV-56, HPV-59, HPV-68, and HPV-69. If the immunized subject has not developed cross-neutralizing antibodies, or has not developed sufficiently specific cross-neutralizing antibodies, or has not developed sufficient titers of cross-neutralizing antibodies, the immunized subject is still at risk of developing a HPV-associated disease, such as dysplasia or cancer, when infected with one or more of the high-risk HPV types, for which no sufficient protection was developed by the subject.

In such a subject, modified VLPs described herein or viral particles of a different (more distantly related) serotype (e.g., wild-type HPV58-based VLPs) comprising on or more therapeutic agents (e.g., E7 siRNA) may be administered to the subject to treat early stage disease developed by the persistent high-risk HPV infection of that subject caused by a high-risk HPV for which no sufficient protection was developed by the subject. In this example, the treatment enables the elimination of the early dysplasia and additionally may provide broader cross-protection to the subject against further infection with other additional HPV types.

In some embodiments, HPV nanoparticles comprise viral L1 protein. In some embodiments, HPV nanoparticles comprise viral L1 protein and viral L2 protein. The L1 and/or L2 proteins may, in some embodiments, be wild-type viral proteins. In some embodiments, L1 and/or L2 proteins may be altered by mutation and/or deletion so that the resulting L1 and/or L2 proteins comprise only 'minimal' domains essential for assembly of the nanoparticle. In some embodiments, L1 and/or L2 proteins may also be fused to other proteins and/or peptides that provide additional functionality. These other proteins may be viral or non-viral and could, in some embodiments, be for example host-specific or cell type specific. It should be appreciated that VLPs may be based on particles containing one or more recombinant proteins or fragments thereof (e.g., one or more HPV membrane and/or surface proteins or fragments thereof). In some embodiments, VLPs may be based on naturally-occurring particles that are processed to incorporate one or more agents as described herein, as aspects of the invention are not limited in this respect. In certain embodiments, particles comprising one or more targeting peptides may be used. Other combinations of HPV proteins or peptides may be used as aspects of the invention are not limited in this respect.

In some embodiments, viral wild-type capsid proteins are altered by mutations, insertions and deletions. All conformation-dependent type-specific epitopes identified to date are found on the HPV-VLP surface within hypervariable loops where the amino acid sequence is highly divergent between HPV types, which are designated BC, DE, EF, FG and HI loops. Most neutralizing antibodies are generated against epitopes in these variable lops and are type-specific, with limited cross-reactivity, cross-neutralization and cross-protection. Different HPV serotypes induce antibodies directed to different type-specific epitopes and/or to different loops.

Provided herein are methods to exploit the limited cross-reactivity of antibodies generated against specific HPV serotypes for therapy. In certain embodiments, viral capsid proteins, HPV L1 and/or L2, are mutated at one or more amino acid positions located in one or more hypervariable and/or surface-exposed loops. The mutations are made at amino acid positions within the loops that are not conserved between HPV serotypes. These positions can be completely non-conserved, that is that any amino acid can be at this position, or the position can be conserved in that only conservative amino acid changes can be made.

Conservative amino acid changes may be made according to functional, chemical or structural considerations. For example, conservative amino acid changes may be made according to chemical similarity: acidic (D/E), aliphatic (A/G/I/LN), amide (N/Q), aromatic (F/W/Y), basic (R/H/K), hydroxyl (S/T), imino (P), sulfur (C/M); or functional similarity: acidic (D/E), basic (R/H/K), hydrophobic (A/I/L/M/F/P/WN), polar (N/C/Q/G/S/T/Y); or similarity in charge: acidic, basic, neutral; or structural similarity: ambivalent (A/C/G/P/S/T/W/Y), external (R/N/D/Q/E/H/K), internal (I/L/M/F/V), wherein any amino acid of a group of amino acids in parentheses can be changed into another in that group and such change would be considered a conservative change according to the consideration applied, e.g., structural, functional, or chemical. In some embodiments, one or more factors may be considered.

In certain embodiments, amino acid changes are introduced in one or more loops at one or more positions that alter the wild-type amino acid sequence of one serotype in the one or more amino acid positions and in the one or more loops to an amino acid sequence that is found in another HPV serotype. For example, if in one loop the amino acid sequence for serotype X is ABCDEFG and in the same loop on a different serotype Y the amino acid sequence is ABHIJG (where ABCDEFG and ABHIJFG are different amino acid sequences) then AB and FG are conserved and CDE may be mutated. Mutations may be introduced in serotype Y in C or D or E, or may be introduced in CD or DE or CE, or may be introduced in CDE. In these embodiments, C can be mutated to H, D can be mutated to I, and E can be mutated to J. In these embodiments, the one or more loops may have the amino acid sequence of one serotype (e.g., Y) whereas the remainder of the protein and the remainder of the (unaltered loops) are of a different serotype (e.g., X). In these embodiments, only a small portion of the viral capsid protein is mutated.

Table 2 shows examples of an alignment of FG loops of different HPV types:

```
256-FVRHLFNRAGAVGENVPDDLYIKGS--GSTANLASSNYFPT-294        (SEQ ID NO: 1)
                                                         HPV16

257-FVRHFFNRSGTVGESVPTDLYIKGS--GSTATLANSTYFPT-295        (SEQ ID NO: 2)
                                                         HPV31

256-FVRHFFNRAGKLGEAVPDDLYIKGS--GTTASIQSSAFFPT-294        (SEQ ID NO: 3)
                                                         HPV33

279-FVRHLFNRAGTVGDAIPDDLMIKGT--GNTASPSSCVFYPT-317        (SEQ ID NO: 4)
                                                         HPV34

259-FVRHLFNRAGTVGETVPADLYIK----GTTGTLPSTSYFPT-295       (SEQ ID NO: 5)
                                                         HPV35

285-FVRHFFNRAGTLGDPVPGDLYIKGSNSGNTATVQSSAFFPT-325        (SEQ ID NO: 6)
                                                         HPV52

282-FVRHFFNRAGKLGEAVPDDLYIKGS--GNTAVIQSSAFFPT-320        (SEQ ID NO: 7)
                                                         HPV58

254-FVRHLFNRAGDTGDKIPDDLMIKGT--GNTATPSSCVFYPT-292        (SEQ ID NO: 8)
                                                         HPV73
```

-continued

```
346-FVRHFFNRAGTTGDAVPKDLYIAGT--GNRANIAGSIYYST-384        (SEQ ID NO: 9)
                                                         HPV91

FVRHFFNRAG-VGE-VP-DLYIKGS--GNTA---SS-FFPT                (SEQ ID NO: 10)
     L    S  L D I    M A TNS TRG    GC YYS              Consensus
              T                S     NT Consensus:
                                                         (SEQ ID NO: 11)
FVRHX₁FNRX₂GX₃X₄G(E/D)X₅ (V/I) PX₆DLX₇IX₈G(S/T)-GX₉X₁₀ (A/G)
X₁₁X₁₂X₁₃X₁₄X₁₅X₁₆ (F/Y)(F/Y)X₁₇T
```

The example in Table 2 shows that mutations may be introduced in any position 'X' and conservative mutations may be introduced at any positions marked in parenthesis, while keeping the conserved amino acids (bold) the same. A person of ordinary skill, based on the example in Table 2, can align HPV sequences of any number of HPV viruses for any of the surface exposed hypervariable loops and derive the conserved amino acids and those that are not conserved without undue experimentation using well known alignment programs.

In certain embodiments, one or more amino acid changes may be made in one or more loops, changing the non-conserved wild-type amino acids of one serotype for the equivalent wild-type amino acids of another serotype. For example, according to the example in Table 2, the wild-type amino acid of position 260 (L) of the FG loop of HPV16 may be altered to (F), which is the equivalent wild-type amino acid at position 261 of HPV31. Additionally, the wild-type amino acid of position 264 (A) of the FG loop of HPV16 may be altered to (S), which is the equivalent wild-type amino acid at position 265 of HPV3 I, and so forth. In this manner, one or more loops of the viral capsid protein of one serotype (e.g., FG loop of L1 of HPV16) may be altered to more or less closely mimic the amino acid sequence of the loop of the same viral capsid protein of another serotype (e.g., FG loop of L1 of HPV31) keeping all other amino acids of the capsid protein wild-type (e.g., L1 of HPV16). In some embodiments, altering the amino acids of one or more loops that harbor the major epitopes of a specific serotype to amino acids located in the equivalent positions of the same loop in a different serotype, in the way described here, reduces recognition of the viral particle by HPV-specific antibodies of the immune system of an HPV-infected individual. In some embodiments, the altered HPV nanoparticle is immuno-silent and is not recognized by the HPV-specific antibodies developed by the HPV-infected subject against HPV. For example, a subject immunized or infected with HPV16 develops HPV16-specific antibodies. If the immune system encounters VLPs comprising wild-type L1 protein derived from HPV16 an immune response will occur. If however the immune system encounters VLPs comprising L1 protein derived from HPV16 that is altered in a way described herein an HPV16-specific immune response will not (initially) occur. After repeated challenge with the altered VLP the subject receiving the altered VLP will develop a new immune response directed against the particle. In this case a differently altered VLP and/or a VLP from another serotype can be used for the methods of treatment described herein.

Surprisingly, in some embodiments, where one or more loops of the viral capsid protein of one serotype are altered to mimic the epitope structure of the loops of the viral capsid protein of another serotype, the VLP comprising the altered capsid protein is not recognized by neutralizing antibodies directed against either serotype. According to aspects of the invention, even though the loop (e.g., the FG loop) contains a major epitope, the serotype is determined by that epitope in the context of the remainder of the viral capsid protein. When only the loop is modified without changing the sequence of the remainder of the viral capsid protein, a novel serotype is obtained that surprisingly is not recognized by antibodies against the original serotype (or serotypes when the loop sequence is changed from the sequence of a first serotype to the sequence of a second serotype). In some embodiments, one or more positions can be changed to generate a new serotype while retaining the ability to package and deliver an agent (e.g., a nucleic acid, for example an RNA or DNA, for example a recombinant nucleic acid, for example a therapeutic nucleic acid as described herein).

In some embodiments, one or more of positions $X_1$, $X_2$, $X_3$, $X_5$, $X_6$, $X_{11}$, and $X_{14}$ of the FG loop may be altered to generate a new serotype that is still capable of packaging and delivering an agent (e.g., a heterologous nucleic acid that is different from the HPV nucleic acid, (e.g., a nucleic acid, for example an RNA or DNA, for example a recombinant nucleic acid, for example a therapeutic nucleic acid as described herein). In some embodiments, one or more of these positions in a first L1 protein are changed from the amino acid of a first serotype to the amino acid of a second serotype. For example, in some embodiments all of positions $X_1$, $X_2$, $X_3$, $X_5$, $X_6$, $X_{11}$, and $X_{14}$ may be changed from a first HPV serotype sequence (e.g., an HPV16 serotype sequence) to a second HPV serotype sequence (e.g., an HPV31 serotype sequence) in the context of the first (e.g., the HPV16) L1 sequence. In some embodiments only $X_6$, $X_{11}$, and $X_{14}$ are changed from an amino acid of a first HPV serotype sequence (e.g., an HPV16 serotype sequence) to a second HPV serotype sequence (e.g., an HPV31 serotype sequence) in the context of the first (e.g., the HPV16) L1 sequence. In some embodiments, any combination of $X_1$, $X_2$, $X_3$, $X_5$, $X_6$, $X_{11}$, and $X_{14}$ (e.g., any 1, 2, 3, 4, 5, 6, or 7 of the positions) may be altered from an amino acid of a first serotype to the amino acid of a second serotype without changing the remainder of the L1 sequence. It should be appreciated that the first and second serotypes may be any suitable serotypes (e.g., HPV16, HPV31, HPV33, HPV34, HPV35, HPV52, HPV58, HPV73, HPV91, or any other serotype with specific FG loop sequences). It also should be appreciated that in some embodiments any one or more of these positions may be changed to any conservative or non-conservative amino acid (regardless of whether the change corresponds to an amino acid from another naturally-occurring serotype) in the context of an otherwise unchanged L1 sequence or portion thereof that retains the ability to package and deliver an agent (e.g., a nucleic acid that is different from the natural HPV nucleic acid, or any other agent as described herein).

In some embodiments, a modified HPV particle that can still package and deliver an agent does not have a modification at position $X_{16}$ of the L1 protein. For example, a modified HPV16 may have one or more changes at other positions but retains an asparagine (N) at position $X_{16}$.

It should be appreciated that major epitopes for neutralizing MAbs have been identified on one or more loops that differ between HPV serotypes. For example, for HPV11 in the DE loop, for HPV6 in the BC and EF loops and for HPV33 in the BC, DE, and FG loops, for HPV16 in the FG loop and for HPV31 in the EF loop (as described for example in Fleury et al. Prot. Sci. 2009). Using the strategy described herein one of ordinary skill may align sequences of other loops that have been shown to comprise major epitopes to generate additional modified VLPs.

It should also be appreciated, that any number of amino acid changes (mutations, deletions, additions) can be made at any amino acid position within the viral capsid protein (in one or more of the surface loops, at sites comprising amino acid with internally facing groups, or at any other position in the capsid protein) to modify or alter immunogenicity or for any other reason (e.g., to induce or prevent conformational changes, to increase or decrease charged amino acid groups, to alter targeting, to increase bioavailability, to induce specific modifications to increase uptake via a specific route of administration), maintaining the ability of the altered capsid protein to form VLPs and maintaining the ability of the resulting VLPs to transfer therapeutic agent(s) to the target cell.

It should further be appreciated that amino acid modifications can be introduced guided by what is taught herein and by what is known in the art about linear and conformational epitopes positioned within the loops. Conformational epitopes that may, for example, be sites of recognition for neutralizing antibodies, or may be sites important for cellular targeting or may aid cell entry by the VLP have been identified (as described for example in Fleury et al. Prot. Sci. 2009, and Sadeyen et al. Virology, 2002, 309:32-40, the contents of which are incorporated herein by reference in their entirety). Modification of one or more amino acids within the loops may be designed according to conformational epitopes and may comprise modification of one or more amino acids that are conserved in addition to those that are non-conserved.

In some embodiments, amino acid sequences may be inserted into the loops. For example, short amino acid sequences may be inserted into one or more surface-exposed loops. The short amino acid sequence inserts can be 4, 5, 6, 7, 8, 9, 10, 11, 12, 13, 14, 15, 16, 17, 18, 19, 20, 21, 22, 23, 24, 25, 30, 35, 40, 45, 50, 55, 60, 70, 80, 90, 100, 150, 200 or 250 amino acids long, or any length in between 4 amino acids and 250 amino acids. In certain embodiments, the inserts are between 4 and 50, 5 and 25, or 5 and 15 amino acids long. The inserts can be inserted anywhere in the loops. In some embodiments, the inserts are inserted approximately in the middle of a loop. It will be appreciated that if certain motifs are known to be presented by the a certain loop and it is desired to maintain the motif, the insertion will be made outside the motif, either N-terminal or C-terminal of the motif. On the other hand, if it is desired to disrupt a certain motif presented in a certain loop then the insertion will be made within the motif. The motif can be linear or structural, that is it may be based on the primary amino acid sequence or its secondary (or tertiary) structure. The motif can be a cellular recognition motif, that may facilitate VLP uptake and/or target cell recognition, or it may be an epitope that is recognized by certain antibodies or that is known to be antigenic. In some embodiments, where insertions are used to promote targeting or cellular uptake, the inserts may comprise, for example, viral targeting domains. It will be appreciated that these domains are not limited to HPV. Viral targeting domains may be derived from any virus to target any cell that is desired. The inserts may also comprise, for example, host-specific cellular recognition motifs, such as receptor recognition motifs. In some embodiments, insertions may comprise amino acid sequences that comprise epitopes for affinity tags, such as e.g., Strep Tag™ (STII, WSHPQFEK, SEQ ID NO: 12).

In some embodiments, insertions are used to stimulate an immune response. In these embodiments, the inserts may comprise one or more epitopes (e.g., a polytope) of viral origin (e.g., from various HPV serotypes). For example, a polytope may be constructed comprising antigenic regions (epitopes) of L1 protein of various HPV serotypes, e.g., HPV16, 18, 31, 33, and 45. In some embodiments, regions of the L2 protein may be inserted.

In some embodiments, insertions of one or more epitopes will generate an immune response in a subject to the one or more epitopes. In some embodiments, the immune response confers protection against re-infection with virus (e.g., HPV) and/or repopulation of virus (e.g., originated from the remaining virus after anti-viral treatment) and/or recurrence of a virus-associated cancer (e.g., originated from the remaining virally transformed cancer cells after anti-cancer treatment).

In some embodiments, peptides may be attached to the VLP surface to induce an altered or amplified immune response (e.g., if the peptide comprises one or more epitopes) or to alter or amplify targeting and/or cellular uptake of the VLP (e.g., if the peptide comprises one or more cellular receptors). For example, the VLP can have an albumin binding domain to enhance their transport through the blood vessels or a peptide to enhance transcytosis (e.g., an integrin-binding (RGD) motif that enhances basal-to-apical transcytosis; heparan sulfate moieties or other moieties) and/or a receptor-specific binding domain to enhance their uptake by the targeted cells (e.g., EGFR binding peptide), and/or peptides that enhance endosome and/or nuclear transport.

In some embodiments, the peptides can be attached through chemical cross-linking using a suitable linker, e.g., glutaraldehyde, imidoester, and BS(PEG)9, BS(PEG)5, DTSSP, EDC, SM(PEG)2, SMCC and sulfoSMCC (Thermo scientific).

In some embodiments, the peptides can be attached through affinity tags, such as StrepTag™.

In some embodiments the peptides are 10, 20, 30, 40, 50, 60, 70, 80, 90, 100, 150, 200, 250, 300, 350, 400, 450, or 500 amino acids long.

In certain embodiments, L1 protein and L1+ L2 protein may be produced recombinantly. In certain embodiments, recombinantly produced L1 protein and L1+L2 protein may self-assemble to form virus-like particles (VLPs). Recombinant production may occur in a bacterial, insect, yeast or mammalian host system. L1 protein may be expressed or L1+L2 protein may be co-expressed in the host system.

Methods for expressing and purifying L1 and L2 recombinant viral proteins in host systems, methods for disassembly and re-assembly of HPV nanoparticles or VLPs, and examples of modifications to the amino acid sequences of L1 and L2, administration of VLPs to subjects, and pharmaceutical compositions comprising VLPs are well known in the art and are taught herein. For example, U.S. Pat. Nos. 6,416,945; 6,991,795; and 7,205,126, incorporated herein by reference. It should be appreciated however, that the methods and modes provided herein are not limited to those described in the aforementioned U.S. patents. Other methods and modes known to those in the art may also be employed.

In certain embodiments, the HPV nanoparticles or VLPs are loaded with the one or more therapeutic agents. HPV nanoparticles may be loaded by dissembling and reassembling L1 or L1 and L2 viral particles, as described herein. Salts that are useful in aiding disassembly/reassembly of viral capsid proteins into VLPs, include Zn, Cu and Ni, Ru and Fe salts. Other methods of loading may be used as the invention is not limited in this respect. In some embodiments, HPV nanoparticles may be loaded with one or more therapeutic agents.

In some embodiments, HPV nanoparticles comprising L1 protein, or L1 and L2 protein, further comprise one or more therapeutic agents. In certain embodiments the therapeutic agent comprises one or more siRNA molecules or one or more nucleic acids (e.g., plasmid or other vector) that each is capable of expressing one or more siRNA molecules. In some embodiments, the therapeutic agent comprises one or more antisense nucleic acids (e.g., anti-E6 and/or anti-E7) one or more nucleic acids (e.g., plasmid or other vector) that each are capable of expressing one or more antisense nucleic acids. In some embodiments, the HPV nanoparticles comprise combinations of two or more therapeutic agents.

In some embodiments, the therapeutic agent is an inducer of RNA interference or other inducer of gene silencing. An inducer of RNA interference may be a siRNA, a shRNA, a hybrid nucleic acid molecule comprising a first part that comprises a duplex ribonucleic acid (RNA) molecule and a second part that comprises a single stranded deoxyribonucleic acid (DNA) molecule, a longer double-stranded RNA or a DNA construct for expression of siRNA or longer RNA sequences. Other inducers of gene silencing include inducers of DNA methylation, or ribozymes, or aptamers. In other embodiments, the therapeutic agent can be a modulator of gene expression such as a PNA (Peptide Nucleic Acid).

RNA interference RNA interference (RNAi) is a process whereby the introduction of double stranded RNA (dsRNA) into a cell inhibits gene expression post-translationally, in a sequence dependent fashion. RNAi can be mediated by short (for example 19-25 nucleotides) dsRNAs or small interfering RNAs' (siRNA). dsRNA is cleaved in the cell to create siRNAs that are incorporated into an RNA-induced silencing complex (RISC), guiding the complex to a homologous endogenous mRNA, cleaving the mRNA transcript, and resulting in the destruction of the mRNA.

To induce RNA interference in a cell, dsRNA may be introduced into the cell as an isolated nucleic acid fragment or via a transgene, plasmid, or virus. In certain embodiments, VLPs are used to deliver dsRNA to the target cells.

In some embodiments, a short hairpin RNA molecule (shRNA) is expressed in the cell. A shRNA comprises short inverted repeats separated by a small loop sequence. One inverted repeat is complimentary to the gene target. The shRNA is then processed into an siRNA which degrades the target gene mRNA. shRNAs can produced within a cell with a DNA construct encoding the shRNA sequence under control of a RNA polymerase III promoter, such as the human H1 or 7SK promoter. Alternatively, the shRNA may be synthesized exogenously and introduced directly into the cell, for example through VLP delivery. In certain embodiments, the shRNA sequence is between 40 and 100 bases in length or between 40 and 70 bases in length. The stem of the hairpin are, for example, between 19 and 30 base pairs in length. The stem may contain G-U pairings to stabilize the hairpin structure.

siRNA sequences are selected on the basis of their homology to the target gene. Homology between two nucleotide sequences may be determined using a variety of programs including the BLAST program (Altschul et al. (1990) J. Mol. Biol. 215: 403-10), or BestFit (Genetics Computer Group, 575 Science Drive, Madison, Wis., USA, Wisconsin 53711). Sequence comparisons may be made using FASTA and FASTP (see Pearson & Lipman, 1988. Methods in Enzymology 183: 63-98). Tools for design and quality of siRNAs, shRNAs and/or miRNAs are known in the art. Web-based online software system for designing siRNA sequences and scrambled siRNA sequences are for example siDirect, siSearch, SEQ2SVM, Deqor, siRNA Wizard (InvivoGen). The specificity can be predicted using for example SpecificityServer, miRacle. Target sequences can be researched for example at HuSiDa (Human siRNA Database), and siRNAdb (a database of siRNA sequences). Sequence comparison may be made over the full length of the relevant sequence, or may more preferably be over a contiguous sequence of about or 10, 15, 20, 25 or 30 bases. In certain embodiments, the degree of homology between the siRNA and the target gene is at least 75%, at least 80%, at least 85%, at least 90%, at least 95%, at least 97%, or at least 99%, or 100%. The siRNA may be between 10 bp and 30 bp in length, or between 20 bp and 25 bp, or the siRNA is 20, 21 or 22 bp in length.

The occurrence of RNAi can be detected by transfecting cultured cells with the siRNA, followed by RT-PCR of the mRNA of interest. Where RNAi is induced by the siRNA, levels of the mRNA of interest will be reduced in transfected cells as compared to control cells. A reduction in protein production can be confirmed by Western blotting of cell lysates followed by probing with an antibody reactive to the protein of interest.

In some embodiments, the gene to be silenced is an HPV E6 or E7 gene. The siRNA sequence may be any contiguous sequence of 10-30 bp from any one of the E6 or E7 gene sequences, e.g., those of HPV16 or HPV18, that induces RNAi. Alternatively, longer dsRNA fragments comprising contiguous sequences from these sequences may be used, as they will be cleaved to form siRNAs within the cell.

siRNA molecules may be synthesized using standard solid or solution phase synthesis techniques which are known in the art. Synthetic siRNAs against mRNAs encoding HPV-16 E6 and HPV-18 E6, respectively, can be obtained commercially (for example, from Dharmacon Research, Lafayette, USA).

In some embodiments, the siRNA has an overhang at one or both ends of one or more deoxythymidine bases to increase the stability of the siRNA within cells by reducing its susceptibility to degradation by nucleases.

In some embodiments, the siRNA is a hybrid nucleic acid molecule comprising a first part that comprises a duplex ribonucleic acid (RNA) molecule and a second part that comprises a single stranded deoxyribonucleic acid (DNA) molecule.

Linkages between nucleotides may be phosphodiester bonds or alternatives, for example, linking groups of the formula P(O)S, (thioate); P(S)S, (dithioate); P(O)NR'2; P(O)R'; P(O)OR6; CO; or CONR'2 wherein R is H (or a salt) or alkyl (1-12C) and R6 is alkyl (1-9C) is joined to adjacent nucleotides through —O— or —S—.

Modified nucleotide bases can be used in addition to the naturally occurring bases. For example, modified bases may increase the stability of the siRNA molecule, thereby reducing the amount required for silencing. The term modified nucleotide base encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-0-methyl-; 2-0-alkyl; 2-0-allyl; 2'-S-alkyl; 2'-S-allyl; 2'-fluoro-; 2'-halo or 2; azido-ribose, carbocyclic sugar analogues a-anomeric sugars; epimeric sugars such as arabinose, xyloses or lyxoses, pyranose sugars, furanose sugars, and sedoheptulose.

Modified nucleotides are known in the art and include alkylated purines and pyrimidines, acylated purines and pyrimidines, and other heterocycles. These classes of pyrimidines and purines are known in the art and include pseudoisocytosine, N4, N4-ethanocytosine, 8-hydroxy-N-6-methyladenine, 4-acetylcytosine, 5-(carboxyhydroxylmethyl) uracil, 5 fluorouracil, 5-bromouracil, 5-carboxymethylaminomethyl-2-thiouracil, 5-carboxymethylaminomethyl uracil, dihydrouracil, inosine, N6-isopentyl-adenine, 1-methyladenine, 1-methylpseudouracil, 1-methylguanine, 2,2-dimethylguanine, 2-methyladenine, 2-methylguanine, 3-methylcytosine, 5-methylcytosine, N6-methyladenine, 7-methylguanine, 5-methylaminomethyl uracil, 5-methoxy amino methyl-2-thiouracil, -D-mannosylqueosine, 5-methoxycarbonylmethyluracil, 5-methoxyuracil, 2 methylthio-N-6-isopentenyladenine, uracil-5-oxyacetic acid methyl ester, psueouracil, 2-thiocytosine, 5-methyl-2 thiouracil, 2-thiouracil, 4-thiouracil, 5-methyluracil, N-uracil-5-oxyacetic acid methylester, uracil 5-oxyacetic acid, queosine, 2-thiocytosine, 5-propyluracil, 5-propylcytosine, 5-ethyluracil, 5-ethylcytosine, 5-butyluracil, 5-pentyluracil, 5-pentylcytosine, and 2,6, diaminopurine, methylpsuedouracil, 1-methylguanine, 1-methylcytosine.

In some embodiments, siRNA molecules or longer dsRNA molecules may be made recombinantly by transcription of a nucleic acid sequence, for example contained within a vector as described herein. The vector may be any RNA or DNA vector.

The vector can be an expression vector, wherein the nucleotide sequence is operably linked to a promoter compatible with the cell. Promoters suitable for use in various vertebrate systems are well known in the art. For example, suitable promoters include viral promoters such as mammalian retrovirus or DNA virus promoters, e.g. MLV, CMV, RSV, SV40 IEP (immediate early promoter) and adenovirus promoters and metallothionein promoter. Strong mammalian promoters may also be used. It will be appreciated that variants of such promoters retaining substantially similar transcriptional activities may also be used.

In some embodiments, the vector may have at least two promoters, one to direct expression of the sense strand and one to direct expression of the antisense strand of the dsRNA. In other embodiments, two vectors may be used, one for the sense strand and one for the antisense strand. Alternatively the vector may encode RNAs which form stem-loop structures which are subsequently cleaved by the cell to produce dsRNA.

The nucleic acid construct may contain a specific cellular, viral or other promoter or repressor of gene expression. The promoter or repressor may be designed to reflect the context of the cell into which the construct is introduced. For example, the construct may contain a viral promoter so expression from the construct is dependent upon the presence of a viral protein, so that the construct is expressed only in viral-infected cells. Similarly, the construct may have a promoter or repressor specific to certain cell types or to certain developmental stages. For example, where the vector is for use in virally infected cell such as cells infected with HPV, a viral promoter which matches the disease-causing virus should be used, e.g. a HPV promoter (such as the promoter causing expression of HPV16 E6/E7) for HPV-infected cells. In such embodiments, the vector will only be expressed in the virally-infected cells.

In certain embodiments, the siRNA therapeutic agent is targeted against agents that promote or mediate the cell death or the apoptosis of the target cell. In certain embodiments, the siRNA therapeutic agent is targeted against HPV viral proteins. In some embodiments, the viral proteins that are targeted by siRNA molecules are viral E6 and/or E7. E6 siRNA has been found to be potent in the suppression of viral oncogene expression, and E6 siRNA exhibits a potent growth inhibitory activity (Yoshinouchi et al, 2003). E7 silencing produced by siRNA induces apoptotitc cell death. Without wanting to be bound by any particular theory, it has been described that synthetic small interfering (si)RNAs, specifically directed against the antiapoptotic HPV E7 oncogene, restore dormant tumor suppressor pathways in HPV-positive cancer cells that are otherwise inactive in the presence of E7 leading to apoptosis and cell death. In some embodiments, silencing of E7 by siRNA may be sufficient to lead to apoptosis of infected host cell, without the need to inhibit E6. (Milner et al.). siRNAs for viral E6 and E7 are described, for example in Butz et al. (Oncogene (2003) 22, 5938-5945) and Milner et al. (Patent application 0117359.0 and 0216929.0 and WO 2005/051431), incorporated by reference herein.

In certain embodiments, HPV-16 E6 and HPV-18 E6 can be specifically targeted by siRNA. In certain embodiments, the respective target sequence for

```
                           (SEQ ID NO: 13, nucleotides 377-395)
    HPV-16 E6 is 5' -UACAACAAACCGUUGUGUG.
```

In certain embodiments, the respective target sequence for

```
                           (SEQ ID NO: 14, nucleotides 381-399)
    HPV-18 E6 is 5' -CUAACUAACACUGGGUUAU
       (as described in Butz et al.).
```

In other embodiments, E6 and E7 siRNA constructs are:

```
                                        (SEQ ID NO: 15)
    E6 (forward):    5' GAGGUAUAUGACUUUGCUUTT;

(SEQ ID NO: 16)
    E6 (reverse):    TTCUCCAUAUACUGAAACGAA 5'
    and (SEQ ID NO: 17)
    E7 (forward):    5' AGGAGGAUGAAAUAGAUGGTT;

(SEQ ID NO: 18)
    E7 (reverse):    TTCCUCCUACUUUAUCUACC 5'
    (as described in Milner, WO 2005/051431).
```

In other embodiments, E6 and E7 shRNA constructs are:

TABLE 3

| shRNA | | Oligonucleotides sequences (5'-3') |
|---|---|---|
| Control | Forward | CACCAGAGTTCAAAAGCCCTTCATCGAAATGAAGGGCTTTTGAACTC (SEQ ID NO: 19) |
| | Reverse | AAAAAGAGTTCAAAAGCCCTTCATTTCGATGAAGGGCTTTTGAACTC (SEQ ID NO: 20) |
| LacZ | Forward | CACCGCTACACAAATCAGCGATTTCGAAAAATCGCTGATTTGTGTAG (SEQ ID NO: 21) |
| | Reverse | AAAACTACACAAATCAGCGATTTTTCGAAATCGCTGATTTGTGTAGC (SEQ ID NO: 22) |
| shE7-1 | Forward | CACCAGGAGGATGAAATAGATGGTTCGAAAACCATCTATTTCATCCTCC (SEQ ID NO: 23) |
| | Reverse | AAAAGGAGGATGAAATAGATGGTTTTCGAACCATCTATTTCATCCTCCT (SEQ ID NO: 24) |
| shE7-2 | Forward | CACCGCCCATTACAATATTGTAACCCGAAGGTTACAATATTGTAATGGGC (SEQ ID NO: 25) |
| | Reverse | AAAAGCCCATTACAATATTGTAACCTTCGGGTTACAATATTGTAATGGGC (SEQ ID NO: 26) |
| shE6-1 | Forward | CAACGAGGTATATGACTTTGCTTTTCGAAAAAAGCAAAGTCATATACCTC (SEQ ID NO: 27) |
| | Reverse | AAAAGAGGTATATGACTTTGCTTTTTTCGAAAAGCAAAGTCATATACCTC (SEQ ID NO: 28) |
| shE6-2 | Forward | CACCGGTCGATGTATGTCTTGTTGCCGAAGCAACAAGACATACATCGACC (SEQ ID NO: 29) |
| | Reverse | AAAAGGTCGATGTATGTCTTCTTGCTTCGGCAACAAGACATACATCGACC (SEQ ID NO: 30) |

(as described in Bousarghin et al, Mol Cancer Ther, 2009, 8: 357-365, incorporated by reference herein).

In certain embodiments, amino acids of the viral wild-type proteins, such as L1 and/or L1+ L2, assembling into the HPV nanoparticles are mutated and/or substituted and/or deleted. In certain embodiments, these amino acid are modified to enhance the positive charge of the VLP interior. In certain embodiments, modifications are introduced to allow a stronger electrostatic interaction of the siRNA molecule with one or more of the amino acids facing the interior of the VLP and/or to avoid leakage of the siRNA out of the HPV nanoparticle.

Nucleic acids are highly charged and do not cross cell membranes by free diffusion. Additionally, the hydrophilic character and anionic backbone of siRNAs reduces their uptake by the cells. In certain embodiments, therapeutic anti-viral siRNA may be delivered to a subject administering HPV nanoparticles to increase cellular uptake (traverse biological membrane barriers in vivo) and/or bioavailability of the siRNA.

It should be appreciated that VLP compositions comprising agents that promote apoptosis in HPV-infected cells only are particularly useful in some embodiments, because they target cells that are infected by HPV (e.g., the VLP surface components target the same cell type that is targeted by naturally infective HPV) and deliver agents that kill the HPV-infected cells. These compositions can be used to cure HPV infections in some embodiments. In some embodiments, chronic treatment is not required provided that suitable dosages (e.g., single dosages or a course of treatment over a predetermined treatment period, but not chronic) are used to kill the HPV-infected cells. However, in some embodiments, compositions of the invention may not be sufficient to kill all HPV-infected cells and more that one course of treatment and/or chronic treatment is required. In some embodiments, VLP compositions comprising anti-viral agents (as opposed to pro-apoptotic agents) may be used for chronic treatments.

In certain embodiments, the therapeutic agent is an anti-cancer agent. In a preferred embodiment, the anticancer agent is Gemcitabine.

In certain embodiments, the therapeutic agent is a chemotherapeutic agent, for instance, methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, IncelNX-710, VX-853, ZD0101, IS1641, ODN 698, TA 2516/Marmistat, BB2516/Marmistat, CDP 845, D2163, PD183805, DX8951f, Lemonal DP 2202, FK 317, Picibanil/OK-432, AD 32Nalrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/

776C85/5FU enhancer, Campto/Levamisole, Camptosar/ Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/ Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/ Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2' deoxycoformycin), Semustine (methyl-CCNU), Teniposide (VM-26) or Vindesine sulfate, but it is not so limited.

In certain embodiments, the therapeutic agent is an immunotherapeutic agent, for instance, Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART1D10 Ab, SMART ABL 364 Ab or ImmuRAIT-CEA, but it is not so limited.

In certain embodiments, the therapeutic agent is an anti-viral agent. Examples of anti-viral agents are: Polysulfates (PVAS), Polysulfonates (PVS), Polycarboxylates, Polyoxometalates, Chicoric acid, zintevir, cosalane derivatives, Bicyclams (i.e., AMD3100), T-22, T-134, ALX-40-4C, CGP-64222, TAK-779, AZT (azidothymidine), ddI, ddC, d4T (didehydrodideoxythymidine), 3TC (3'-thiadideoxycytidine), ABC, and other ddN (2',3'-dideoxynucleoside) analogs, Nevirapine, delavirdine, efavirenz, emivirine (MKC-442), capravirine, thiocarboxanilide UC-781, acyclovir, valaciclovir, penciclovir, famciclovir, bromovinyldeoxyuridine (BVDU, brivudin), Cidofovir, Adefovir dipivoxil, Tenofovir disoproxil, Ribavirin, valacyclovir, gancyclovir, formivirsen, foscarnet, EICAR (5-ethynyl-1-β-D-ribofuranosylimidazole-4-carboxamide), Mycophenolic acid, Neplanocin A, 3-deazaneplanocin A, 6'-C-methylneplanocin A, DHCeA (9-(trans-2',trans-3'-dihydroxycyclopent-4'-enyl) adenine), or c³DHCeA (9-(trans-2',trans-3'-dihydroxycyclopent-4'-enyl)-3-deazaadenine), as described, for example, in De Clercq J Pharmacol Exp Ther 2001, 297: 1-10, incorporated by reference herein, but it is not so limited.

In some embodiments, RNAi treatment as described herein further comprises treatment with Cidofovir. Cidofovir is an antiviral drug used to treat, for example, HPV-induced laryngeal papillomatosis. Cidofovir also has activity in cervical carcinoma cells. Cidofovir may be administered prior, concurrently or after VLP-based RNAi treatment (e.g., E6 or E7-specific siRNA or shRNA). In some embodiments, Cidofovir is administered concurrently with the RNAi molecule and is delivered by the VLPs described herein.

Additional therapeutic agents are, for example, signal transduction inhibitors for example inhibitors of Serine-Threonin kinases, inhibitors of Ras/MAPK, inhibitors of the Insulin Growth Factor Receptor, inhibitors of EGFR and/or PDGFR, antiangiongenic agents like inhibitors of VEGF and/or VEGFR, PARP modulators and inhibitors, inhibitors of the Hedgehog pathway, agents related with the inhibition of the metabolic pathways, beta-interferon, TDF, or cPrPMEDAP.

In certain embodiments, HPV nanoparticles comprising one or more therapeutic agents, are administered to a subject infected with HPV in an amount sufficient to treat the subject. In certain embodiments treatment of a subject having HPV infection with HPV nanoparticles comprising one or more therapeutic agents further comprises administration of an anticancer and/or antiviral agent. These agents may be co-administered at the same time or at a different time, for example before or after administration of HPV nanoparticles comprising one or more therapeutic agents.

In certain embodiments, HPV nanoparticles comprising one or more therapeutic agents are administered to a subject infected with HPV topically. Topical administration may include administering the HPV nanoparticles comprising one or more therapeutic agents in form of a suitable pharmaceutical composition or formulation. In certain embodiments, the pharmaceutical composition or formulation suitable for topical administration may be a gel or cream. The gel or cream may be applied, in certain embodiments, to mucosal membranes.

In certain embodiments, HPV nanoparticles comprising one or more therapeutic agents are administered to epithelial tissues with mucosal surfaces, for example for the treatment cervical or colorectal carcinomas. In these embodiments, the pharmaceutical composition comprising HPV nanoparticles further comprises a mucoadhesive substance, such as a polymer. A mucoadhesive substance is any formulation that adheres to a mucosal surface lining a body cavity or surface including the lumenal surface of the gastro-intestinal epithelium, of the colorectal epithelium and of the cervix. Mucosal epithelial cell layers are rich in a viscous secretion (mucus). Mucoadhesive polymers have the ability to adhere to humid or to wet mucosal tissue surfaces such as those of the colorectal epithelium or of the cervical epithelium.

Many polymers can be utilized to form gels, creams or other adhesive substances, for example, a gel, such as a hydrogel, organogel or thermoreversible gel. Other useful polymer types include, but are not limited to, thermoplastics and films. The polymer may be, for example, poly (ethylene oxide), poly (ethylene glycol), poly (vinyl alcohol), poly (vinyl pyrrolidine), poly (acrylic acid), poly (hydroxy ethyl methacrylate), hydroxyethyl ethyl cellulose, hydroxy ethyl cellulose and chitosan and mixtures thereof, polysaccharides (agar) or carboxymethylcellulose. In some embodiments, the gels, creams or other adhesive substances may contain other materials which provide a mucoadhesive effect. Such materials include titanium dioxide, silicon dioxide, and clays.

The pharmaceutical composition may be applied directly, for example as a gel, or it may be comprised within a pre-assembled patch or other device which enables apposition of the gel with the tissues or cells to be targeted (as described, for example, in Milner et al. WO 2005/051431). For example, a patch comprising a bioadhesive layer or mucoadhesive layer attached to a backing layer (for example comprising poly (vinyl chloride) or hydroxypropylcellulose) of suitable pliability to conform with the tissue architecture of the surface of the cervix could be employed for therapeutic delivery of the HPV nanoparticles comprising the therapeutic agents and optionally additional therapeutic agents (such as anti-cancer and/or anti-viral agents) to cervical tissues. The physical properties of the patch should ideally be retained over several hours to one or more days without discomfort to the patient and without displacement of the patch during normal body movements.

In some embodiments, the HPV nanoparticle comprising one or more therapeutic agents can be provided in the form of a gel such as preparation of propylene glycol methyl cellulose for application to a target area in which it is desired to focus. The gels may be provided in a tube, such as 50 mg of the active ingredient suspended in the gel. These gels are particularly convenient for application to the skin or other epithelial surface (for example the cervical or anogenital area).

In some embodiments the gel is dispensed from an elongated applicator tube (such as a rectal or vaginal applicator), for example to apply it rectally or intravaginally. However, it should be appreciated that a composition of the invention may be administered in any suitable form to reach HPV infected cells or other target cells, as the invention is not limited in this respect. For example, compositions of the invention may be provided in the form of suppositories, capsules, creams, gels, foams, sprays, aerosols, and/or on the surface of or impregnated within material that can be contacted to a target region (e.g., oral, throat, cervical, vaginal, anal, etc.) or any combination of two or more thereof.

In some embodiments, the HPV nanoparticle comprising one or more therapeutic agents can also be applied as a cream or simple crystals or a pellet that can be applied on to or inserted into the epithelial surface or the skin with a 16-gauge trochar needle for short-term treatments.

It should be appreciated that compositions of the invention may be administered to a subject infected with HPV (e.g., a subject diagnosed or known to have a persistent high-risk HPV infection) in order to treat a dysplasia or a cancer and/or prevent the development of a dysplasia or a cancer or other condition associated with HPV infection. However, in some embodiments, compositions of the invention may be administered (e.g., prophylactically) to a subject with a persistent high-risk HPV infection who is suspected of being at risk of being infected with another serotype of high-risk HPV infection.

Where a composition as described herein is to be administered to an individual, administration is in a "prophylactically effective amount" or a "therapeutically effective amount." The final composition is administered as needed, which will depend on the disease to be treated and the size of the affected area. Administration may be, for example, daily, weekly or monthly.

The term "effective amount" of a composition refers to the amount necessary or sufficient for a composition alone, or together with further doses, to realize a desired biologic effect. The desired response, of course, will depend on the particular condition being treated. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or adverse condition being treated, the size of the subject, or the severity of the disease or adverse condition. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons. One of ordinary skill in the art can empirically determine the effective amount without necessitating undue experimentation.

For any compound described herein the therapeutically effective amount can be initially determined from animal models. A therapeutically effective dose can also be determined from data for compounds which are known to exhibit similar pharmacological activities, such as other nanoparticles. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

In certain embodiments, methods for treating a subject are provided. The subject may be any mammal. As used herein, the terms "treat," "treated," or "treating" when used with respect to an adverse condition, such as a disorder or disease, for example, a cancer, dysplasia or neoplasm refers to a prophylactic treatment which increases the resistance of a subject to development of the adverse condition, or, in other words, decreases the likelihood that the subject will develop the adverse condition, as well as a treatment after the subject has developed the adverse condition in order to fight the disease, or prevent the adverse condition from becoming worse.

In certain embodiments, the methods for treatment described herein are suitable for any HPV-infected subjects. In certain embodiments, methods are provided for the treatment of genital warts and/or verruca vulgaris. In certain embodiments, methods are provided for the treatment of early stage dysplasia, CIN (II, III) and/of\r carcinoma in situ. In certain embodiments, methods are provided for the treatment of cervical cancer and all other HPV related neoplasias, such as, for example, labial cancer, penile cancer, oral squamous cell carcinoma, head and neck cancer, or non-melanoma skin cancer. In some embodiments, methods are provided for the treatment of infections concomitant to HPV infection, for example Herpes Simplex Virus infection. In some embodiments, the subject is a human. In certain embodiments, the subject is female.

Similarly, aspects of the invention relate to treating infections of one or more of these tissues (e.g., labial, penile, oral, vaginal, cervical, skin or other tissue infections).

In certain embodiments, HPV nanoparticles comprising L1 or L1 and L2 and further comprising one or more therapeutic agents may target HPV-infected cells in an HPV-infected subject that have the potential to become cancer cells. In certain embodiments, HPV nanoparticles comprising L1 or L1 and L2 and further comprising one or more therapeutic agents may target HPV-infected cells in an HPV-infected subject that are cancer cells.

In certain embodiments, administering HPV nanoparticles comprising one or more therapeutic agents to a subject infected with HPV kills HPV-infected cancer cells in the subject. In certain embodiments, administering HPV nanoparticles comprising one or more therapeutic agents to a subject infected with HPV causes apoptosis in the HPV-infected cancer cells in the subject.

Cervical cancer usually develops slowly over time. Before cancer appears in the cervix, the cells of the cervix go through changes known as dysplasia, in which cells that are not normal begin to appear in the cervical tissue. Later, cancer cells start to grow and spread more deeply into the cervix and to surrounding areas.

Methods are provided for treating a subject in need of treatment. Subjects in need of treatment are preferably subjects that have HPV infection. In some embodiments, the subjects are in an early stage of infection. In some embodiments, the subjects present early stage cervical dysplasia. In some embodiments, the subjects present CIN. In some embodiments, the subjects present cervical carcinoma.

In some embodiments, the methods comprise administering an HPV nanoparticle comprising L1 or L1 and L2 and further comprising one or more therapeutic agents to a HPV-infected subject in an amount sufficient to treat the HPV infection. In certain embodiments, the HPV nanoparticle is administered topically to a mucosal membrane. In certain embodiments, the methods further comprise administering anti-cancer and/or antiviral agents. In some embodiments, the one or more therapeutic agents are siRNA molecules or siRNA encoding molecules. In certain embodiments the siRNA is directed against viral E6 and/or E7. In some embodiments, the anti-cancer agent is Gemcitabine.

In some embodiments, the VLPs may be used to deliver anti-cancer agents to a subject having cancer.

In certain embodiments, the HPV nanoparticle comprising one or more therapeutic agents can be applied topically to or adjacent to an epithelium such as the cervical epithelial or topically to or adjacent to an epithelial lesion such as cervical or anal epithelial carcinoma. In some embodiments, the one or more therapeutic agents are siRNA molecules or siRNA encoding molecules.

In some embodiments, the HPV nanoparticle comprising one or more therapeutic agents is placed in a topical preparation for application to an epithelial surface, for example by application to malignant epithelium, such as a urogenital neoplasm, such as anal, vaginal or cervical neoplasm, such as cervical CIN.

In some embodiments, the HPV nanoparticle comprising one or more therapeutic agents is prepared in a topical preparation for application to the epidermis, for example for treatment of non-melanoma skin cancer.

In some embodiments, the one or more therapeutic agents are siRNA molecules or siRNA encoding molecules.

In some embodiments, one or more HPV compositions or methods of the invention may be used in conjunction with a current treatment for HPV infection and/or cervical cancer. For example, treatment methods and/or compositions of the invention may be used before and/or after one of the treatment techniques outlined in Table 4.

Table 4 outlines common techniques currently used for treatment of CIN.

| Technique | Description | Advantage | Disadvantage |
|---|---|---|---|
| Cryotherapy | Application of a super-cooled probe (nitrous oxide or carbon dioxide) directly to the cervical lesion using one or more cooling and thawing cycles. | Ease of use, low cost, and a low complication rate. | Invasive. Evocation of a copious vaginal discharge lasting for weeks, a lack of tissue for histology, and the use of a probe which is not easily adjusted to the dimensions of the lesion and cervix. |
| $CO_2$ laser ablation | Tissue is vaporized to a depth of at least 7 mm to assure that the bases of the deepest glands are destroyed. | Precise and flexible. | Invasive. Mild cramps and post-treatment vaginal discharge lasting one to two weeks. The technique is expensive, requires significant training and attention to safety issues, and precludes detection of occult invasion through histologic evaluation. |
| Excisional (cold knife) conization | Excision of a cone shaped portion of the cervix using a scalpel | Results in a specimen devoid of thermal marginal artifacts that might complicate the histologic assessment of specimens derived by laser or electrosurgical excision techniques. Important for lesions extending into the endocervical canal and suspected adenocarcinoma in situ. | Invasive. The need for general anesthesia and a higher rate of post surgical complications (e.g., bleeding, infection, cervical stenosis, cervical incompetence). |
| Loop electrosurgical excision procedure (LEEP) | Uses a wire loop through which an electrical current is passed at variable power settings. The geometrical shape of the excised specimen is determined by the shape of the loop, which can be tailored to fit the lesion. | The approach of choice for treating CIN II and III because of its ease of use, low cost, and high rate of success. It can be performed readily in the office setting using local anesthesia. | Invasive. May lead to infection and hemorrhage. Damage to the cervical stroma may lead to cervical stenosis or incompetence. The LEEP technique results in some thermal artifact in all specimens excised, although this generally does not preclude histologic evaluation. |

These treatments have varying efficacy rates ranging from 60-90%. However, all of these treatments are invasive procedures that remove or destroy cervical tissue and are often associated with complications.

The pathogenesis of cervical cancer is tightly linked to persistent Human Papilloma Virus infection (reviewed in zur Hausen et al 2002). Papillomaviruses are small non-enveloped DNA viruses and their icosahedral capsid is constituted of L1 and L2 proteins, which encapsidate a closed circular, double-stranded DNA of about 8 kbp. The viral capsid of 50-60 nm in diameter contains 72 pentamers of L1 major protein and 12 to 72 copies of L2 minor capsid protein.

A subgroup of 15 HPVs including types 16, 18, 31, 33, 35, 39, 45, 51, 52, 56, 58, 59, 68, and HPV-69 has been designated high risk. High-risk HPV genes are found in almost 100% of cervical cancer tissue samples (Walboomers et al., 1999). Integration of the viral genome and subsequent expression of two main viral oncogenes, E6 and E7, are considered to be critical steps in the development of this particular cancer. E6 binds to p53 tumor suppressor protein and targets it for ubiquitin-mediated degradation (Munger and Howley, 2002). p53 orchestrates the cellular response to various stress stimuli, for example genotoxic damage by ionizing radiation or chemotherapy drugs. Depending on how extensive the damage is, activation of p53 may result in cell cycle arrest, activation of the DNA repair machinery or apoptosis (Vousden and Lu, 2002). Nonfunctional or absent p53 allows accelerated cell division rate and promotes genetic instability, facilitating malignant transformation (Attardi, 2005). Constant expression of E6 and E7 mRNA by high-risk human papillomaviruses (HPV) abrogates p53 and pRb function, respectively, and is essential for the development of cervical cancer.

Additionally HPV 16 is associated with a small subset of head and neck tumors, mainly of the tissue of the Waldeyer ring. It has been demonstrated that a spectrum of HPV types, including low-risk HPV types are present in malignant lesions of other sites of the head and neck, including oral cancers, as well as esophageal cancers (de Villers et al).

Non-melanoma skin cancer (basal and squamous cell carcinomas) is by far the most frequent cancer among the Caucasian population worldwide. These cancers occur mainly on sun-exposed sites pointing to UV irradiation as a major environmental factor in the pathogenesis of this disease. Several genetic changes have in addition been associated, including mutations in the cellular gene p53. Several HPV types in the genus Beta-papillomavirus seem to be associated with squamous cell carcinoma of the skin. This include cutaneous HPV types (HPV 20, HPV 38 and HPV 27) which are either activated or suppressed by UV.

Accordingly, aspects of the invention may be used to treat conditions other than cervical cancer associated with HPV infection. For example, aspects of the invention may be used to treat head and neck cancers (e.g., oral and/or esophageal cancers) associated with HPV infection. However, it should be appreciated that HPV-based particles of the invention may be used as general delivery vehicles to treat mucosal diseases or conditions regardless of whether they are caused by HPV infection. Accordingly, methods and compositions of the invention may be used to treat other infections such as HSV or HIV infection, and/or for example, bacterial infections such as *Gardnerella vaginalis, Neisseria gonorrhoeae*; fungus infection such as *Candida Albicans* infections, or parasite infections such as the parasite *Trichomonas vaginalis*, or other infections which are common infections in the genital tract.

In some embodiments, an HPV nanoparticle comprising one or more therapeutic agents can be used to treat persistent high-risk HPV infection, cervical dysplasia, precancerous lesions CIN I, II, III (CIN2/3, VIN2/3) and/or carcinoma in situ.

In some embodiments, an HPV nanoparticle comprising one or more therapeutic agents can be used to treat genital warts, non melanoma skin cancer, head and neck cancer, oropharyngeal cancer, vulval cancer, vaginal cancer, penile cancer, and/or anal cancer.

Compositions of the invention may be administered to female or male subjects depending on the site of treatment.

In some embodiments, compositions comprising HPV-based VLP may be used for delivery of therapeutic agents to epithelial cells, for example to the skin. In some embodiments, the compositions may be administered to treat infections of the epidermis caused by gram-positive bacteria which include, for example, *Staphylococcus, Micrococcus*, and *Corynebacterium* sp., *Staphylococcus aureus*, and *Streptococcus pyogenes*, causing, for example, skin diseases, such as impetigo and eethyma. In some embodiments, compositions comprising HPV-based VLP may be used to treat non-melanoma skin cancer.

In some embodiments, modified HPV particles, as described herein, comprising one or more therapeutic agents may be administered systemically, (e.g., i.v.) for the treatment of tumors, e.g., ovarian cancer, breast cancer, oral squamous cell carcinoma, head and neck cancer, NSCLC, SCLC, bladder cancer, or prostate cancer. In some embodiments, cancer cells disply receptors for HPV VLPs and modified HPV particles, as described herein, can be used to target these cancer cells. In some embodiments, modified HPV particles may additionally be altered to display targeting agents that are specific for a cancer cell.

Aspects of the invention are not limited in its application to the details of construction and the arrangement of components set forth in the preceding description or illustrated in the examples or in the drawings. Aspects of the invention are capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Example 1

Inhibition of Cervical Cancer Cell Growth by HPV-VLPs Packaged with HPV Oncoprotein shRNAs The main aims of this study were to construct an HPV based shRNA expression system and to explore HPV mediated RNA interference for effective E6 and E7 gene silencing. We show here that HPV pseudovirions expressing E6 and E7 shRNA in cervical cancer cells resulted in the depletion of E6 and E7 expression and suppression of cancer cell growth, suggesting that HPV VLP are valuable to deliver plasmids encoding shRNA for the treatment of cervical cancer.

Materials and Methods

Cell Lines, Cell Culture, and Cell Transfection

The human cervical carcinoma cell lines CaSki (ATCC CRL-150) and C33-A (ATCC HTB-31; American Type Culture Collection) were grown at 37° C. in a humidified atmosphere with 5% $CO_2$ in DMEM supplemented with 10% FCS (Invitrogen), 1% penicillin/streptomycin, and 1% sodium pyruvate. CaSki cells were infected by HPV-16 and express E6 and E7, whereas C33-A cells were negative for HPV. Murine cell line TC1 (ATCC CRL-2785) was cotransformed by HPV-16 E6/E7 oncoproteins and c-Has-Ras. These cells were grown in RPMI 1640 with 10 mmol/L of HEPES, 1 mmol/L of sodium pyruvate supplemented with 2 mmol/L of nonessential amino acids and 10% FCS. Murine 293FT cells (Invitrogen) were derived from the 293T cell line (ATCC CRL 11268). They express the SV40 large T antigen and were cultured in the presence of 500 µg/mL of geneticin (Invitrogen).

One day before transfection, cells were trypsinized and seeded into six-well plates. Cells were then transfected with plasmids encoding shRNA using Lipofectamine 2000 (Invitrogen), HPV-31 pseudovirions, or lentivirus coding for shRNA. Cells were harvested for analysis at various times as indicated in the results.

Design and Production of Plasmids Expressing E6- and E7-Specific shRNA

In order to produce the pENTR/U6 entry clone, the BLOCK-iT U6 entry vector was used. We first designed and synthesized complementary DNA oligos (Invitrogen), each containing four nucleotide overhangs necessary for directional cloning. Complementary sequences of shRNA corresponding to E6 and E7 siRNA are described in FIG. 1B. E6-2 and E7-2 sequences were selected using the "shRNA designer" software from Invitrogen. E6-1 and E7-1 sequences were those described by Jiang and Milner (Oncogene 2002; 21:6041-8). We used LacZ and the control shRNA sequence described by Jiang and Milner (Oncogene 2002; 21:6041-8) as controls. All sequences were BLAST-confirmed for specificity.

Equal amounts of the forward and reverse strand oligos were annealed to generate the double-stranded oligos by incubation in annealing buffer at 95° C. for 4 min. After generating double-stranded oligos, they were ligated into the pENTER/U6 vector (Invitrogen). The plasmids were sequenced, propagated, and purified using the Qiagen plasmid midi kit (Qiagen, France). Entry clones were used for transient RNA interference analysis.

Production of E6 and E7 sh RNA-Expressing HPV Pseudovirions HPV-31

VLPs were expressed in Sf21 cells infected with a recombinant baculovirus encoding codon-optimized HPV-31 L1 and L2 genes (Fleury et al., Clin Vaccine Immunol 2008; 15:172-5). Cells were incubated at 27° C. for 72 h (Touze et al., Nucleic Acids Res 1998; 26:1317-23; Bousarghin et al., J Clin Microbiol 2004; 40:926-32). Cells were harvested by centrifugation, resuspended in PBS containing 0.5% NP40, and allowed to stand at room temperature for 30 min. Cell lysates were then centrifuged at 14,000×g for 15 min at 4° C. The nuclear fraction was further resuspended in PBS and sonicated. The fraction was then loaded on top of a preformed cesium chloride gradient and centrifuged at equilibrium in a Beckman SW28 rotor (24 h, 27,000 rpm, 4° C.). L1-positive fractions were pooled in PBS and centrifuged (SW28 rotor, 3 h, 28,000 rpm, 4° C.). VLPs were resuspended in 0.15 mol/L of NaCl.

Pseudovirions were generated as previously described with some modifications (Touze et al., Nucleic Acids Res 1998; 26:1317-23). Briefly, 1 µg of HPV-31 VLPs were incubated in 50 mmol/L of Tris-HCl buffer (pH 7.5) containing 20 mmol/L of DTT and 1 mmol/L of EGTA for 30 min at room temperature. At this stage, expression plasmids encoding shRNA, luciferase, or green fluorescent protein (100 ng) were added to the disrupted VLPs. The preparation was then diluted with increasing concentrations of $CaCl_2$ up to a final concentration of 5 mmol/L, with or without $ZnCl_2$ (10 nmol/L). $ZnCl_2$ was used because it has been reported that $ZnCl_2$ enhances the assembly of HPV capsomers into VLPs (Hanslip et al., Biotechnol Prog 2006; 22:554-60). Pseudovirions were then dialyzed against 1×PBS overnight and stored at 4° C. before use.

The presence of capsomers, VLPs, and pseudovirions was analyzed by electron microscopy. For this purpose, samples were applied to carbon-coated grids, negatively stained with 1.5% uranyl acetate and observed at ×50,000 nominal magnification using a JEOL 1010 electron microscope.

Production of E6 and E7s hRNA Expressing Lentivirus

Lentivirus production was done using the BLOCK-iT lentiviral RNA interference expression system (Invitrogen). Briefly, an LR recombination reaction between the pENTR/U6 plasmid encoding E7 shRNA and plenti6/BLOCK-iTD-EST was done to generate the plenti6/BLOCK-iT-DEST expression construct. Lentivirus was produced by transfecting 293FT cells with 9 µg of the ViraPower Packaging Mix and 3 µg of plenti6/BLOCK-iT-DEST expression plasmid DNA using LipofectAMINE 2000 (Invitrogen). Cell culture supernatants were collected at 48 h posttransfection. Titers of E7 shRNA expressing lentivirus were determined by infecting TC1 cells with serial dilutions of lentivirus. The lentiviral stock titer was $1 \times 10^6$ TU/mL. Stably transduced TC1 cells were selected by placing cells under blasticidin selection (10 µg/mL).

Analysis of E6 and E1m RNA Levels by Reverse Transcription PCR

CaSki cells ($10^6$) transfected with shRNA pseudovirions were washed with 1×PBS and then mRNA was isolated using the Dynabeads mRNA direct kit (Dynal France SA according to the instructions of the manufacturer. Single-stranded cDNAs were synthesized from mRNAs by reverse transcription for 1 h at 42° C. in 1× incubation buffer containing 250 µmol/L of each deoxynucleotide triphosphate, 5 µmol/L oligo(dT) 20, 25 units of RNase inhibitor, and 20 units of avian myeloblastosis virus reverse transcriptase (Roche Diagnostics). cDNA samples were subjected to PCR amplification with forward and reverse primers specific to HPV-16 E6, E7, or glyceraldehyde-3-phosphate dehydrogenase (GAPDH). The primers used were E6 forward, 5' CACCAAAAGAGAACTGCAATGT 3' (SEQ ID NO: 31); and reverse, TTGCTGTTCTAATGTT GTTCCA (SEQ ID NO: 32); E7 forward, 5' GGAGATA-CACCTACATTGCATGA 3' (SEQ ID NO: 33); and reverse, GGGGCACACAATTCCTAGTG (SEQ ID NO: 34); glyceraldehyde-3-phosphate dehydrogenase forward, 5' ACA-GTCCATGCCATCACTG CC 3' (SEQ ID NO: 35); and reverse, 5' GCCTGCTTCACCACCTTCTTG 3' (SEQ ID NO: 36). PCR was set up with 200 µmol/L of deoxynucleotide triphosphate, 2 µmol/L of each specific primer, and 1 unit of Taq polymerase (Invitrogen) in a GeneAmp 9700 thermocycler (Pekin Elmer Applied Biosystems, France) programmed for 25 cycles at 50° C., 55° C., or 62° C. for E7, E6, and GAPDH, respectively. PCR products were visualized on 2% agarose gels and analyzed with GelDoc system (Bio-Rad).

Detection of p53

Cells ($2 \times 10^5$) were washed with PBS1×, dissolved directly in 50 µL of SDS gel loading buffer, and incubated for 10 min at 95° C. Fifteen microliters of each sample were separated on 12% SDS-PAGE gels. Separated proteins were electroblotted onto nitrocellulose membrane for antibody detection. Human p53 protein was detected using monoclonal antibody DO-1 (Santa Cruz Biotechnologies) and endogenous β-actin was detected using a polyclonal antibody (Sigma). Bound antibodies were visualized using an alkaline phosphatase—conjugated anti-mouse IgG antibody (Sigma) with nitroblue tetrazolium and bromochloroindolylphosphate (Sigma) as substrates.

Detection of β-Galactosidase and Luciferase Activity

Detection of β-galactosidase in CaSki, C33-A, and TC1 cells transfected with β-galactosidase plasmid and LacZ shRNA was undertaken in cells washed with PBS1× and fixed with PBS containing 2% formaldehyde and 0.2% glutaraldehyde. After 10 min at room temperature, cells were washed and incubated with (3-galactosidase revelation solution (2 mmol/L $MgCl_2$, 4 mmol/L potassium ferrocyanide, 4 mmol/L potassium ferricyanide, and 1 mg/mL X-gal). Blue cells showing β-galactosidase activity were counted. The detection of luciferase gene expression was measured by luminescence assay (Firefly luciferase assay kit; Interchim). The luminescence was integrated over 10 s (Victor2, Wallac; Perkin-Elmer) and the results were expressed as counts per second (cps) per well.

Cell Viability Assays

Transfected and untransfected cells were trypsinated and then seeded into 96-well plates. 3-(4,5-Dimethylthiazol-2-yl)-2,5-diphenyltetrazolium bromide (0.5 mg/mL) was added to cells seeded in 1004 of DMEM without FCS and incubated at 37° C. After 2 h, 100 µL of isopropanol and 0.4 mmol/L of HCl were added and absorbance was measured at 540 nm. Cell viability was determined as the ratio between the absorbance obtained in test wells and the absorbance obtained in untreated cells.

Apoptosis Assays

Apoptosis was detected using the anti-ssDNA/APOSTAIN (Abcys). Briefly, TC1 cells ($2 \times 10^5$) grown in six-well plates were transduced with 10 µg of pseudovirions containing 1 µg of E6-1, E6-2, E7-1, E7-2 shRNAs, and control shRNA. After 2 days of infection, supernatants were harvested and the cells were fixed with ice-cold ethanol. After centrifugation, $5 \times 10^5$ fixed cells were resuspended in 250 µL of formamide for 5 min at room temperature, then incubated at 75° C. for 10 min. After this step, 2 mL of PBS containing 1% of nonfat dried milk were added. After 15 min, cells were centrifuged and the pellet was resuspended in 100 µL of PBS containing anti-ssDNA monoclonal antibody F7-26. After 15 min of incubation and centrifugation, the cell pellet was resuspended in 100 µL of PBS containing fluorescence-conjugated anti-mouse IgM (20 µg/mL in PBS and 1% nonfat dry milk). After 15 min of incubation, cells were rinsed, centrifuged, and resuspended in 500 1 µL of PBS containing 1 µg/mL of propidium iodide. Negative controls were treated with mouse IgM instead of the specific primary antibody. Cells were then analyzed using a Coulter XL flow cytometer and with the Expo32 software (Beckman Coulter, France).

Apoptosis was also investigated using the Caspase-Glo 3/7 assay kit (Promega). Cells were transduced as previously with different shRNA. Two days after transduction, $2 \times 10^5$ cells were transferred to each well of a white-walled 96-well plate (Perkin-Elmer) and 100 of a caspase luminogenic substrate was added. After 1 h incubation at room temperature, the plates were read on a Luminoscan Ascent luminometer (Thermo Electron) for luminescence.

Assessment of Antitumor Effects in a Mouse Model

To investigate the effects of E6 and E7 shRNA pseudovirions on the tumorigenicity of TC1 cells, sixgroups (five mice/group) of 6-week-old female C57BL6 mice (CERJ, Le Genest St Isle, France) were subcutaneously inoculated with TC1 cells ($2 \times 10^5$). Before administration to mice, TC1 cells were transfected with pseudovirions (10 µg VLP/1 µg E6-1 or E7-1 shRNA), with a lentivirus encoding E7-1 shRNA (multiplicity of infection, 50), or with 1 µg of E7-1 shRNA with Lipofectamine. A control group received TC1 cells without treatment (mock), and one control group received TC1 cells treated with HPV VLPs. After 3 weeks, mice were sacrificed and tumors were excised and weighed.

The antitumor efficacy of the E7 shRNA-encoding pseudovirions was also investigated in mice with TC1 cell tumors. Two groups (10 mice/group) of 6-week-old female C57BL6 mice were s.c. inoculated with TC1 cells ($2 \times 10^5$). Seven days after inoculation, palpable tumors had formed in all mice, and pseudovirions containing shRNA were directly injected into each tumor at a dose of 20 µg VLP/2 µg E7-1 or 20 µg VLP/2 control shRNA every 2 days for 2 weeks. After 3 weeks, mice were sacrificed and tumors were extracted and weighed. All animal studies were approved by the regional animal ethics committee (CREEA).

Statistical Analysis

Data were expressed as mean F SE. Statistical analysis was done using Student's t test, and P<0.05 were considered significant.

Results

Design of shRNAs Directed at the E6 and E7 Proteins of HPV-16

Six sequences were designed to promote specific silencing. Two of these sequences, i.e., siE6-1 (138-159) and siE7-1 (101-119), have already been described by Jiang and Milner (Oncogene 2002; 21:6041-8) as siRNA, two other sequences, siE6-2 (421-441) and siE7-2 (148-167), corresponding to E6 and E7, respectively, were selected using the Invitrogen shRNA designer software, and two sequences (LacZ shRNA and Jiang's control shRNA) were used as controls (FIG. 1 and Table 3). These sequences were annealed and inserted into pENTR/U6.

To investigate the effectiveness of the pseudovirion system for delivery of shRNA, TC1, CaSki, and C33-A cells were transfected with a plasmid coding for hgalactosidase, with or without the pENTR/U6 LacZ plasmid coding for LacZ shRNA. In the presence of LacZ shRNA, a decrease in h-galactosidase expression was observed in all cell lines investigated, with 80%, 83%, and 81% inhibition in TC1, CaSki, and C33-A cells, respectively.

Figure 2:
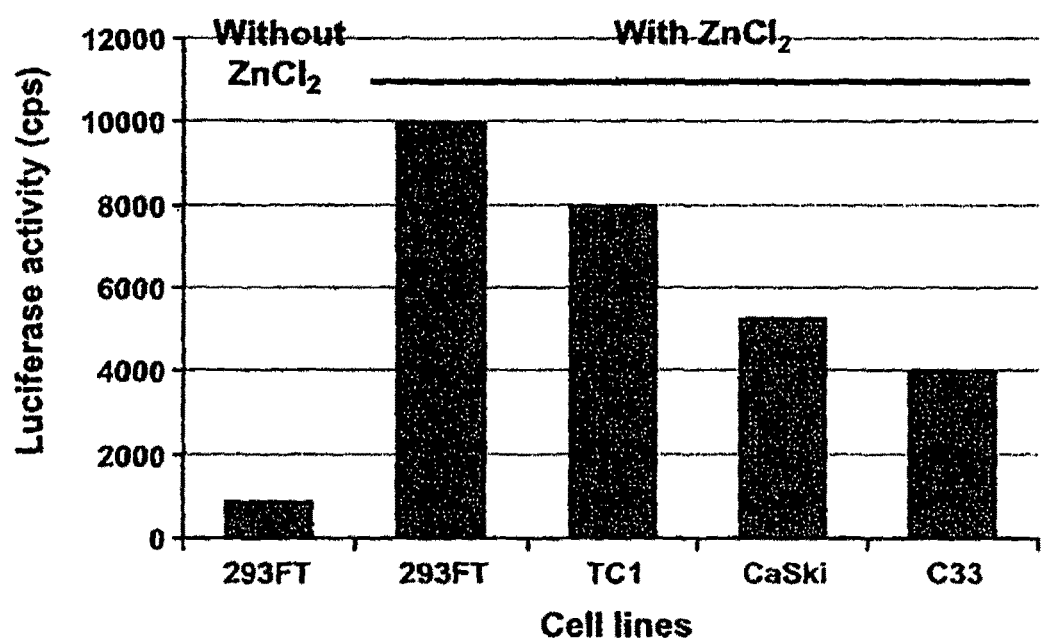

Production of Pseudovirions Encoding shRNA by Assembly of L1 Capsomers into VLPs in the Presence of $ZnCl_2$ HPV VLPs were used to encapsidate plasmids encoding for E6 and E7 shRNAs. To generate these pseudovirions, we used the disassembly-reassembly method as previously described, with the modification of adding $ZnCl_2$ during the reassembly process. Briefly, purified VLPs were incubated in a buffer containing EGTA and DTT, and in these conditions, VLPs were completely disaggregated into structures resembling capsomers. E7-1 shRNA plasmid was then added and the preparation was diluted in a buffer containing 1% DMSO and 5 mmol/L $CaCl_2$ with or without $ZnCl_2$ (10 nmol/L) in order to refold the VLPs. The presence of $ZnCl_2$ increased the reassembly of capsomers into structures resembling pseudovirions. In the presence of $ZnCl_2$, the capsomers also assembled into tubular structures of 24 nm in diameter with lengths varying from 120 to 280 nm. The role of $ZnCl_2$ in the production of pseudovirions containing a plasmid coding for luciferase was evaluated by comparing the ability of the pseudovirion preparations obtained with or without $ZnCl_2$ to transduce 293 FT cells. Luciferase activity of 9,981 cps was obtained with pseudovirions generated in the presence of $ZnCl_2$, whereas it was only 845 cps with pseudovirions obtained without $ZnCl_2$. Thus, a 12-fold increase in luciferase activity was observed when the L1 capsomers were reassembled into VLPs in the presence of $ZnCl_2$ (FIG. 2). In addition, the capacity of such HPV pseudovirions to transduce CaSki, C33-A, and TC1 cells was investigated. Such pseudovirions transduced all cell lines investigated (FIG. 2). However, a higher level of luciferase expression was observed in TC1 cells (7,990 cps, counts per second) than in CaSki cells (5,232 cps) or C33 cells (4,016 cps). In the absence of pseudovirions, luciferase activity of 57, 84, 51, and 41 cps was observed in 293FT, TC1, CaSki, and C33 cells, respectively.

Figure 3:
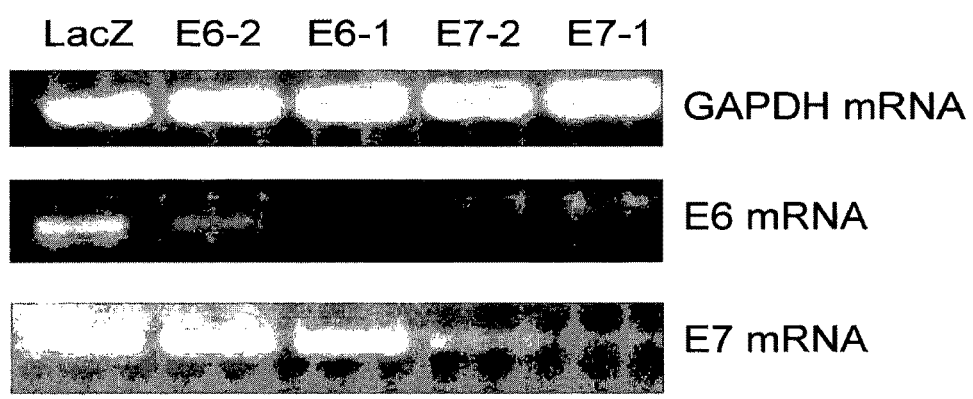
Figure 3:
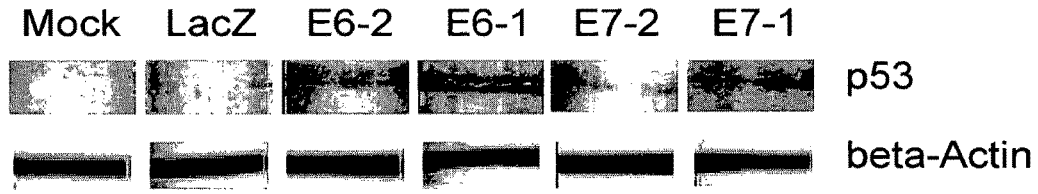

Transduction of CaSki Cells by E6 and E7sh RNA Pseudovirions Induced Increased Gene Silencing and Inhibition of Cell Growth The efficacy of gene transfer of pseudovirions in cells was investigated using pseudovirions containing a plasmid encoding green fluorescent protein. Eighty percent of TC1 cells expressed green fluorescent protein as detected by flow cytometry (data not shown). We evaluated the efficacy of E6 and E7 shRNAs by assaying their ability to interfere with protein expression. For this purpose, we first obtained the full-length cDNAs for E6 and E7 (and GAPDH as control) by reverse transcription PCR. The results showed that E7 mRNA decreased in the presence of shRNA directed against E7, a high level of interference being obtained with the Jiang sequence, whereas a lower decrease was observed with the E7-2 sequence and no decrease with control shRNA (FIG. 3A). Similar results were obtained for the detection of E6 mRNA in cells treated with E6 shRNA. A slight decrease in E6 mRNA was observed when cells were treated with E7 shRNA.

Because E6 is expressed in CaSki cells at levels too low to be detected by Western blot analysis using the antibodies available, as reported by Gu et al. (Cancer Gene Ther 2006; 13:1023-27) and Yamato et al. (Cancer Gene Ther 2008; 15:140-53), E6 shRNA activity was screened on the basis of its ability to restore p53 expression. Our results showed that the p53 level detected by Western blotting increased after expression of E6-1 shRNA over 24 hours (FIG. 3B), and decreased with time. In the presence of E7-1, E7-2, and E6-2 shRNA, the increase in p53 expression was lower than that observed with E6-1 shRNA. p53 expression was not detected when cells were treated with LacZ shRNA. These results suggest that the level of E6 protein was reduced by shRNA treatment, and that p53 not only accumulated but was also functionally active.

Figure 4:
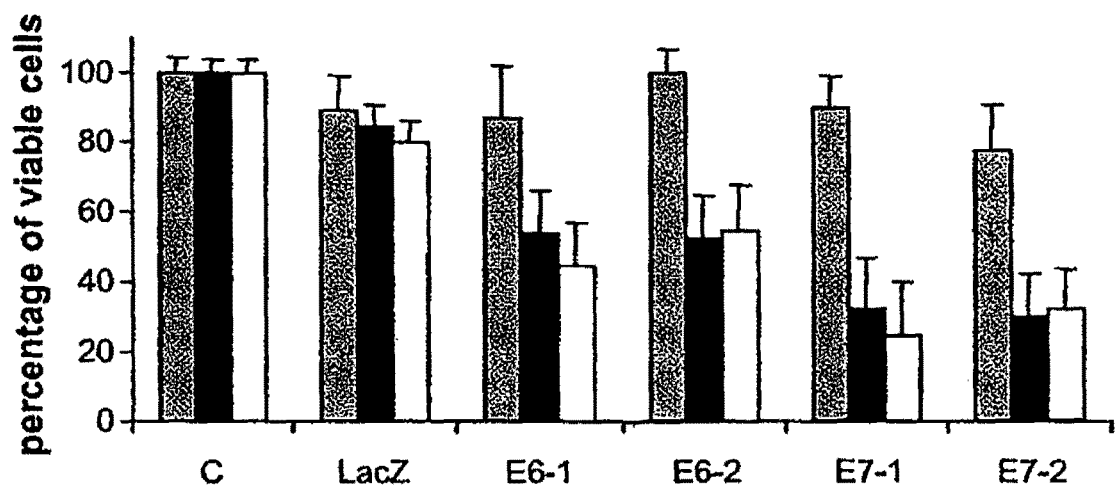

To verify whether inhibition of E6 and E7 expression could induce a reduction in cell viability, after 5 days of culture, a 3-(4,5-dimethylthiazol-2-yl)-2,5-diphenyltetrazolium bromide test was used, measuring absorbance at 540 nm, in shRNA transfected and non-transfected CaSki and TC1 cells. Our findings showed that E6 and E7 silencing induced a decrease in cell viability (FIG. 4). This reduction was greater with E7 shRNA (70% cell growth inhibition). No inhibition of cell growth was observed when HPV-negative cervical cells such as C33-A were transfected with the same shRNA, indicating that cell growth inhibition by E6 and E7 shRNAs was specific. The reduction in cell growth was similar for E6-1 and E6-2 and for E7-1 and E7-2 shRNAs.

Transduction of TC1 Cells by E6 and E7s hRNA Pseudovirions did not Induce Apoptosis An apoptosis assay based on the increased sensitivity of DNA in apoptotic cells to thermal denaturation was carried out to investigate whether cell death was due to apoptosis. In this assay, DNA is denatured by heating in the presence of formamide and stained with monoclonal antibody F7-26 specific to ssDNA. Flow cytometry did not reveal a significantly increased number of apoptotic cells with E6-1, E6-2, E7-1, and E7-2 shRNA-transfected TC1 cells compared with control shRNA-transfected cells. To further assess the existence or absence of apoptosis, a caspase assay which measures the enzymatic activity of caspases 3 and 7 was also done on TC1 cells transduced by E6 and E7 shRNA pseudovirions. No increase in caspase activity was observed with both E6 and E7 shRNAs. The results suggested that E6 and E7 shRNAs induce reduction in TC1 cell growth but not through the induction of apoptotic cell death.

Transfection of TC1 Cells In vitro by E6 and E7sh RNA Pseudovirions Induced Reduction in Tumor Growth in Mice The efficacy of the E6 and E7 shRNA pseudovirions was also investigated in vivo using the TC1/mice model. HPV pseudovirions coding for E6-1 and E7-1 shRNA, HPV VLP alone and a lentivirus encoding for E7-1 shRNA were used to transduce TC1 cells in vitro. After 24 hours, nontransfected and transfected TC1 cells were s.c. injected into C57BL6 mice.

Figure 5:
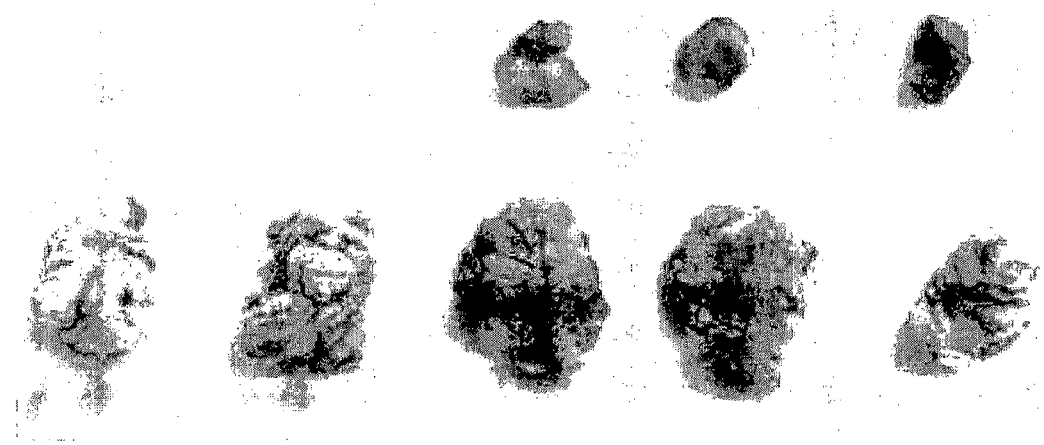
Figure 5:
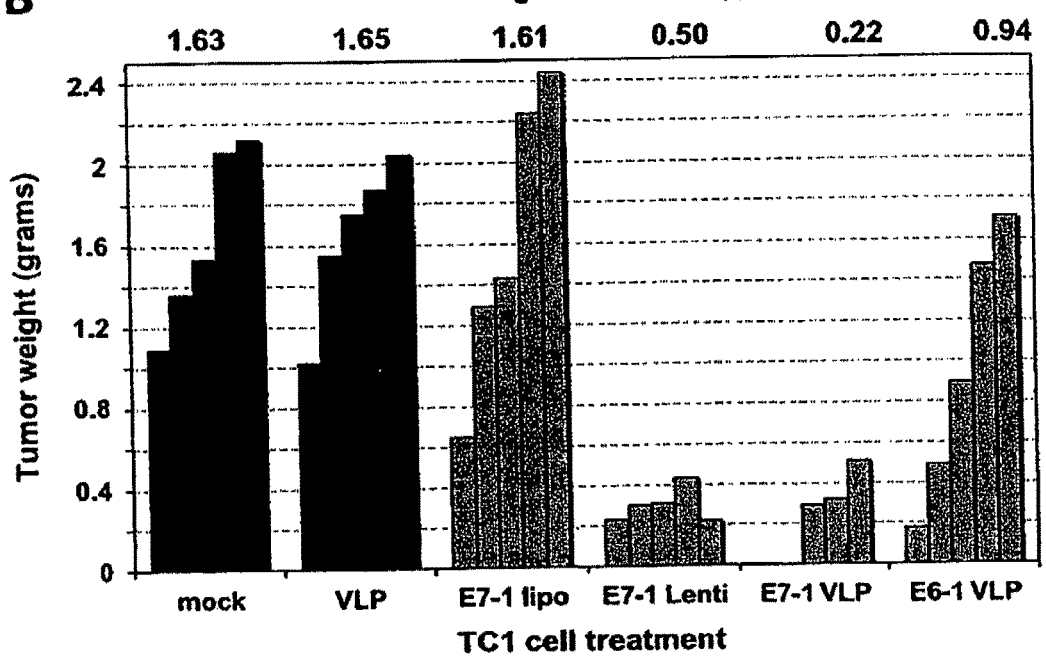

Mice were sacrificed 21 days later and tumors were excised and weighed. In control mice (mock and VLP alone), tumor weight ranged from 1.09 to 2.12 g (mean, 1.64 g). No reduction in tumor weight was observed with TC1 cells transfected with E7-1 shRNA and Lipofectamine (mean, 1.61 g). A 42% reduction in mean weight of tumors was observed with E6-1 HPV pseudovirions (P<0.10) and a 70% to 87% reduction in mean size with the E7-1 lentivirus and E7-1 HPV pseudovirions, respectively (P<0.05 and P<0.001; FIG. 5).

Figure 6:
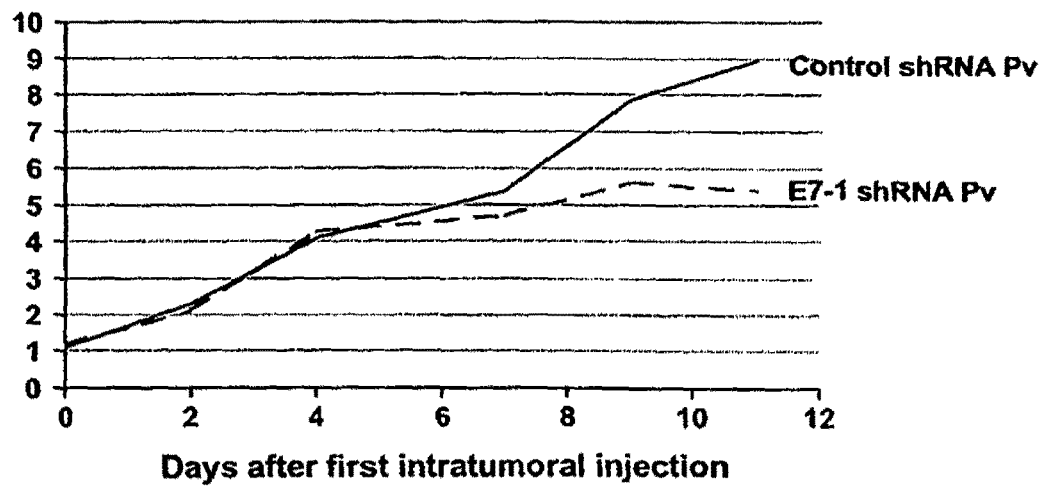
Figure 6:
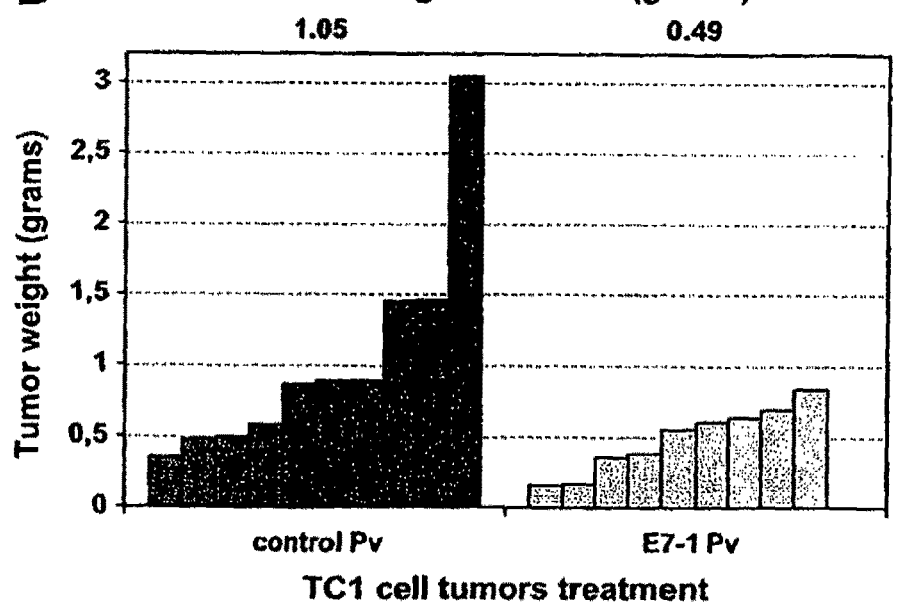

Intratumoral Transduction of TC1 Cell Tumors by E7 shRNA Pseudovirions Induced a Reduction in Tumor Growth in Mice The in vivo efficacy of the E7 shRNA-encoding pseudovirions was also investigated for their capacity to reduce tumor growth in mice with TC1 cell tumors. E7-1 shRNA was selected for these studies based on its in vitro efficacy. E7-1 shRNA pseudovirions were directly injected in tumors every 2 days over 2 weeks. After 1 week, no tumor growth reduction was observed in E7-1 shRNA-treated mice compared with the control mice (FIG. 6A). A decrease in tumor growth was then clearly observed during the second week of treatment; with a mean tumor weight of 1.05 g in mice treated with control shRNA and 0.49 g in mice treated with the E7-1 shRNA pseudovirions at the end of the second week (P=0.045).

Example 2

Identification of Neutralizing Conformational Epitopes on HPV 31 Major Capsid Protein and Functional Implications The main aim of this study was to characterize the antigenic structure and the mechanisms of neutralization of HPV31 pseudovirions. One of the questions is the exact location of the epitopes that induce HPV neutralizing antibodies and contribute to protection against infection due to interaction with the viral capsid.

It is now well established that conformational epitopes are responsible for neutralizing antibody production (Christensen et al., Virology 1994; 205:329-35; Rose et al., J Gen Virol 1994; 75:2075-79; White et al., J Virol 1998; 72:959-64; White et al. J Virol 1999; 73:4882-89; Giroglou et al. J Virol 2001; 75:1565-70). Because neutralizing epitopes of HPVs are conformation-dependent, their amino-acid composition and surface localization have not been fully characterized.

These studies are useful in vaccine design and in the investigation of virus-cell interactions. In addition, an understanding of the antigen structure of HPV is crucial for designing HPV-derived gene therapy vectors with reduced immunogenicity. One prerequisite for generating such vectors is greater understanding of viral determinants provoking neutralizing immune responses, to design pseudovirion vectors with deletion or mutation within the conformational epitopes responsible for the production of neutralizing antibodies. These mutated vectors with reduced immunogenicity will allow re-administration of these vectors without a dramatic loss of transgene efficacy due to induction of neutralizing antibodies against the vector.

Materials and Methods

HPV31 Monoclonal Antibodies

The HPV31 MAbs used in this study were as previously produced and characterized (Fleury et al., Arch Virol 2006; 151:1511-23; Fleury et al., Clin Vaccine Immunol 2008; 15:172-75). H31.D24 MAb recognize a common linear epitope that has been identified within the FG loop (amino acids 271-279) and H31.F7 MAb recognize a conformational crossneutralizing epitope that has been identified within the N-terminal part of the FG loop (Fleury et al., Arch Virol 2006; 151:1511-23). Thirteen other MAbs recognize specific conformational neutralizing epitopes. In addition, CamVir-1 monoclonal antibody (CV), which recognizes a common linear epitope on the DE loop (Carpentier et al., J Med Virol 2005; 77:558-65), was used as control. MAbs investigated using the bacterial cell surface display method were purified from crude ascites fluid by salting out with ammonium sulfate (33% final), then dialyzed against phosphate-buffered saline (PBS) followed by affinity chromatography on Protein AG/Sepharose (Pierce; Immunopure IgG purification kit).

Pseudovirus Neutralization

The neutralizing ability of each monoclonal antibody was determined previously (Fleury et al., Arch Virol 2006; 151:1511-23; Fleury et al., Clin Vaccine Immunol 2008; 15:172-5). In addition, we investigated whether the neutralization took place before or after pseudovirion cell surface binding. Tests were performed with HPV31 pseudovirions produced in 293FT cells and neutralization assays were performed using Cos-7 cells cultured in complete Dulbecco's modified Eagle's medium (Invitrogen, DMEM supplemented with 10% FCS, 100 IU/mL penicillin and 100 µg/mL streptomycin) seeded in 96-well plates and incubated for 24 h at 37° C. Assays measuring neutralization before pseudovirion cell surface binding were performed by adding the HPV31 pseudovirions previously preincubated with MAbs to the cells (100 µL) for 1 h at 37° C. Assays measuring neutralization after pseudovirion cell surface binding were performed by adding HPV31 pseudovirions to Cos-7 cells for 1 h at 37° C. After three washings to remove unbound pseudovirions, MAbs were added in 100 µL DMEM. For each assay, the supernatant was removed after 3 h at 37° C., and 200 µL complete DMEM was added. After a further 48 h incubation at 37° C., infectivity was scored by measuring the luciferase expressed by transfected cells using the Firefly Luciferase assay kit (Interchim, Montlucon, France) and luciferase expression was quantified using a Multiskan microplate luminometer (Thermo-Fisher Scientific, Courtaboeuf, France). MAbs were considered to be neutralizing if luciferase activity was reduced by >80%. Inhibition of pseudovirus binding to the cell was scored if MAbs neutralized the pseudoinfection only when added before pseudovirion binding to the cells. If antibodies neutralized pseudovirions before and after their addition to Cos-7 cells, MAbs were considered to neutralize pseudovirions via a postcell attachment mechanism.

Generation of Recombinant L1 Proteins and Purification of VLPs

The Bac-to-Bac system (Invitrogen, Fisher-Scientific, Illkirch, France) was used for expression of the HPV L1 proteins in *Spodoptera frugiperla* (Sf21) cells. Baculoviruses encoding the L1 gene of HPV16, HPV31, HPV16 DC9, and HPV16 DC31 (with a 9 or 31 amino acid C-terminal deletion, respectively) were generated previously (Touze et al., FEMS Microbiol Lett 2000; 189:121-7; Touze et al., J Clin Microbiol 1998; 36:2046-51). HPV31 DC9 and HPV 31 DC31 truncated genes were amplified by PCR from a full-length HPV31 L1 codon-optimized gene using forward (GGATCCCACCATGAGCCTGTGGAGACCCAGC, SEQ ID NO: 37) and reverse primers for DC9 (GGAAGCTTATGTGGTGG TGCTGGCGCTGGGGGC, SEQ ID NO: 38) and for DC31 (GCAAGCTT AGGCCTGCAGCAGGAACTTTCTGCCC, SEQ ID NO: 39), respectively. PCR products were cloned into pCR TOPO 2.1 by TA cloning. Positive clones were sequenced to verify the absence of unwanted mutations. HPV L1 genes were then cloned into pFastBacI plasmid previously digested by BamHI and HindIII. Recombinant baculoviruses encoding the different L1 deleted genes were generated using the Bac-to-Bac system (Invitrogen) according to the manufacturer's recommendations. Sf21 cells maintained in Grace's insect medium (Invitrogen, Cergy Pontoise, France) supplemented with 10% fetal calf serum (FCS, Invitrogen) were infected with the respective recombinant baculoviruses and incubated at 27° C. Three days post infection, cells were harvested and VLPs were purified as previously described.29, 40 Briefly, cells were resuspended in PBS containing Nonidet P40 (0.5%), pepstatin A, and leupeptin (1 µg/mL each, Sigma Aldrich, Saint Quentin Fallavier, France), and allowed to stand for 30 min at 4° C. Nuclear lysates were then centrifuged and pellets were resuspended in ice cold PBS containing pepstatin A and leupeptin and then sonicated. Samples were then loaded on a CsCl gradient and centrifuged to equilibrium (22 h, 27,000 rpm in a SW28 rotor, 4° C.). CsCl gradient fractions were investigated for density by refractometry and for the presence of L1 protein by electrophoresis in 10% sodium dodecyl sulfate-polyacrylamide gel (SDS-PAGE) and Coomassie blue staining. Positive fractions were pooled, diluted in PBS and pelleted in a Beckman SW 28 rotor (3 h, 28,000 rpm, 4° C.). After centrifugation, VLPs were resuspended in 0.15 mol/L NaCl and sonicated by one 5 s burst at 60% maximum power. Total protein content was determined using the MicroBCA kit (Pierce, Ozyme, France).

HPV31 µl HBc 263/264 mutant VLPs were produced in 293 FT cells. DNA-encoding chimeric L1 protein was obtained by mutagenesis of a codon-optimized HPV31 µl gene using a two-step PCR protocol. Overlapping PCRs were performed to obtain the DPASRE sequence of the HBc protein at position 263/264 of HPV31 µl protein. In the first step, one fragment was generated using the optimized HPV31 µl DNA sequence as template and 5' L1-NheI (CC GCTAGCCACCATGAGCCTGTGGAGACCC, SEQ ID NO: 40) and 3' L1-DPASRE (CTCTCTGCTG-GCGGGGTCGTTGAAGAAGT GCCGCACGAA, SEQ ID NO: 41) as primers. Another fragment was amplified using the optimized HPV31 L1 DNA sequence as template and 3'L1-EcoRI (CGGAATTCT ATCACTTCTTGGTTTTCT-TCC, SEQ ID NO: 42) and 5'L1-DPASRE (GACCCCGC-CAGCAGAGAGAGAAGCGGCACCGTGGGC GAG, SEQ ID NO: 43) as primers. These two overlapping fragments were used in the second PCR step as DNA templates using 5' L1-NheI and 3' L1-EcoRI primers. The resulting DNA sequence had an HBc78-83-encoding sequence between L1 bases 263/264 and an NheI restriction site in 5' and an EcoRI restriction site in 3'. For protein expression, the HPV31 L1 HBc 263/264 gene was cloned into the pIRES mammalian expression vector (BDbiosciences, Clontech). This DNA plasmid (HPV31 µl HBc 263/264-pIRES) was prepared by classical alkaline lysis and phenol/chloroform extraction and used to transfect 293 FT cells with Fugene6 (Roche Diagnostic, Meylan, France) according to the manufacturer's instructions. The cells were transfected with a total of 0.5 µg of DNA and 1 µL of Fugene6 per cm$^2$ of culture area. 293FT cells were harvested 44 h after transfection and VLPs were purified as mentioned earlier.

The self-assembly of the different HPV-L1 proteins expressed in VLPs was investigated by electron microscopy. For this purpose, VLP preparations were applied to carbon-coated grids, negatively stained with 1.5% uranyl acetate and observed at 50,000× nominal magnification with a JEOL 1010 electron microscope. All the electron micrographs were taken at 30,000× or 50,000×.

Investigation of VLP Binding Competition of HPV31 MAbs by Surface Plasmon Resonance Analyses were performed with a Biacore 1000 (Biacore AB, Uppsala, Sweden) equipped with CM3 (carboxymethylated dextran) sensor chips. CM3 sensorchips were treated with 354 of 0.05 mol/L 1-ethyl-3-(3-dimethylaminopropyl)-carbodiimide hydrochloride and 0.2 mol/L N-hydroxysuccinimide at a flow rate of 5 µL/min and then the HPV31 L1 VLPs (32 µg/mL in 35 µL of PBS buffer) were covalently coupled at a flow rate of 5 µL/min. The residual carboxyl groups were subsequently blocked by 50 µL of 1 mol/L ethanolamine-HCl (pH 8.5) at a flow rate of 10 µL/min. Unbound VLPs were eliminated by injection of 5 µL of HCl-glycine (10 mmol/L, pH 2.2) at a flow rate of 10 µL/min. A flow rate of 20 µL/min was used for all interaction analyses conducted at room temperature. Antibody saturation of the bound HPV31 L1 VLPs was obtained for each MAb by three injections of 30 µL of ascites fluid diluted 1:10 in PBS. The MAb saturation was verified by injection of 30 µL of hybridoma supernatant of the same MAb diluted 1:4 in PBS. Competition was then established by successively injecting five different hybridoma supernatants diluted 1:4 in PBS (30 µL each). The biosensor was then regenerated by three injections of 10 µL of 30 mmol/L HCl, and another cycle of saturation-competition was performed on the same VLPs coupled flow-cell. Several other regeneration buffers (including 2 mol/L NaCl, 10 mmol/L NaOH, and 20, 25, 30, and 50 mmol/L HCl) were investigated. The selected buffer (30 mmol/L HCl) was shown to remove 100% of the bound antibodies, not to remove VLPs from the sensorchip, and not to affect VLPs conformation, because antibodies directed at the conformational epitopes still bound to VLPs as effectively as before the regeneration treatment.

Epitope Mapping Using Bacterial Cell Surface Display

The bacterial cell surface display method using the pFliTrx vector uses a 12-mer peptide library inserted in a thioredoxin domain (TrxA) to constrain the peptides. This thioredoxin domain is itself inserted into the major bacterial flagellar protein (FliC) to be displayed on the surface of E. coli (Lu et al., Biotechnology (NY) 1995; 13:366-72; James et al., Science 2003; 299:1362-1367). The pFliTrx Random Peptide Display Library (Invitrogen, Cergy Pontoise, France) was obtained by inoculation of 1 mL of the peptide library stock solution into 50 mL of IMC Medium (6 g/L Na$_2$HPO$_4$, 3 g/L KH$_2$PO$_4$, 0.5 g/L NaCl, 1 g/L NH$_4$Cl, 0.2% casamino acid, 0.5% glucose, 1 mmol/L MgCl$_2$) containing 100 µg/mL ampicillin and then shaken (225-250 rpm) overnight at 25° C. Peptide expression was induced by adding 100 µg/mL of tryptophan to 1010 bacteria from the overnight culture in 50 mL of IMC Medium containing 100 µg/mL of ampicillin, and then shaken at 25° C. for 6 h.

For library screening against anti-HPV31 antibodies, 20 µg of MAb in 1 mL sterile water was coated on a 60-mm plate (Nunclon D, Nunc, ATGC, Marne-la-Valle'e, France) for 1 h with gentle agitation at 50 rpm on an orbital shaker. After washing with 10 mL of sterile water, 10 mL of Blocking Solution (IMC medium containing 100 µg/mL ampicillin, 1% low-fat dry milk, 150 mmol/L NaCl, 1% a-methyl mannoside) was added and incubated for 1 h under agitation (50 rpm). After decanting the blocking solution, 10 mL of the bacteria cell culture were added with 0.1 g dried milk, 300 µL of 5 mol/L NaCl, 500 µL of 20% a-methyl mannoside (final concentration: 1% nonfat, dried milk, 150 mmol/L NaCl, 1% a-methyl mannoside). After gentle agitation at 50 rpm for 1 min and incubation at room temperature for 1 h, the plates were washed five times (50 rpm for 5 min) with 10 mL of the IMC medium containing 100 µg/mL ampicillin and 1% amethyl mannoside. The bound bacterial cells were then eluted into the residual volume of washing solution by vortexing the plates for 30 s. They were transferred to a 50 mL culture flask and grown under shaking (225-250 rpm) at 25° C. overnight. This panning cycle was repeated four more times and the overnight culture from the fifth panning was streaked onto RMG plates (6 g/L Na$_2$HPO$_4$, 3 g/L KH$_2$PO$_4$, 0.5 g/L NaCl, 1 g/L NH$_4$Cl, 2% Casamino acid, 0.5% glucose, 1 mmol/L MgCl$_2$, 1.5% agar) containing 100 mg/mL ampicillin and incubated overnight at 30° C. Twenty-four to 30 colonies from the RMG/ampicillin plate were each inoculated into 2 mL RM medium (6 g/L Na$_2$HPO$_4$, 3 g/L KH$_2$PO$_4$, 0.5 g/L NaCl, 1 g/L NH$_4$Cl, 2% Casamino acid, 1% glycerol, 1 mmol/L MgCl$_2$) containing 100 µg/mL ampicillin. After incubationat 30° C. overnight with shaking, DNA was extracted by the classical alkaline lysis phenol/chloroform DNA minipreparation. Nucleotide sequence analysis was performed using the FliTrx forward sequencing primer. Sequences were run on an ABI PRISM 3100 Avant DNA sequencer (PerkinElmer, Courtaboeuf, France). Sequences were analyzed using Dialign2 (Morgenstern et al., Gioinformatics 1999; 15:211-18).

Detection of MAb reactivity against wild-type and mutant VLPs by ELISA

Microplate wells (Maxisorp, Nunc) were coated with VLPs. After incubation at 4° C. overnight and two washes with PBS-Tween 20 (0.1%), wells were saturated with PBS supplemented with 1% FCS for 1 h at 37° C. Duplicate wells (two tests and one control) were incubated with MAbs diluted in PBS 5X—Tween (1%)—FCS (10%) for 1 h at 37° C. After four washes, peroxidase-conjugated goat anti-mouse Ig Fc (Sigma Aldrich) diluted 1:1,000 in PBS—Tween (1%)—FCS (10%) was added to the wells and incubated for 1 h at 37° C. Then after four washes, 0.4 mg/mL O-phenylene-diamine and 0.03% hydrogen peroxide in 25 mmol/L sodium citrate and 50 mmol/L Na$_2$HPO$_4$ were added. After 30 min, the reaction was stopped with H$_2$SO$_4$ 4N and absorbance was read at 490 nm. For data analysis, optical density (OD) values obtained in the absence of the first antibodies were subtracted from the OD values of test samples. The data presented are the means of three to four determinations.

Heparin- and ECM-Based Enzyme-Linked Immunosorbent Assays

The interaction between VLPs and heparin was tested using an assay derived from the heparin-binding assays described by Giroglou et al. (J Virol 2001; 75:1565-70) for HPV33 VLPs. Microtiter plates (Maxisorp, Nunc) were coated overnight at 4° C. with 200 ng per well of heparin-BSA (Sigma) or MatrigelVR (BD Biosciences, Le pont de Claix, France) After four washes with PBS containing 0.1% Tween 20, nonspecific binding sites were blocked by incubation for 1 h at 37° C. with PBS plus 1% FCS. After washing, 200 ng/well of VLPs diluted in PBS were added. Following incubation at 37° C. for 60 min and four washes, anti-HPV31 VLP MAbs diluted 1:1000 in PBS, 0.1% Tween 20, and 10% FCS were added and incubated at 37° C. for 60 min. After 1 h incubation at 37° C. and four washes, bound antibodies were detected using mouse anti-IgG antibodies covalently linked to horseradish peroxidase. After 1 h incubation at 37° C. and four washes, 100 pt of substrate solution containing O-phenylene diamine and H$_2$O$_2$ were added. The reaction was stopped after 30 min by addition of 100 µL 2 mol/L H$_2$SO$_4$ and absorbance was read at 492 nm with an automated plate reader. The absorbance of control wells without VLPs was subtracted from values for test wells. Simultaneously, a second plate was coated with heparin-BSA or MatrigelVR. After incubation and washing, 200 ng/well of VLPs preincubated for 1 h at 37° C. with MAbs diluted 1:1000 in PBS, 0.1% Tween 20, and 10% FCS were added. Bound antibodies were detected with mouse anti-IgG antibodies covalently linked to horseradish peroxidase as described earlier. Inhibition of VLP binding to heparin or Matrigel was calculated as the reduction in OD observed between adding the MAbs before the interaction of VLPs with heparin and after. The results are expressed as the percentage of reduction in OD.

VLP Binding to HS and ECM Assays

Microtiter plates (Maxisorp, Nunc) were coated with heparin-BSA as described earlier. After a blocking step, VLPs diluted in PBS were added. Following incubation at 37° C. for 60 min and washing, CanVirl MAbs diluted 1:5000 in PBS, 0.1% Tween 20 and 10% FCS were added and incubated at 37° C. for 60 min. Bound antibodies were detected after four washes using mouse anti-IgG antibodies covalently linked to horseradish peroxidase and then the tests were performed as mentioned earlier in the test for the interaction between heparin and MAbs. The results are expressed as OD value.

Visualization of HPV31 Epitopes by Homology Modeling of HPV31 L1 Protein

The sequence for HPV31 µl protein (Genbank ID, P17388) was submitted as input to the Swiss-Model modeling tool (swissmodel.expasy.org). A template search based on sequence similarity identified HPV16 L1 (PDB code 1DZL and 2R5H), HPV-35 L1 (2R5J), HPV-11 L1 (2R5K), and HPV-18 µl (2R51) as possible 3D templates. Because HPV31 µl is more similar to HPV16 and HPV35 µl sequences, we selected the corresponding 3D templates (1DZL, 2R5H and 2R5J) to model the L1 structure of HPV31. The model of HPV31 µl was evaluated using ANAOLEA (swissmodel.expasy.org/anolea/) and found to be correct for further structural analysis of epitope locations. The L1 pentamer of HPV31 was reconstructed with Swiss-sPDBViewer using the HPV31 L1 model and the information for non-crystallographic symmetries (transformation matrices) of the HPV16 VLP (1DZL) (Chen et al., Mol Cell 2000; 5:557-67). Atomic coordinates of the pentamer for the HPV31 L1 VLP were saved in PDB format and displayed using the PYMOL program, a molecular graphic visualization tool for macromolecular structures (pymol.org).

Results

Epitope Mapping of HPV31 L1 MAbs Using Surface Plasmon Resonance

Figure 7:
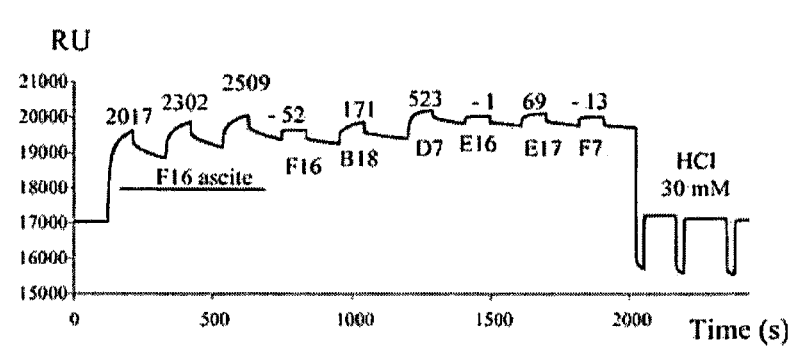
Figure 7:
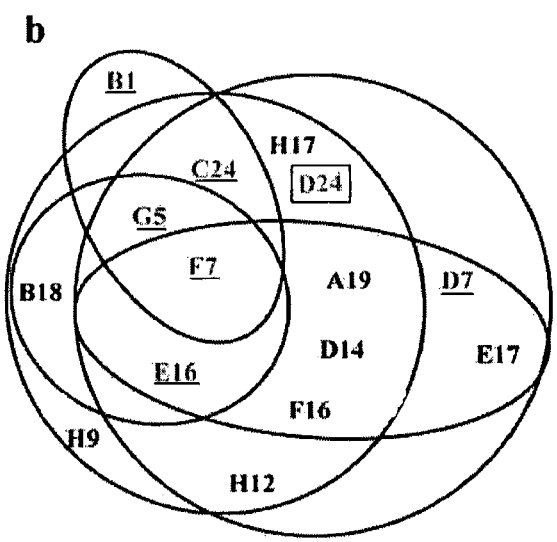
Figure 7:
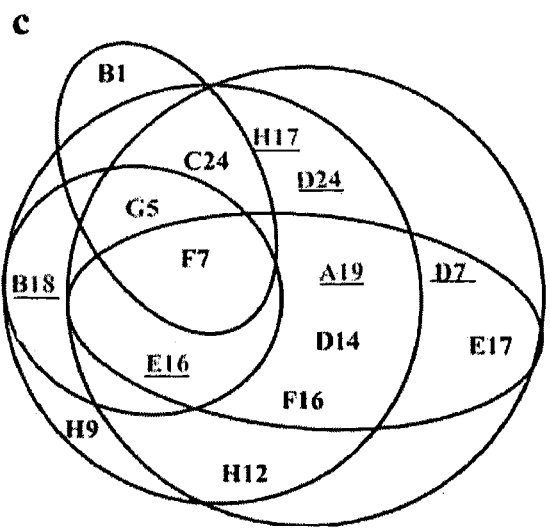

Epitope mapping was performed using 15 MAbs raised against HPV31 µl protein. All competitions between these MAbs were tested. For example [FIG. 7(a)], epitope competition was established by saturating coupled HPV31 L1 VLPs with H31.F16 MAb (crude ascites fluid), and the MAb saturation was verified by injection of the same MAbs (hybridoma supernatant). The low-resonance unit (RU) that occurred after addition of H31.F16 MAb (−52 RU) proved that saturation was achieved. After saturation there was a decrease in RU, due to the dissociation of saturating MAb and this was the reason for the negative RU. MAb binding competition was then established by successively injecting H31.B18, H31.D7, H31.E16, H31.E17, and H31.F7 MAbs (hybridoma supernatants). H31.E16 and H31.F7 MAbs did not bind to HPV31 L1 VLPs (−1 and −13 RU, respectively), suggesting that the epitopes recognized by these two MAbs were similar, or very close, to the epitope recognized by the H31.F16 MAb. In contrast, significant binding to VLPs was observed using H31.B18, H31.D7, and H31.E17 MAbs (171, 523, and 69 RU, respectively), suggesting that these antibodies recognized epitopes which were different from that recognized by the H31.F16 MAb. The biosensor was then regenerated by three injections of 30 mmol/L HCl. This method was used for all the other competition assays.

Each of the 15 MAbs investigated competed with at least three others, but none of the MAbs competed with all the other MAbs. An epitope map was established using these results [FIG. 7(b)], and epitopes recognized by H31.F7 MAb had a central position in this map. The epitope recognized by this MAb had already been identified on the L1 FG loop (Carpentier et al., J Med Virol 2005; 77:558-65; Fleury et al., Arch Virol 2006; 1511-23). MAbs competing less with the other MAbs (H31.B18, H31.B1, and H31.H9) were located at the periphery of the epitope map.

Binding of HPV31 MAbs to HPV31/HBc VLPs

The reactivity of MAbs was analyzed using the HPV31 L1/HBc 263/264 mutant and HPV31 µl wt VLPs to identify whether some of the neutralizing epitopes were located on the FG loop. In addition to HPV31 L1 VLPs produced previously, we constructed a HPV31 L1 mutant by insertion of the hepatitis B core (HBc) motif DPASRE at position 263-264. VLP binding of all the type-specific MAbs was affected by the insertion of the HBc motif at position 263/264. It should be noted that the reactivity of the non-neutralizing H31.D24 MAb, which recognized a linear epitope located at position 271-279 (SVPTDLYIK, SEQ ID NO: 44) was not affected by the insertion. Binding of CamVir-1 MAb that recognized a linear epitope identified outside the FG loop was also not affected by the mutation introduced. The crossneutralizing MAb H31.F7 reacted similarly to both HPV16 and HPV31 wt VLPs, but was affected by insertion of the HBc motif at position 263/264.

Epitope Mapping of 5 MAbs Using Bacterial Surface Display

Epitope mapping using bacteria for display of peptide libraries provides a new approach for epitope mapping of both monoclonal and polyclonal antibodies (Rockberg et al., Nat Methods 2008; 5:1039-45). One such system, the pFliTrx Bacterial Display system, was used to identify L1 epitopes. The bacterial cell surface display using the pFliTrx vector uses a 12-mer peptide library inserted in a thioredoxin domain to constrain the peptides, allowing the display of conformational epitopes. This thioredoxin domain is itself inserted in the major bacterial flagellar protein of E. coli to be displayed on the surface of bacteria. High-titer MAbs purified from ascites fluid were coated on Nuclon D plates for library screening against anti-HPV31 antibodies and in vitro selection rounds were performed on MAbs bound to the plates for the selection of bacteria displaying peptides interacting with the MAbs. For each round, the bacterial library was added to a cell culture dish for positive selection. The unbound bacteria were washed off, and bound bacteria were recovered. After five rounds, single clones were selected and DNA was isolated for sequencing. Sequences were first analyzed using the Dialign2 program. High-scoring matching peptides were selected and then aligned using Dialign2 with the full length HPV31 µl protein sequence. The HPV31 L1 sequences matching all the selected peptides were retained. We first used this system with the H31.D24 MAb, which recognized a previously identified linear epitope at position 271-279 (SVPTDLYIK, SEQ ID NO: 44) within the FG loop of HPV31 µl. After bacterial display selection, 24 positive clones were sequenced and analyzed. Six of the 24 peptides selected with H31.D24 MAb matched each F2 other and matched the HPV31 µl protein (see FIG. 8), the consensus sequence identified being at position 275-279 (DLIYK, SEQ ID NO: 46).

Bacterial display was therefore used to investigate the neutralizing conformational epitope recognized by MAb H31.F7, which is crossreactive with HPV16, 18 and 58, and weakly neutralizing for HPV types 16 and 31. Twenty-four positive clones were selected by bacterial display using the H31.F7 MAb. Five of the 24 peptides selected matched each other and matched the HPV31 L1 protein sequence 259-266 (RHFFNRSG, SEQ ID NO: 47). Three type-specific neutralizing MAbs (H31.F16, H31.H12, and H31.B1), which recognized conformational epitopes, were also investigated. Positive clones were selected for each MAb. Five peptides selected with H31.F16 MAb, five with H31.H12 MAb and six peptides selected with H31.B1 MAb matched each other and matched the HPV31 µl protein sequence SGTVGESVP (265-273) (SEQ ID NO: 48) for H31.F16 MAb, RSGTVG sequence (264-269) (SEQ ID NO: 49) for H31.H12 MAb and RSGTVGESV sequence (264-272) (SEQ ID NO: 50) for H31.B1 MAb.

MAb Neutralization of Pseudovirions Pre- and Postattachment

Figure 9:
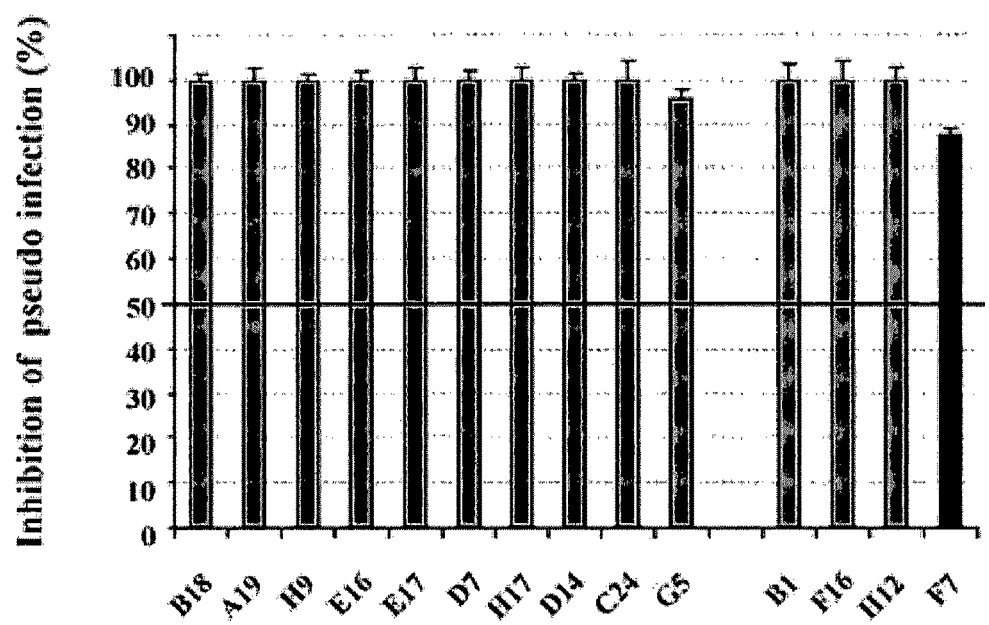
Figure 9:
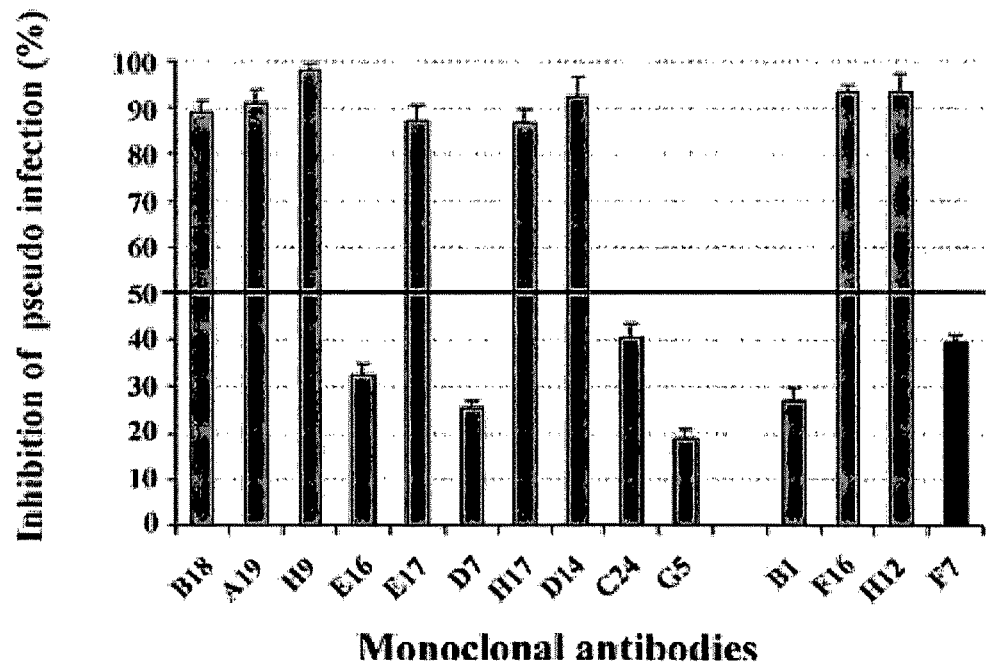

HPV16 and HPV33-specific antibodies have been shown to neutralize before or after attachment to target cells (Selinka et al., J Virol 2003; 77:12961-67; Day et al., J Virol 2007; 81:8784-92). The mechanism of viral neutralization by anti-HPV31 MAbs was determined by neutralization assays, the MAbs being added either before addition of F3 the pseudovirions to COS-7 cells [FIG. 9(a)] or 1 h postcell attachment [FIG. 9(b)]. The six MAbs [H31.B1, H31.C24, H31.G5, H31.E16, H31.F7, and H31.D7, FIG. 9(b)] neutralized HPV31 pseudovirions by inhibition of cell attachment because they neutralize before virus attachment but not after pseudovirus binding to the cell [FIG. 9(b)]. The eight other MAbs neutralized HPV31 pseudovirions via a postcell attachment mechanism because they neutralized the pseudovirions before and after cell attachment. It should be noted that the epitope map [FIG. 7(c)] obtained by surface plasmon resonance analysis suggested a cluster of five of these six MAbs that neutralized HPV31 pseudovirions by inhibition of cell attachment.

VLPs Binding to HS and ECM: Effects of HPV31MAbs and L1 C-Terminal Deletion

Figure 10:
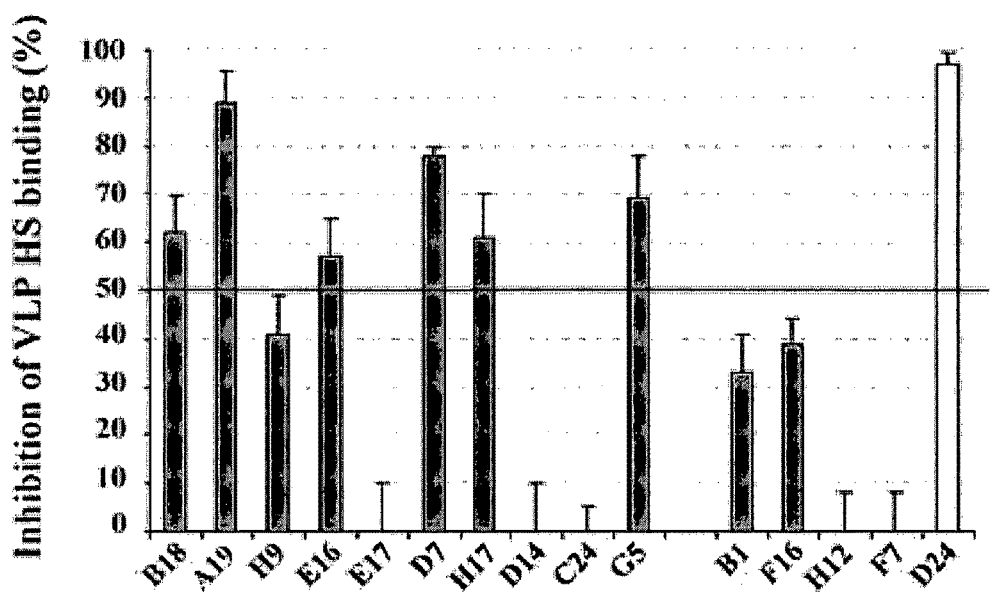
Figure 10:
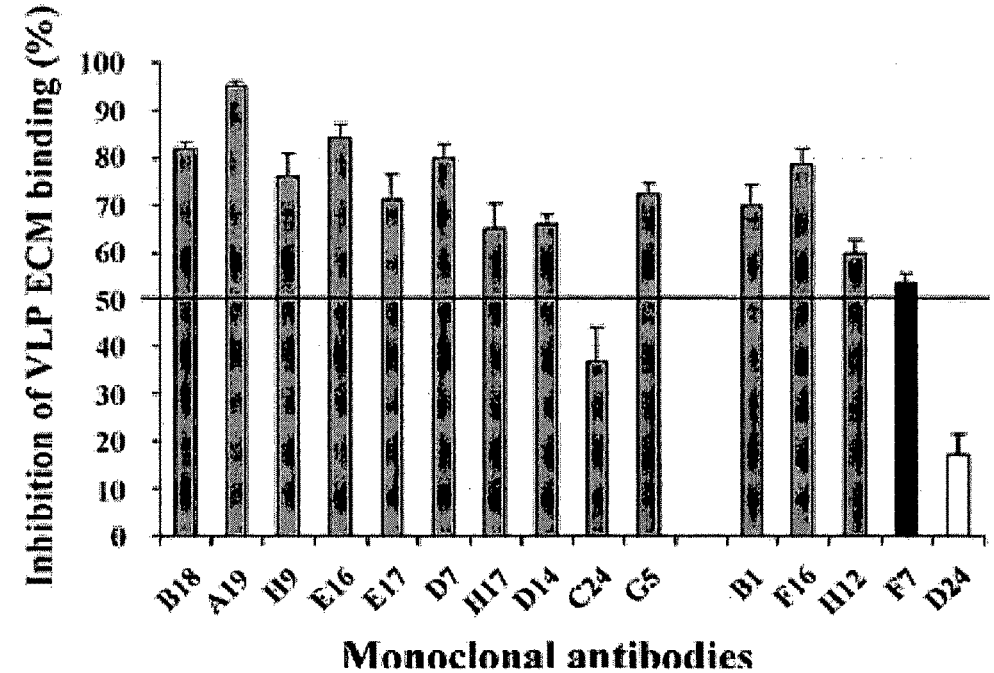

The inhibition of VLP binding to heparin by HPV31 MAbs was investigated using an ELISA in which MAbs were added to VLPs before their binding to heparin coated on ELISA plates. The results indicated that the non-neutralizing H31.D24 MAb that recognized a linear epitope strongly inhibited the binding of VLPs to heparin, as only 6 of the 14 MAbs recognized confor-F4 mational neutralizing epitopes [FIG. 10(a)]. The epitope map obtained by surface plasmon resonance analysis indicated a cluster of some of the MAbs that inhibited VLP binding to heparin [FIG. 7(c)]. There was no clear correlation between MAbs that neutralized the pseudovirions before attachment to the cells and those that inhibited binding to HS. However, three neutralizing antibodies (H31.G5, H31.E16, and H31.D7) demonstrated both abilities (see FIG. 10). Inhibition of VLP binding to ECM proteins was investigated by ELISA using MatrigelVR as a surrogate for ECM. The results [FIG. 10(b)] indicated inhibition of VLP binding to ECM proteins (>50%) by all the neutralizing antibodies, with the exception of H31.C24 (37% inhibition). The non-neutralizing antibody H31.D24 did not inhibit binding of VLPs to ECM proteins.

Figure 11:
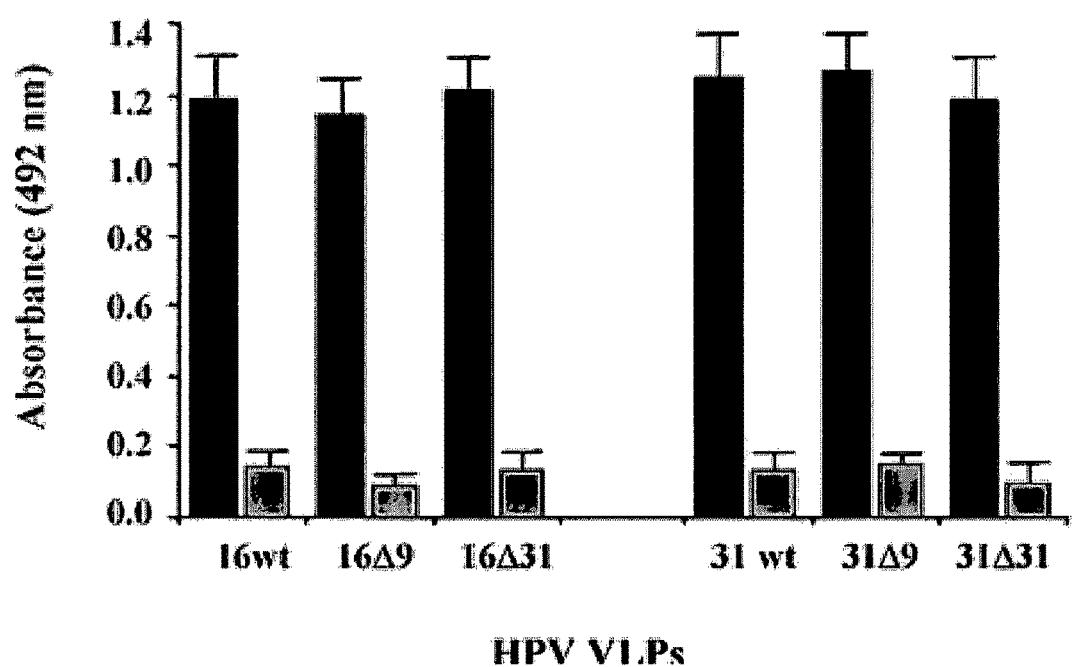

To investigate further the interaction of VLPs with HPSGs, we used four C-terminal deletion mutants for the analysis of heparin binding to L1 proteins. HPV16 D9 and HPV16 D31 mutants with C-terminal deletions of 9 and 31 amino acids, respectively, had already been produced, 44 and HPV31D9 and HPV31D31 µl mutants were similarly produced for the purposes of this study. These HPV31 deletion mutants self-assembled into VLPs (see FIG. 7) as previously observed for the corresponding HPV16 deletion mutants 44 and these four C-terminal deleted VLPs bound to heparin in a similar manner to wt VLPs. However, binding to heparin is lost when these VLPs were denatured, confirming that heparin binds to a conformational motif on VLPs, and that this motif is not present in the C-terminal part of the L1 protein (see FIG. 11). As infection of target cells by HPV is a multistep process involving HSPG, ECM, and an unknown secondary receptor, we investigated the effects of HPV31 MAbs on neutralization of ECM HPV VLP binding.

The epitope recognized by H31.D24 is a linear epitope and epitopes recognized by the three neutralizing MAbs (H31.B1, H31.F16, and H31.H12) are conformational, while H31.B1 MAb is partially cross-neutralizing and cross-reacting.

Figure 12:
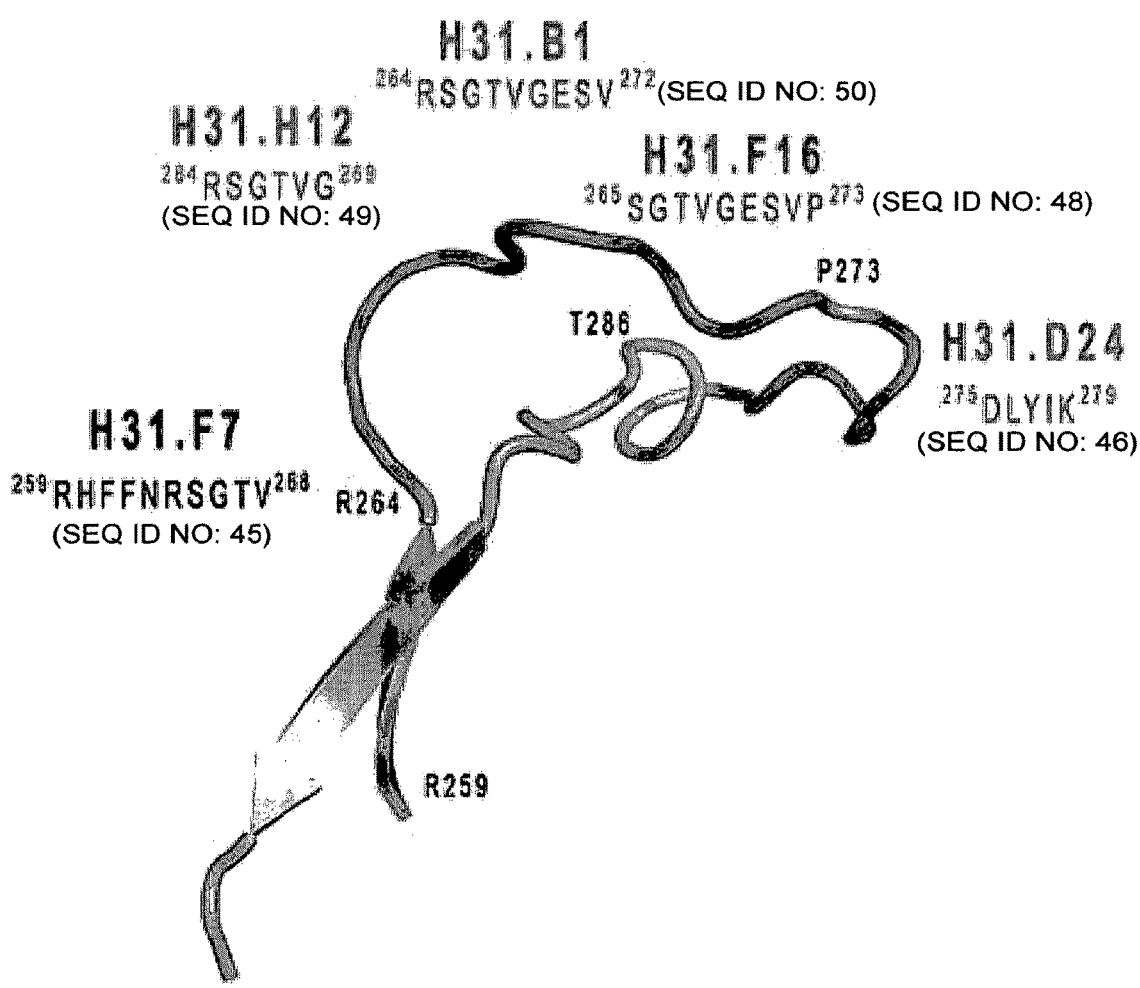
Figure 14:
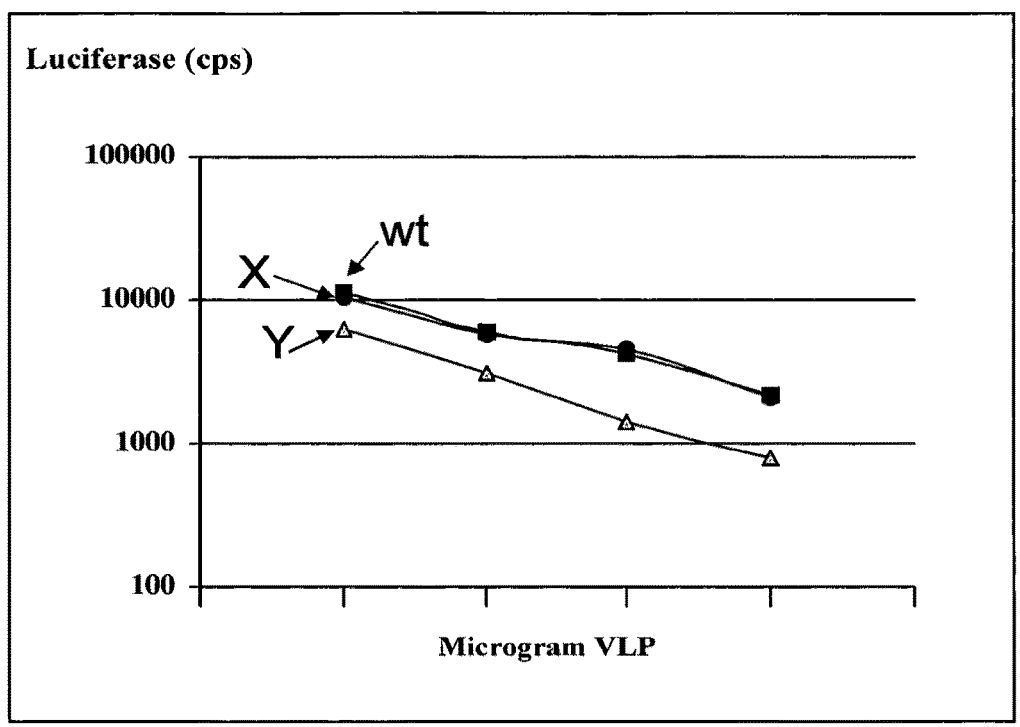

The epitope recognized by H31.F7 MAb, a cross-reacting and partially cross-neutralizing MAb, was identified on the N-terminal part of the FG loop of the HPV31 L1 protein at position 259-268 (RHFFNRSGTV, SEQ ID NO: 45) [FIG. 12, the 3D capsomer structure was reconstructed with SwissPDBViewer using the HPV31 µl model and the information for AQ6 non-crystallographic symmetries of the HPV16 VLP [PDB code: 1DZL, (Chen et al., Mol Cell 2000; 5:557-67)]], and is mostly inaccessible F6 from the surface of the capsomer according to the HPV31 model. This is in agreement with the fact that the early region of the FG loop evidenced identical structures between HPV types and with the hypothesis of Bishop et al.64 on the structural analysis of L1 proteins suggesting that this region of the FG loop must be able to induce crossreactivity between types but be poorly antigenic and/or inaccessible.

For HPV16 and HPV33, it has been shown that various L1 protein surface exposed loops contribute to the induction of neutralizing antibodies to epitopes identified in only one loop and epitopes for which several loops contribute to the binding site, 15, 46, 47 and it has been suggested that noncontiguous regions of L1 could contribute to neutralizing epitopes recognized by MAbs. Our findings were in favor of the HPV31 neutralizing antibodies being mainly directed against the FG loop and the FG loop only contributing to the binding to neutralizing antibodies. The fact that L1 hypervariable loops are in close proximity to each other did not rule out the possibility that mutations or insertions in other loops affect the FG conformational epitopes as observed by Roth et al. 47 We observed that the crossreacting H31.D24 MAb which recognized the DLYIK (SEQ ID NO: 44) sequence (275-279) dramatically reduced the ability of HPV31 to bind to heparin, thus confirming the role of Lysine 278 in HS binding. However, this antibody had no neutralizing effect on HPV31 pseudovirions, 41, 65 and three other neutralizing antibodies that recognized conformational epitopes known to bind to a sequence situated in the N-terminal part of the FG loop had no or limited effect on binding to heparin. H16.V5 and H16.E70 MAbs have been shown not to block interactions with the cell surface. However, these neutralizing antibodies inhibit virus binding to ECM produced from HaCaT cells, and neutralize pseudovirions via a postcell attachment mechanism.43 In agreement with this, we observed that the three type-specific neutralizing antibodies did not compete with HS for binding to VLPs and that only one of them (H31.B1) neutralized by inhibition of the binding of the VLPs to cells. However, all these antibodies compete for binding to the ECM, in contrast to the non-neutralizing H31.D24 MAb. These results suggested that these antibodies recognized an epitope in the vicinity of the conformational basic cluster of lysine involved in HPV16 VLP binding to HS35. It should be noted that the most important lysine of the cluster was present within the epitope recognized by the H31.D24 MAb. In addition, investigation of pre- and postattachment neutralization of HPV31 pseudovirions by MAbs revealed that six of the HPV31 neutralizing antibodies acted by preventing the cell surface binding of the viral particles, and the other eight neutralizing MAbs interfered with pseudovirions by preventing their internalization. Our findings indicate that, for the entire set of MAbs, there is no correlation between neutralization and the ability of MAbs to bind HS. Lopez et al.66 was recently reported that anti-HPV antibodies detected in natural infection inhibit HPV16 binding to HS, and they observed that those with the highest neutralizing titers were those that inhibited binding to HS. In conclusion, our findings showed that HPV31-neutralizing MAbs recognize conformational epitopes located on the FG loop of HPV31 μl protein and that they act either by blocking attachment to target cells or by neutralization of post-cell attachment. The precise determination of three type-specific neutralizing epitopes by bacterial surface display confirmed their location on the central part of the FG loop and identified a cross-reacting and partially cross-neutralizing conformational epitope on the relatively conserved N-terminal part of the FG loop. The solvent-exposed amino acid residues of the FG loop were distributed on both sides of a groove formed along an axis defined by Pro 273 to Leu 287 [FIG. 12]. Our findings showed that the right part of the groove contained a linear non-neutralizing epitope recognized by H31.D24 MAb. This is also a hot spot for heparan sulfate binding, thus explaining why H31.D24 and HS compete for binding to this region. The conformational, neutralizing epitopes identified were all located on the left side of the FG loop groove (see FIG. 12). The fact that antibodies directed against these epitopes did not strongly compete with HS may be explained by differences in the MAb binding modes, as previously described for MAbs directed against BPV L1 protein.67 However, some other HPV31 neutralizing MAbs did compete with HS binding, suggesting that either these MAbs have a different tilt when they bind to their respective epitopes, thus interfering with HS binding to a greater or lesser extent, or that they are directed against amino acid residues from both sides of the groove. H31.D24 MAb bound to the tips of VLPs and this supports the hypothesis that non-neutralizing epitopes are also present on the surface of HPV particles. The results obtained indicated that the FG hypervariable loop of HPV31 is dense in neutralizing epitopes and suggested that HPV31 MAbs bind to overlapping but distinct epitopes on the central part of the FG loop, in agreement with the exposure of the FG loop on the surface of HPV VLPs, and thus confirming that neutralizing antibodies are mainly located on the tip and crown of the capsomere. The results also support and confirm that the blocking of virus attachment to the ECM is an important neutralization mechanism but not the blocking of virus attachment to HS.

Example 3

Generation of HPV16/31 L1 Mutants

Papillomaviruses are small non-enveloped DNA viruses and their icosahedral capsid is constituted of L1 and L2 proteins, which encapsidate a closed circular, double-stranded DNA of about 8 kbp. The viral capsid of 50-60 nm in diameter contains 72 pentamers of L1 major protein and 12 to 72 copies of L2 minor capsid protein. Immunization with L1 protein self-assembled into virus-like particles (VLPs) induces the production of high levels of neutralizing antibodies and confers type-specific and long-lasting protection, as demonstrated in animal models (Breitburd et al., J Virol 1995; 69:3959-63; Suzich et al., PNAS1995; 92:11553-57; Christensen et al., J Virol 1996; 70:960-65). The antibody responses are typically generated against epitopes found on the external loops of the viral capsid L1 protein present on the outer VLP surface (Christensen et al., Virology 2001; 291:324-34; Sadeyen et al., Virology 2003; 309:32-40; Orozco et al., J Virol 2005; 79:9503-14; Yaegashi et al., J Virol 1991; 65:1578-83). Neutralizing capsid epitopes are important determinants for antibody-mediated immune protection against HPVs, and both linear and conformational epitopes have been identified on the surface of HPV L1 VLPs and pseudovirions (Yaegashi et al., J Virol 1991; 65:1578-83; Volpers et al., J Gen Virol 1995; 76:2661-67; Heino et al., J Gen Virol 1995; 76:1141-53; Christensen et al., Virology 1996; 224:477-86).

L1 residues within the FG loop of HPV16 L1 and the EF loop of HPV31 L1 have been reported to be involved in the binding of neutralizing antibodies (Sadeyen et al., Virology 2003; 309:32-40; White et al., J Virol 1999; 73:4882-89; Combita et al., J Virol 2002; 76:6480-86; Carter et al., J Virol 2003; 77:11625-32).

The aim of this study was to investigate the immunogenicity of chimeric HPV particles. We substituted amino acid in the L1 capsid protein FG external loop harboring major epitopes of HPV16 (aa256-294) with corresponding amino acids of the L1 FG loop of HPV31 (aa257-295) generating chimeric L1 HPV nanoparticles that maintained the overall wild-type sequence of HPV16 L1 with only 3 HPV31-like substitutions (HPV-VLP X) or 7 HPV31-like substitutions (HPV-VLP Y) in the FG loop (FIG. 13).

The chimeric L1 proteins were produced and purified from Sf21 insect cells infected with recombinant baculoviruses. Sf21 insect cells produced a good yield of the chimeric L1 proteins (2.5-3 mg/liter). L1 HPV X and L1 HPV Y chimeric proteins assembled similarly to HPV 16 wild-type L1 into VLP. Chimeric constructs harboring mutations in addition to the 7 exchanges made in HPV-VLP Y did not assemble into VLPs.

To test the infectiousness of the chimeric VLPs their ability to transfer genetic material into cells was assayed. HPV-VLP X and HPV-VLP Y and as a control HPV16 wild-type VLP were dissociated and a luciferase reporter plasmid was added and packaged in the VLPs upon re-association. The COS-7 cells (African green monkey kidney cells, ATCC CRL-1651) were contacted with VLPs in vitro and incubated. After incubation the culture media was removed, the cells were washed and lysed in luciferase lysis buffer. As shown FIG. 14, the chimeric HPV-VLPs X and Y retain the infections capabilities of wild-type HPV-16 VLP.

To test the immunogenicity of the chimeric VLP mice (ten per group) were immunized with HPV16, HPV31 and the two chimeric HPV X and Y. As shown FIG. 15, the immunoreactivity of the HPV-VLP chimera is of same order of magnitude as cross-reactivity between HPV16 and HPV31, which is minimal (at least 2 logs less than an actual immune response). In mice immunized with HPV16, HPV16-specific antibody titers, as measure by ELISA, are about 2000 GMT, which would be expected. Surprisingly, in HPV-VLP X and Y infected mice essentially no HPV16-specific antibodies are found, despite the fact that L1 HPV-VLP X and Y maintain almost entirely the HPV16 wild-type amino acid sequence. Thus, these chimeras do not raise HPV16-specific antibodies. As expected, in HPV31 infected mice essentially no HPV16-specific antibodies can be found. An even more surprising finding was that in HPV-VLP X and Y infected mice essentially no HPV31-specific antibodies are found, despite the fact that the FG loop of the chimera resembles that of HPV31, particularly for the FG loop of L1 HPV Y, which differs from the FG loop of wild-type HPV31 by just one amino acid (HPV 31 291T-N290 HPV16). As expected, in HPV16 infected mice essentially no HPV31-specific antibodies can be found, while a solid response is seen for HPV31 (around 1900 GMT). Interestingly, X and Y-specific antibodies are also not detectable in HPV16 or HPV31-immunized mice, suggesting that there is essentially no cross-reactivity. Moderate cross-reactivity is detectable for X and Y in X or Y immunized mice (538 vs 857 GMT for X and Y, respectively).

The data show that it is possible to design pseudovirion vectors with mutations that are virtually non-crossreactive with the species that they are derived from. This much reduced immunogenicity will allow re-administration of these vectors without a dramatic loss of transgene efficacy due to induction of neutralizing antibodies against the vector in HPV-infected individuals.

Example 4

Induction of Neutralizing Antibodies Against Heterologous HPV by Immunization with HPV Pseudovirions Packaged with the L2 Gene Immunization with L1 self-assembled into virus-like particles (VLPs) induces high titers of neutralizing antibodies and confers protection in animals against homologous experimental infection [Breitburd et al., J Virol 1995; 69(6): 3959-63; Suzich et al., PNAS 1995; 92(25):11553-7]. It has been also shown that protection is mediated by neutralizing antibodies directed against conformational epitopes. These results have led to the industrial development of vaccines against genital HPV types. Pre-clinical studies have shown that the neutralizing antibodies induced by L1 VLPs are predominantly type-specific [Roden et al., J Virol 1994; 68(11):7570-4; Roden et al., J Virol 1996; 70(9):5875-83]. However, low levels of cross-neutralization have been reported between HPV6 and 11 and HPV 16 and 31 [Christensen et al., Virology 1994; 205(1):329-35; White et al., J Virol 1998; 72(2):959-64; Giroglou et al., Vaccine 2001; 19(13-14):1783-93; Combita et al., J Virol 2002; 76(13): 6480-6] and higher levels between HPV18 and 45 [McLaughlin-Drubin et al., Virology 2003; 312(1):1-7]. Clinical trials have shown that the immune response is associated with protection against HPV16 and HPV18 infections and associated lesions [Ault et al., Lancet 2007; 369(9876):1861-8; Paavonen et al., Lancet 2007; 369 (9580):2161-70]. Current HPV vaccines containing L1 VLPs promote the generation of a strong, mainly type-specific neutralizing antibody response. Clinical trials with HPV16 and 18 vaccines have also revealed that cross-protection against HPV types is limited to closely related types. Protection against HPV31 was clearly established for both vaccines and protection against HPV45 infection for only one vaccine [Paavonen et al., Lancet 2007; 369(9580): 2161-70; Brown et al., J Infect Dis 2009; 199(7):926-35]. As the licensed HPV vaccines target only two of the high-risk HPV types, additional strategies to prevent infection of other high-risk HPV types are required.

The L2 protein has emerged as a candidate prophylactic vaccine, since immunization with L2 in animal models of papillomavirus infection induces cross-neutralizing antibodies that are able to mediate broader protection than L1 VLPs [Roden et al., J Virol 1994; 68(11):7570-4; Christensen et al., Virology 1991; 181(2):572-9; Yin et al., Virology 1992; 187(2):612-9; Chandrachud et al., Virology 1995; 211(1): 204-8; Gaukroger et al., J Gen Virol 1996; 77(7):1577-83; Campo et al., Virology 1997; 234(2):261-6; Roden et al., Virology 2000; 270(2):254-7; Embers et al., J Virol 2002; 76(19):9798-805], and preclinical andclinical findings [Gambhira et al., Cancer Res 2006; 66(23):11120-4; Alphs et al., PNAS 2008; 105(15):5850-5; Karanam et al., Vaccine 2009; 27(7):1040-9] have confirmed that L2 vaccines induce broad-spectrum crossneutralizing antibodies. However, L2 protein and L2 peptides are less immunogenic than L1 VLPs, and the incorporation of the L2 protein into L1 VLPs does not increase the anti-L2 response due to the immunodominance of L1 [Roden et al., Virology 2000; 270(2): 254-7]. This suggests that new vaccine strategies have to be investigated if such an L2 based vaccine is to be effective.

The aims of this study were to investigate the possibility of increasing exposure of L2 protein to the immune system to generate a broad-spectrum HPV vaccine.

Materials and Methods

Antibodies

CamVir-1 monoclonal antibody (BD Biosciences, Le Pont de Claix, France) binds to a linear epitope which has been mapped between amino acids 203 to 209 of the HPV-16 μl protein [Fleury et al., Arch Virol 2006; 151(8): 1511-23]. H16.V5 MAb is directed against a conformational neutralization epitope of the HPV16 L1 protein [Christensen et al., Virology 1996; 223(1):174-84]. Rabbit anti-HPV16 L2 immune sera was kindly provided by Richard Roden.

StrepTag II Antibody (HRP conjugated) was used to detect the presence of StepTagII peptide on HPV VLPs (Novagen, VWR, Fontenay sous Bois, France).

Cell Lines

COS-7 cells (African green monkey kidney cells, ATCC CRL-1651) were grown in Dulbecco's modified Eagle's Medium (Invitrogen, Illkirch, France) supplemented with 10% heat-inactivated fetal calf serum (FCS), 100 IU/ml penicillin, and 100 µg/ml streptomycin and 1 mmol/L sodium pyruvate. The 293FT cell line (Invitrogen) is a fast growing variant of the 293 cell line that stably expresses SV40 TAg and the neomycin resistance gene from pCMVPORT6AT.neo plasmid. 293FT cells were grown in Dulbecco's modified Eagle's Medium supplemented as above plus 1% non-essential amino acids and 500 µg/ml G418. Cell lines were grown at 37° C. in a humidified atmosphere with 5% $CO_2$.

Production of HPV18, HPV31 and HPV58 VLPs in Insect Cells

HPV58 L1/L2 VLPs, HPV31 L1/L2 VLPs and HPV18 L1/L2 VLPs were produced and purified from Sf21 insect cells infected with recombinant baculoviruses encoding both L1 and L2 gene as previously described Touze et al., J Clin Microbiol. 1998; 36(7):2046-51; Combita et al., FEMS Microbiol Lett 2001; 204(1):183-8].

Production and Purification of L2 Streptactin Fusion Protein (L2SA)

The Streptactin (SA) sequence without start codon [Voss et al., Protein Eng 1997; 10(8):975-82] including upstream (BamHI and SalI) and downstream (HindIII) restriction sites was synthesised by Geneart (Regensburg, Germany) using an adapted codon usage for expression in *Spodoptera frugiperda*. The SA sequence was cloned between SalI and HindIII sites of the pFastBacDual expression vector (Invitrogen) in order to obtain the pFastBacDual SA plasmid. The HPV16 L2 ORF was then fused at the 5' end of the SA ORF. For this purpose, the HPV16 L2ΔNLS ORF (amino acids 12 to 442) was amplified by PCR from a plasmid containing a *Homo sapiens* codon adapted version of the wild type L2 gene (FN297862) using HPV16 L2 F and HPV16 L2Δ R. A forward primer was designed to introduce a BamHI site, and a Kozak sequence upstream from the start codon and the reverse primer contained a SalI restriction site. The PCR product was then cloned by TA cloning into the pCR2.1 vector (Invitrogen). The absence of unwanted PCR-induced mutagenesis was then verified by sequencing. Both pCR2.1-16 L2ΔNLS and pFastBacDual SA plasmids were submitted to restriction with BamHI and SalI and the L2 gene was fused to the Streptactin gene in order to generate the pFastBacDual-16 L2ΔNLS (L2SA).

A recombinant baculovirus encoding L2SA was generated using the Bac-to-Bac system (Invitrogen) according to the manufacturer's recommendations. Sf21 insect cells were grown at 27° C. in SF900II medium supplemented with penicillin, streptomycin and amphotericin B (Invitrogen). Cells were infected at a m.o.i. of ten and grown for four days. Cells were scraped off, centrifuged at 300×g and then resuspended in PBS 1× containing 0.5% Nonidet P40 and an anti-protease cocktail (Roche, Meylan, France) and incubated on ice for 30 min. The lysate was centrifuged at 4° C. for 10 min at 12,000×g, and the supernatant represented the cytoplasmic fraction. The pellet, representing the nuclear fraction, was subjected to sonication (3 bursts, 15 s, Vibracell, Fischer Scientific, France). Expression of L2SA protein was analyzed by Western-blotting. For this purpose, proteins were separated by 12.5% SDS PAGE and transferred to nitrocellulose membrane (Protran BA83, Schleicher and Schuell, Mantes la VIIIe, France). The membrane was saturated overnight at 4° C. in TNT (15 mmol/L Tris, 140 mmol/L NaCl, 0.05% Tween 20) containing 5% low fat dried milk and then washed three times with TNT-5% milk. Membranes were incubated for 1 h at room temperature with rabbit polyclonal anti-L2, diluted 1/1000 in TNT-5% milk, then washed three times and alkaline phosphatase-conjugated goat anti-mouse IgG Fc (Sigma Aldrich) (1/2,500 in TNT-5% milk) was added. After incubation for 1 h at room temperature and three washes in TNT-5% milk plus two washes in TNT, the immunoblots were developed using the BCIP/NBT liquid substrate system (Sigma-Aldrich, Saint Quentin Fallavier, France). L2SA protein was purified by affinity on immobilized iminobiotin according to the manufacturer's instructions (Pierce, Ozyme, Montigny le Bretonneux, France).

Production of L1L2SA VLPs

The L1 16-StepTagII gene was constructed after two PCR steps using primers permitting the insertion of StepTagII peptide (STII, WSHPQFEK, SEQ ID NO: 12) [Schmidt et al., Nat Protoc 2007; 2(6):1528-35] at position 140-141 of the wild type HPV 16 L1 capsid gene as previously described [Sadeyen et al., Virology 2003; 309(1):32-40]. In the first PCR step, For L116 STII/reverse STII and forward STII/rev L116 STII were used with a HPV16 L1 gene presenting a humanized codon usage as template. The two overlapping fragments thus obtained were fused in a second PCR step using For L116 STII/rev L116 STII primers in order to generate the L1 16 StrepTagII sequence (L1STII). The final PCR product was cloned and sequenced as above and finally cloned between BamHI and HindIII of the pFastBacDual plasmid to generate a recombinant baculovirus.

VLPs were purified from infected insect cells by ultracentrifugation on CsCl gradient. L2SA protein binding to L1STII VLPs was obtained by mixing L1STII VLPs with L2SA fusion proteins in the interaction buffer (100 mmol/L Tris HCl pH 8, 1M Nacl, 0.25% Triton X100). To analyze the chimeric VLPs obtained (L1L2SA VLPs), VLPs were pelleted by ultracentrifugation (60,000 rpm, 1 h) in a SW-60 rotor (Beckman) and then analyzed according to the presence of L2 and Strep-Tag by Western blotting as above.

Production of HPV 31 VLPs with the HPV31 L2 Peptide (13-88) Inserted into the DE Loop The cross-neutralizing epitope (amino acids 13-88) of the HPV31 L2 protein was selected for insertion within the L1 protein [Pastrana et al., Virology 2005; 337(2):365-72; Gambhira et al., J Virol 2007; 81(21):11585-92; Richards et al., PNAS USA 2006; 103(5):1522-7]. The sequence of HPV 31 L1 gene containing restriction site XhoI and SmaI at position 140-141 was constructed by two PCR steps [Fleury et Clin Vaccine Immunol 2008; 15(1):172-5] in order to insert the HPV 31 L2 peptide sequence 13-88 (L213-88) using pIRES31L1L2h. In the first PCR step the 5' and 3' parts of HPV L131 were amplified using forward-L1h31/reverse-L1 and reverse-L1h31/forward-L 1 as primers. These two fragments were used as template in the second PCR step using forward-L1h31/reverse L1h31 as primer. This PCR product was then cloned into pCR TOPO 2.1, sequenced and subcloned into pFastBac1 plasmid previously digested by BamHI and HindIII. DNA encoding fragment 13-88 of the HPV 31 L2 gene was amplified from pIRES31L1L2h and L213-88 forward and reverse primers and cloned as above. Both pCR 2.1 TOPO/L213-88 and pFastBac1/L1 were digested by XhoI/SmaI in order to insert the sequence encoding the HPV L2 peptide. A recombinant baculovirus encoding the L1-L213-88 protein was generated and insect cells were infected as above.

were transfected with 0.5 μg DNA (0.25 μg pGL3-Luc, or pCMV-GFP or pIRES-L2 plasmid, 0.25 μL1 L2 plasmid)

TABLE 5

Sequence of oligonucleotides used

| Name | Primer (5' → 3') | Restriction site |
|---|---|---|
| for L116 STII | GGATCCCACCATGAGCCTGTGGAGACCCAGC (SEQ ID NO: 51) | BamHI |
| rev L116 STII | AAGCTTTCACTTCTTGGTTTTCTTCCGCTTG (SEQ ID NO: 52) | HindIII |
| Rev STII | CTTCTCGAACTGGGGGTGGCTCCAGTTCTCGGTGTCGTCCAGCTTGTTC (SEQ ID NO: 53) | |
| For STII | TGGAGCCACCCCCAGTTCGAGAAGGCCAGCGCCTACGCCGCCAACGCC (SEQ ID NO: 54) | |
| Rev-L1h31 | AAGCTTTCACTTCTTGGTTTTCTTCCGCTTG (SEQ ID NO: 55) | HindIII |
| For-L1h31 | GGATCCCACCATGAGCCTGTGGAGACCCAGC (SEQ ID NO: 56) | BamHI |
| rev-L1 | CGGGTCTAGAGAATTCTCGAGAGGGCCTCCGGCGTATCTGTTGC SEQ ID NO: 57) | SmaI |
| for-L1 | CTCGAGAATTCTCTAGACCCGGGCACCGATAACAGGGAGTGC (SEQ ID NO: 58) | XhoI |
| rev-L2 | CCCGGGGGCCAGGGTGTCGGTGGCGGT (SEQ ID NO: 59) | SmaI |
| for-L2 | CTCGAGGCCAGCGCCACCCAGCTGTACAAG (SEQ ID NO: 60) | XhoI |
| HPV16 L2Δ R | GTCGACCATGTAGTAGCTGGGGTGCAGGATG (SEQ ID NO: 61) | SalI |
| HPV16 L2 F | CCGGATCCGCCACCATGGCCAGCGCCACCCAGCTG (SEQ ID NO: 62) | BamHI |
| for L231ΔNLS | CCCTCTAGAGCCACCATGGCCAGCGCCACCCAGCTGTAC (SEQ ID NO: 63) | XbaI |
| rev L231ΔNLS | GCGGCCGCTATCACAGGATGTAGTAGCTGGGGTGCAG (SEQ ID NO: 64) | NotI |

Production of HPV58 and HPV31 Pseudovirions

HPV31 and 58 pseudovirions were obtained using a cellular system with codon-modified HPV capsid genes [Bucki et al., Methods Mol Med 2005; 119:445-62]. Briefly, HPV 58 L1 and L2 genes were designed to contain the most frequently used codons found in highly expressed genes in *Homo sapiens* (FN178626 and FN178627, respectively). L1 and L2 genes were cloned into the mammalian bicistronic expression vector pIRES (BDBiosciences, Clontech). The L1 gene was cloned between the NheI and EcoRI restriction sites of MCS A downstream from the CMV IE promoter. The L2 gene was subsequently cloned between the XbaI and NotI restriction sites of MCS B of pIRES-L1. DNA plasmid encoding luciferase (pGL3 luc, Promega, Charbonnières-les-Bains, France) or pIRES L2 ΔNLS used for the production of pseudovirions was prepared by classical phenol/chloroform DNA preparation. The latter plasmid contains the DNA sequence encoding amino acids 12 to 442 of the HPV31 L2 between the XbaI and NotI restriction sites. This sequence was PCR-amplified from a plasmid containing a *Homo sapiens* codon-adapted HPV31 full length L2 gene [Fleury et al., Clin Vaccine Immunol 2008; 15(1):172-5]. For the generation of pseudovirions in 293FT cells, cells and 1 μl Fugene6 (Roche) per cm2 of the culture area. Cells were harvested two days post transfection and pseudovirions were purified as previously described [Fleury et al., Clin Vaccine Immunol 2008; 15(1):172-5] and stored at −80° C. until use. Amounts of pseudovirions were determined by western blotting using CamVir-1 antibody by comparison with known concentrations of VLPs of homologous types.

Production of HPV16 and 18 Pseudovirions

HPV16 and 18 pseudovirions were produced by the previously published disassembly-reassembly method [Touze et al., Nucleic Acids Res 1998; 26(5):1317-23] with some modifications [Bousarghin et al., Mol Cancer Ther 2009; 8(2):357-65]. L1/L2 VLPs (100 μg) were incubated in 50 mmol/L Tris-HCl buffer (pH 7.5) containing 20 mmol/L DTT and 1 mmol/L EGTA for 30 min at room temperature. At this stage, pGL3 luc (10 μg) was added to the disrupted VLPs. The preparation was then diluted with increasing concentrations of $CaCl_2$ (up to a final concentration of 5 mmol/L) and in the presence of 10 nM $ZnCl_2$. Pseudovirions were then dialyzed against PBS 1× overnight and stored at 4° C. before use.

Immunization Protocol.

Six-week-old female BALB/c mice (CERJ Janvier, Le Genest St Isle, France) were intramuscularly immunized with the different vaccine preparations. Mice from group 1 received saline, mice from groups 2 to 5 received 10 µg of HPV 16 L2-SA protein (L2SA), L1STII-L2SA (L1L2SA VLPs), HPV16 L1L2 (L1L2 VLPs) with or without aluminium hydroxide, respectively. Mice from groups 6 and 7 received 1 or 10 µg of pIRES-HPV31 L2ΔNLS plasmid (DNA L2), respectively. Mice from groups 8 to 10 received HPV31 L1, HPV31 L1-31 L213-88 VLPs (L1/L2(13-88) VLPs), HPV31 L1L2 VLPs (31 L1L2 VLPs), respectively. Mice from group 11 received 10 µg of HPV31 pseudovirions containing HEV ORF2108-660 expression plasmid (HEV PsV). Mice from groups 12 and 13 received HPV58 pseudovirions containing GFP expression plasmid (GFP PsV), and HPV58 pseudovirions packaged with HPV31L2ΔNLS plasmid (L2 PsV), respectively. The quantity of L1 protein was adjusted between the different L1L2 VLPs and pseudovirions by Western Blot analysis. Mice were immunized at days 0, 7 and 21. Two weeks after the last injection, serum samples were collected and stored at −20° C. All animal procedures were performed according to approved protocols and in accordance with the recommendations for the proper use and care of laboratory animals, and experiments were approved by the regional animal ethics committee (CREEA Centre Limousin).

Determination of Anti-HPV Serum Titers by ELISA

Two hundred nanograms of VLPs were distributed in half of the wells of a 96-well plate (Maxisorp, Nunc, ATGC, Marne-la-Vallée, France) and incubated at 4° C. overnight. After two washes with PBS-Tween (0.1%), the wells were saturated with PBS supplemented with 1% FCS for 1 h at 37° C. Duplicate wells (one test and one control) were incubated with two-fold dilutions (starting at 1:25) of mice sera in dilution buffer (PBS 5×, 1% Tween, 10% FCS) for 1 h at 45° C. After four washes, peroxidase-conjugated goat anti-mouse IgG (Fc specific) (Sigma Aldrich) diluted 1:1,000 in PBS—Tween (1%)—FCS (10%) was added to the wells and incubated for 1 h at 45° C. After four washes, 0.4 mg/ml o-phenylene-diamine and 0.03% hydrogen peroxide in 25 mmol/L sodium citrate and 50 mmol/L $Na_2HPO_4$ were added. After 30 min, the reaction was stopped with $H_2SO_4$ 4N and optical density (OD) was read at 492 nm. For data analysis, OD values obtained in the absence of L2 were subtracted from OD values of test antigens. A result was considered positive when the difference in OD between test and control wells was greater than 0.2. Individual titers represented the reciprocal of the last dilution giving an OD difference greater than 0.2. Values for individual mice were the means of duplicates. Geometric mean titers (GMTs) were calculated for each group. Animals without detectable antibody titers (<25) were assigned a titer of 1 for calculation of GMTs. For the detection of anti-L2 antibodies the same ELISA as above was performed with the difference that purified L2SA protein was added to each well of the Nunc plates in place of the VLPs.

Detection of L1, L2 and Strep-Tag Motifs by ELISA.

L1 antigenicity of chimeric VLPs and the presence of L2 or Strep-Tag motifs on the surface of the VLPs were analyzed by ELISA. Microtiter plate wells were coated at 4° C. overnight with 200 ng of VLPs. ELISAs were performed as above using an anti-StrepTagII monoclonal antibody or a polyclonal anti-L2 antibody for investigation of the presence of the StrepTagII motif and the L2 protein on the surface of the VLPs, respectively, or H16.V5 and H31.F16 Monoclonal Antibodies to Investigate the Presence of the Conformational Epitopes of HPV 16 and HPV 31 µl proteins, respectively.

HPV16, 18, 31 and 58 Pseudovirion Neutralization Assays

Neutralization assays were performed by inhibition of pseudoinfection of COS-7 cells by pseudovirions containing pGL3-luc plasmid. COS-7 cells (104/well) were seeded in 96-well plates (TPP, ATGC). After 24 h incubation at 37° C., cells were washed twice before addition of pseudovirion/diluted sera mixture. The amount of pseudovirions was adjusted to obtain a relative luciferase activity of 0.2 RLU (Luminoskan Ascent, Thermo scientific, Courtaboeuf, France) (1:500 for HPV16, 1:50 for HPV 18, 1:800 for HPV31, and 1:10,000 for HPV 58) and 500 of diluted pseudovirions were mixed with 50 µl of mice sera diluted by two fold dilution in incomplete DMEM from 1:25 to 1:51,200. After 1 h incubation at 37° C., the mixture was added to the wells. After 3 h at 37° C., 100 µl of complete DMEM were added.

After incubation at 37° C. for 48 h, the luciferase gene expression was measured (Firefly luciferase 1-step assay kit, Fluoprobes, Interchim, Montlucon, France). The results were expressed as the percentage of inhibition of luciferase activity [Richards et al., PNAS USA 2006; 103(5):1522-7]. The data presented are the means of 2 to 3 determinations performed in duplicate. Neutralization titers were defined as the reciprocal of the highest dilution of mice sera that induced at least 50% reduction in luciferase activity. Geometric mean titers were calculated for each group. Animals without detectable neutralizing antibodies were assigned a titer of 1 for the calculation of GMTs. HPV16-neutralizing antibodies were only investigated in groups 10, 12 and 13.

Statistical Analysis

Individual antibody titers and geometric mean titers were compared to evaluate ELISA and neutralizing responses. Group results (10 animals per group) were compared by Student's t test using XLStat software (Addinsoft, Paris, France).

Results

Production of HPV31 L2 and HPV16 L2 Chimeric Particles and HPV58 Pseudovirions Coding for L2

Figure 16:
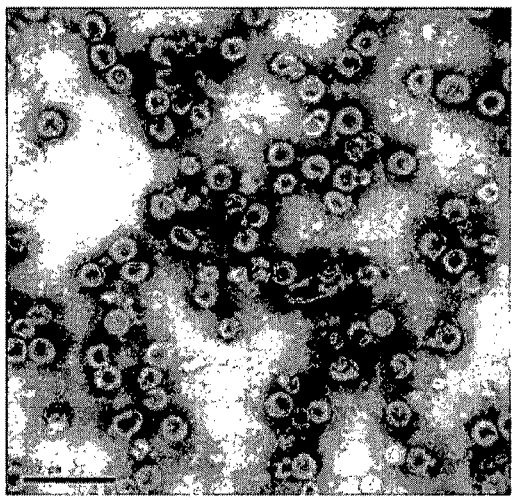
Figure 16:
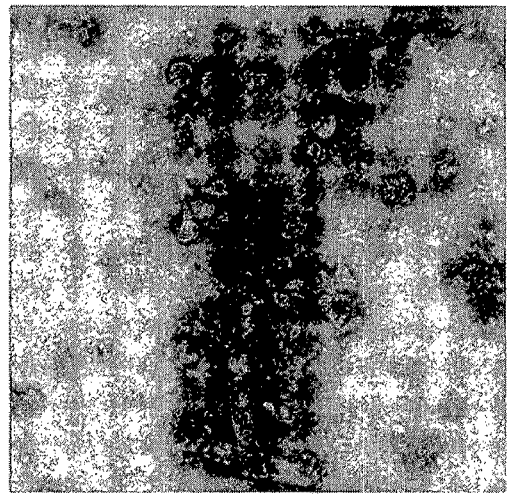

We produced two chimeric L1-L2 particles to investigate the potential of L2 vaccines to protect against a broad spectrum of HPV types. In order to decorate the outside of the capsid with L2, the first was based on the interaction between an HPV16 L1 modified VLP protein and an HPV16 L2 protein fused to streptactin, an engineered version of streptavidin. To achieve this, the StrepTagII peptide (WSH-PQFEK, SEQ ID NO: 12), a sequence that mimics the biotin binding loop, was inserted into the DE loop between positions 140/141 of the L1 protein to avoid chemical coupling of biotin to L1 VLP with the risk of coupling biotin to L1 neutralizing epitopes. When expressed in Sf-21 insect cells using recombinant baculoviruses and purified on CsCl gradients, the L1STII recombinant protein self-assembled into virus-like particles with the same appearance and at a similar yield as wild-type L1 protein (FIG. 16). Slides were negatively stained with uranyl acetate and observed by transmission electron microscopy at 50 000× magnification (bar=200 nm).

The second chimeric L1/L2 protein contained the HPV31 L2 peptide (aa 13-88) inserted within the DE loop of the HPV31 L1 protein. When expressed in insect cells using recombinant baculoviruses, the L1L2(13-88) recombinant protein did not allow the production of well-shaped VLPs, but resulted mainly in aggregates of proteins and/or capsomeres (FIG. 16).

Figure 17:
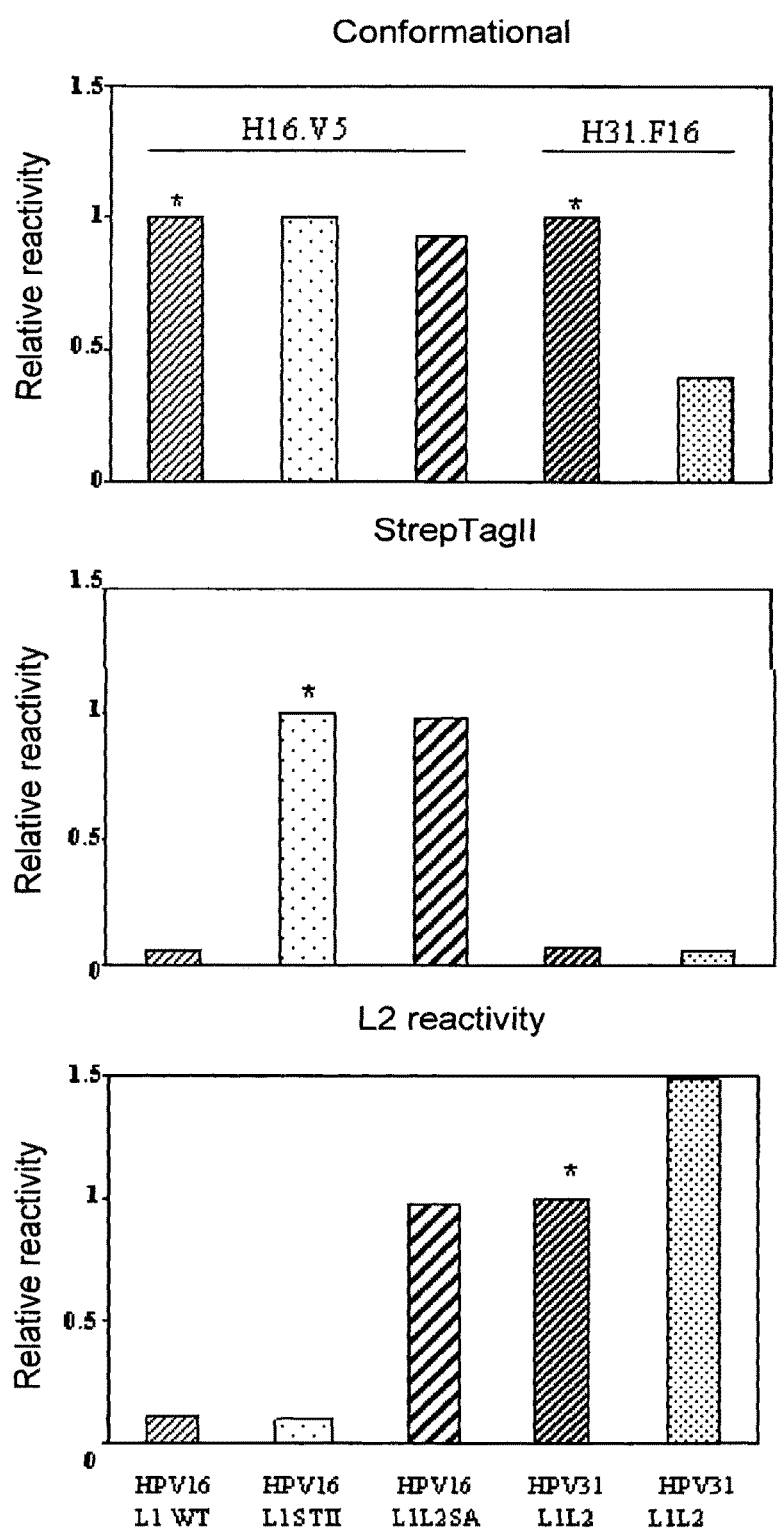

The L1 antigenicity of these two chimeric VLPs was investigated by ELISA using anti-L1 MAbs directed against conformational and linear epitopes (FIG. 17). The results indicated that the conformational L1 epitope recognized by H16.V5 on chimeric HPV16 L1STII VLPs was not affected. However, a clear reduction in H31.F16 MAb binding to HPV31 L1-L213-88 VLPs was observed compared to that observed with HPV31 L1 VLPs. The presence of StrepTagII or L2 peptide (13-88) on the surface of the VLPs was also investigated by ELISA using a MAb directed against the StrepTagII sequence or a polyclonal anti-L2 antibody, respectively. The results obtained (FIG. 17) showed that the StrepTagII and L2 sequences were present on the surface of the chimeric VLPs.

Figure 18:
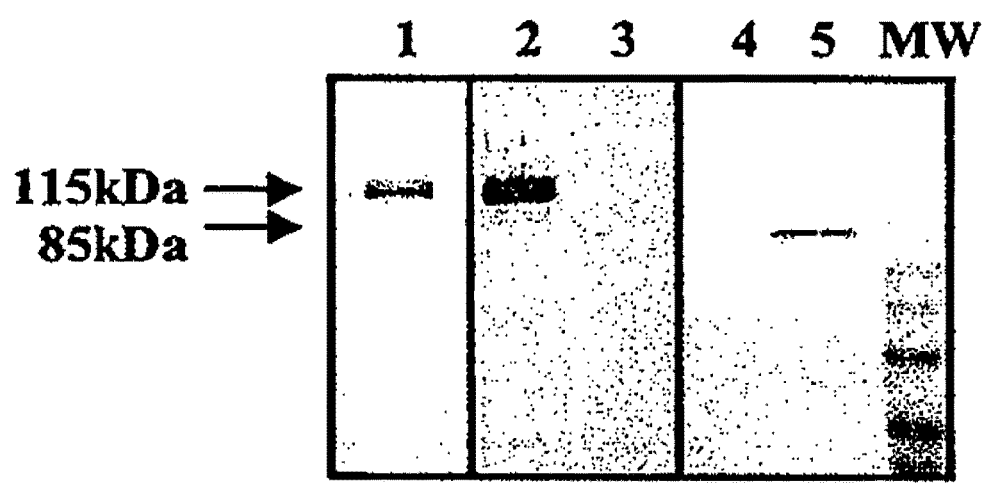

In addition, the ability of L1STII VLPs to bind to L2SA protein was determined by mixing 5 μg of the VLPs with 10 μg of L2SA fusion protein corresponding to a mass ratio of 1/1 (one L2SA protein/one L1 protein). The binding of L2SA to L1STII VLPs was analyzed by ultracentrifugation of the complexed VLPs followed by the detection of L2SA protein by western blotting. The detection of L2SA and L1STII VLPs in the ultracentrifugation pellet (FIG. 18) indicated that L2SA protein was effectively bound to the VLPs. Binding was not observed when L2SA was mixed with wild-type HPV16 VLPs. The presence of L2 protein in the L 1L2SA VLPs was also evidenced by ELISA (FIG. 17). HPV 58 pseudovirions packaged with a plasmid encoding the HPV-31 L2ΔNLS gene were produced in 293 FT cells. Their ability to transduce the L2 gene was investigated by infection of COS-7 cells. Western Blot analysis of L2 protein expression indicated that L2 was detected two days after transduction (FIG. 18). In order to rule out the possibility that L2 detected in COS-7 cells was due to the presence of the input pseudovirions, COS-7 cells were transduced with similar pseudovirions packaged with the GFP gene. The presence of L2 was not evidenced in these conditions (FIG. 18).

Anti-HPV16-L2 Immune Response in Mice Immunized with Chimeric VLPs and Pseudovirions.

Anti-HPV16 L2 antibodies were not detected in non-immunized mice (group 1). In mice receiving the L2SA protein (group 2) an anti-L2 GMT of 348 was observed (Table 6). An increase in anti-L2 antibody levels was observed in mice immunized with the HPV16 L1L2SA VLPs and HPV16 L1L2 VLPs (groups 3 and 4), with GMTs of 1,160 and 1,055 (p=0.035 and p=0.05), respectively. Addition of aluminium hydroxide as adjuvant to HPV16 μL2 VLPs (group 5) further increased the level of homologous anti-L2 antibodies in a non-significant manner (p=0.247).

Anti-L2 were not detected in mice immunized with HPV31 L1 VLPs (group 8), but in all mice immunized the L1L213-88 VLPs (group 9) with a GMT of 730, and at a higher level in mice immunized with the LIL2 VLPs (group 10) with a GMT of 1,100 (p=0.189). Anti-L2 antibodies were detected at similar levels in mice immunized with control pseudovirions (group 11 and 12) with GMT of 855 and 1,212 (p=0.459). By comparison with these control pseudovirions, the anti-L2 GMT (2,600) was higher in mice immunized with pseudovirions coding for L2 (p=0.001 and p=0.101, respectively).

TABLE 6

| Lot No. | Name | Vaccines L1 | Vaccines L2 | Anti-L2 | Neutralizing Titers HPV18 | Neutralizing Titers HPV31 | Neutralizing Titers HPV58 |
|---|---|---|---|---|---|---|---|
| 1 | Saline | — | — | — | — | — | — |
| 2 | L2SA | — | 16 | 348 | — | — | — |
| 3 | L1L2SA VLPs | 16 | 16 | 1,600 | — | — | — |
| 4 | L1L2 VLPs | 16 | 16 | 1,055 | — | — | — |
| 5 | L1L2 VLPs + Adj. | 16 | 16 | 2,064 | — | 85 | — |
| 6 | DNA L2 (1 μg) | — | 31 | — | — | — | — |
| 7 | DNA L2 (10 μg) | — | 31 | — | — | — | — |
| 8 | L1 VLPs | 31 | — | — | — | 2,800 | — |
| 9 | L1L2$_{(13-88)}$ VLPs | 31 | 31 | 730 | — | — | — |
| 10 | L1L2 VLPs | 31 | 31 | 1,100 | — | 3,400 | 65 |
| 11 | HEV PsV | 31 | 31 | 855 | — | 5,198 | 54 |
| 12 | GFP PsV | 58 | 58 | 1,212 | — | 50 | 4,650 |
| 13 | L2 PsV | 58 | 58/31 | 2,600 | 400 | 733 | 5,382 |

Induction of Neutralizing Antibodies Against HPV18, HPV31 and HPV58

None of the mice immunized with HPV16 L2SA protein or HPV16L1L2 VLPs (groups 3 to 5) developed neutralizing antibodies against heterologous HPV types (HPV18, HPV31 and HPV58) (Table 6). Low levels of neutralizing antibodies against HPV31 (GMT 85) were only detected when aluminium hydroxide was added to the HPV16 VLPs obtained by self-assembly of L1 and L2 proteins (group 5).

In mice immunized with HPV31 L1 or HPV31 L1 L2 VLPs and HPV31 HEV PsV (groups 8, 10 and 11), homologous HPV31 neutralizing antibodies were detected, with GMTs of 2,800, 3,400 and 5,198, respectively (FIG. 19). Low titers of HPV58 neutralizing antibodies were only observed in mice receiving HPV31 L1L2 VLPs (group 10) and HPV31 pseudovirions containing the HEV ORF2 irrelevant gene (group 11). No neutralizing antibodies against HPV18 were detected in any of the mice from groups 8 to 11 receiving HPV31 vaccine preparations.

High levels of homologous neutralizing antibodies were detected in mice immunized with HPV58 pseudovirions (groups 12 and 13) with GMTs of 4,650 and 5,382, respectively. Low levels of neutralizing antibodies to HPV31 (GMT=50) were detected in mice immunized with pseudovirions coding for GFP, and a dramatic increase in anti-HPV31 neutralizing antibodies (with a GMT of 733) was observed in mice immunized with HPV58 pseudovirions coding for the HPV31 L2 protein. Neutralizing antibodies against HPV18 were only detected in mice immunized with the HPV58 L2 PsV, with a GMT of 400. Mice from groups 10, 12 and 13 were also investigated for HPV16 neutralizing antibodies. Mice immunized with HPV31 L1 L2 VLPs developed low levels of HPV16 neutralizing antibodies, with a GMT of 40. HPV16 neutralizing antibodies were not detected in mice immunized with HPV58 PsV coding for GFP (group 12) but were detected in mice immunized with HPV58 PsV coding for L2 (group 13) with a GMT of 60.

Patents, patent applications, and scientific publications and references are incorporated by reference herein in their entirety.

What is claimed is:

1. A method of delivering one or more heterologous compounds to a subject, the method comprising
   administering to the subject a nanoparticle that comprises one or more heterologous compounds and a modified human papilloma virus (HPV) L1 protein having reduced immunogenicity relative to wild-type HPV16, wherein the amino acid sequence of the modified HPV L1 protein corresponds to the amino acid sequence of SEQ ID NO: 1 comprising amino acid substitutions D273T, N285T and S288N.

2. A method of administering one or more heterologous compounds to a subject, the method comprising:
   administering a first nanoparticle that comprises one or more heterologous compounds to the subject for a first period of time, and
   administering a second nanoparticle that comprises the one or more heterologous compounds to the subject for a second period of time, wherein the first and second nanoparticles have different serotypes, wherein the first nanoparticle and/or the second nanoparticle comprises a modified human papilloma virus (HPV) L1 protein having reduced immunogenicity relative to wild-type HPV16, wherein the amino acid sequence of the modified HPV L1 protein corresponds to the amino acid sequence of SEQ ID NO: 1 comprising amino acid substitutions D273T, N285T and S288N.

3. A composition for delivering one or more heterologous compounds to a subject, the composition comprising a nanoparticle that comprises one or more heterologous compounds and a modified human papilloma virus (HPV) L1 protein having reduced immunogenicity relative to wild-type HPV16, wherein the amino acid sequence of the modified HPV L1 protein corresponds to the amino acid sequence of SEQ ID NO: 1 comprising amino acid substitutions D273T, N285T and S288N.

4. The composition of claim 3, wherein the amino acid sequence of the modified HPV L1 protein further comprises amino acid substitutions L260F, A264S, A266T and N270S.

5. The method of claim 1, wherein the one or more heterologous compounds comprise one or more therapeutic and/or diagnostic agents.

6. The method of claim 2, wherein the compound comprises one or more therapeutic and/or diagnostic agents.

7. The method of claim 3, wherein the one or more heterologous compounds comprise one or more therapeutic and/or diagnostic agents.

8. The method of claim 1, wherein the amino acid sequence of the modified HPV L1 protein further comprises amino acid substitutions L260F, A264S, A266T and N270S.

9. The method of claim 2, wherein the amino acid sequence of the modified HPV L1 protein further comprises amino acid substitutions L260F, A264S, A266T and N270S.

10. The method of claim 1, wherein the nanoparticle is a self-assembled nanoparticle.

11. The method of claim 2, wherein the first and second nanoparticles are a self-assembled nanoparticles.

12. The method of claim 3, wherein the nanoparticle is a self-assembled nanoparticle.

13. A method of delivering one or more heterologous compounds to a subject, the method comprising
   administering to the subject a nanoparticle that comprises one or more heterologous compounds and a modified human papilloma virus (HPV) L1 protein having reduced immunogenicity relative to wild-type HPV16, wherein the amino acid sequence of the modified HPV L1 protein corresponds to the amino acid sequence of SEQ ID NO: 1 comprising an FG loop having amino acid substitutions that consist of D273T, N285T and S288N.

* * * * *

SEQUENCE LISTING

<160> NUMBER OF SEQ ID NOS: 65

<210> SEQ ID NO 1

<211> LENGTH: 39
<212> TYPE: PRT
<213> ORGANISM: artificial sequence
<220> FEATURE:
<223> OTHER INFORMATION: synthetic peptide

<400> SEQUENCE: 1

Phe Val Arg His Leu Phe Asn Arg Ala Gly Ala Val Gly Glu Asn Val
1               5                   10                  15

Pro Asp Asp Leu Tyr Ile Lys Gly Ser Gly Ser Thr Ala Asn Leu Ala
                20                  25                  30

Ser Ser Asn Tyr Phe Pro Thr
            35

<210> SEQ ID NO 2
<211> LENGTH: 39
<212> TYPE: PRT
<213> ORGANISM: artificial sequence
<220> FEATURE:
<223> OTHER INFORMATION: synthetic peptide

<400> SEQUENCE: 2

Phe Val Arg His Phe Phe Asn Arg Ser Gly Thr Val Gly Glu Ser Val
1               5                   10                  15

Pro Thr Asp Leu Tyr Ile Lys Gly Ser Gly Ser Thr Ala Thr Leu Ala
                20                  25                  30

Asn Ser Thr Tyr Phe Pro Thr
            35

<210> SEQ ID NO 3
<211> LENGTH: 39
<212> TYPE: PRT
<213> ORGANISM: artificial sequence
<220> FEATURE:
<223> OTHER INFORMATION: synthetic peptide

<400> SEQUENCE: 3

Phe Val Arg His Phe Phe Asn Arg Ala Gly Lys Leu Gly Glu Ala Val
1               5                   10                  15

Pro Asp Asp Leu Tyr Ile Lys Gly Ser Gly Thr Ala Ser Ile Gln
                20                  25                  30

Ser Ser Ala Phe Phe Pro Thr
            35

<210> SEQ ID NO 4
<211> LENGTH: 39
<212> TYPE: PRT
<213> ORGANISM: artificial sequence
<220> FEATURE:
<223> OTHER INFORMATION: synthetic peptide

<400> SEQUENCE: 4

Phe Val Arg His Leu Phe Asn Arg Ala Gly Thr Val Gly Asp Ala Ile
1               5                   10                  15

Pro Asp Asp Leu Met Ile Lys Gly Thr Gly Asn Thr Ala Ser Pro Ser
                20                  25                  30

Ser Cys Val Phe Tyr Pro Thr
            35

<210> SEQ ID NO 5
<211> LENGTH: 37
<212> TYPE: PRT
<213> ORGANISM: artificial sequence

```
<220> FEATURE:
<223> OTHER INFORMATION: synthetic peptide

<400> SEQUENCE: 5

Phe Val Arg His Leu Phe Asn Arg Ala Gly Thr Val Gly Glu Thr Val
1               5                   10                  15

Pro Ala Asp Leu Tyr Ile Lys Gly Thr Thr Gly Thr Leu Pro Ser Thr
            20                  25                  30

Ser Tyr Phe Pro Thr
        35

<210> SEQ ID NO 6
<211> LENGTH: 41
<212> TYPE: PRT
<213> ORGANISM: artificial sequence
<220> FEATURE:
<223> OTHER INFORMATION: synthetic peptide

<400> SEQUENCE: 6

Phe Val Arg His Phe Phe Asn Arg Ala Gly Thr Leu Gly Asp Pro Val
1               5                   10                  15

Pro Gly Asp Leu Tyr Ile Lys Gly Ser Asn Ser Gly Asn Thr Ala Thr
            20                  25                  30

Val Gln Ser Ser Ala Phe Phe Pro Thr
        35                  40

<210> SEQ ID NO 7
<211> LENGTH: 39
<212> TYPE: PRT
<213> ORGANISM: artificial sequence
<220> FEATURE:
<223> OTHER INFORMATION: synthetic peptide

<400> SEQUENCE: 7

Phe Val Arg His Phe Phe Asn Arg Ala Gly Lys Leu Gly Glu Ala Val
1               5                   10                  15

Pro Asp Asp Leu Tyr Ile Lys Gly Ser Gly Asn Thr Ala Val Ile Gln
            20                  25                  30

Ser Ser Ala Phe Phe Pro Thr
        35

<210> SEQ ID NO 8
<211> LENGTH: 39
<212> TYPE: PRT
<213> ORGANISM: artificial sequence
<220> FEATURE:
<223> OTHER INFORMATION: synthetic peptide

<400> SEQUENCE: 8

Phe Val Arg His Leu Phe Asn Arg Ala Gly Asp Thr Gly Asp Lys Ile
1               5                   10                  15

Pro Asp Asp Leu Met Ile Lys Gly Thr Gly Asn Thr Ala Thr Pro Ser
            20                  25                  30

Ser Cys Val Phe Tyr Pro Thr
        35

<210> SEQ ID NO 9
<211> LENGTH: 39
<212> TYPE: PRT
<213> ORGANISM: artificial sequence
<220> FEATURE:
<223> OTHER INFORMATION: synthetic peptide
```

```
<400> SEQUENCE: 9

Phe Val Arg His Phe Asn Arg Ala Gly Thr Thr Gly Asp Ala Val
1               5                   10                  15

Pro Lys Asp Leu Tyr Ile Ala Gly Thr Gly Asn Arg Ala Asn Ile Ala
            20                  25                  30

Gly Ser Ile Tyr Tyr Ser Thr
        35

<210> SEQ ID NO 10
<211> LENGTH: 41
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (11)..(11)
<223> OTHER INFORMATION: X = any amino acid
<220> FEATURE:
<221> NAME/KEY: MISC_FEATURE
<222> LOCATION: (15)..(15)
<223> OTHER INFORMATION: X = any amino acid
<220> FEATURE:
<221> NAME/KEY: MISC_FEATURE
<222> LOCATION: (18)..(18)
<223> OTHER INFORMATION: X = any amino acid
<220> FEATURE:
<221> NAME/KEY: MISC_FEATURE
<222> LOCATION: (26)..(27)
<223> OTHER INFORMATION: X = any amino acid or no amino acid
<220> FEATURE:
<221> NAME/KEY: MISC_FEATURE
<222> LOCATION: (32)..(34)
<223> OTHER INFORMATION: X = any amino acid
<220> FEATURE:
<221> NAME/KEY: MISC_FEATURE
<222> LOCATION: (37)..(37)
<223> OTHER INFORMATION: X = any amino acid

<400> SEQUENCE: 10

Phe Val Arg His Phe Asn Arg Ala Gly Xaa Val Gly Glu Xaa Val
1               5                   10                  15

Pro Xaa Asp Leu Tyr Ile Lys Gly Ser Xaa Xaa Gly Asn Thr Ala Xaa
            20                  25                  30

Xaa Xaa Ser Ser Xaa Phe Phe Pro Thr
        35                  40

<210> SEQ ID NO 11
<211> LENGTH: 41
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: X = any amino acid
<220> FEATURE:
<221> NAME/KEY: MISC_FEATURE
<222> LOCATION: (9)..(9)
<223> OTHER INFORMATION: X = any amino acid
<220> FEATURE:
<221> NAME/KEY: MISC_FEATURE
<222> LOCATION: (11)..(12)
<223> OTHER INFORMATION: X = any amino acid
<220> FEATURE:
<221> NAME/KEY: MISC_FEATURE
<222> LOCATION: (14)..(14)
<223> OTHER INFORMATION: X = E or D
<220> FEATURE:
<221> NAME/KEY: MISC_FEATURE
```

```
<222> LOCATION: (15)..(15)
<223> OTHER INFORMATION: X = any amino acid
<220> FEATURE:
<221> NAME/KEY: MISC_FEATURE
<222> LOCATION: (16)..(16)
<223> OTHER INFORMATION: X = V or I
<220> FEATURE:
<221> NAME/KEY: MISC_FEATURE
<222> LOCATION: (18)..(18)
<223> OTHER INFORMATION: X = any amino acid
<220> FEATURE:
<221> NAME/KEY: MISC_FEATURE
<222> LOCATION: (21)..(21)
<223> OTHER INFORMATION: X = any amino acid
<220> FEATURE:
<221> NAME/KEY: MISC_FEATURE
<222> LOCATION: (23)..(23)
<223> OTHER INFORMATION: X = any amino acid
<220> FEATURE:
<221> NAME/KEY: MISC_FEATURE
<222> LOCATION: (25)..(25)
<223> OTHER INFORMATION: X = S or T
<220> FEATURE:
<221> NAME/KEY: MISC_FEATURE
<222> LOCATION: (26)..(27)
<223> OTHER INFORMATION: X = any amino acid or no amino acid
<220> FEATURE:
<221> NAME/KEY: MISC_FEATURE
<222> LOCATION: (29)..(30)
<223> OTHER INFORMATION: X = any amino acid
<220> FEATURE:
<221> NAME/KEY: MISC_FEATURE
<222> LOCATION: (31)..(31)
<223> OTHER INFORMATION: X = A or G
<220> FEATURE:
<221> NAME/KEY: MISC_FEATURE
<222> LOCATION: (32)..(37)
<223> OTHER INFORMATION: X = any amino acid
<220> FEATURE:
<221> NAME/KEY: MISC_FEATURE
<222> LOCATION: (38)..(39)
<223> OTHER INFORMATION: X = F or Y
<220> FEATURE:
<221> NAME/KEY: MISC_FEATURE
<222> LOCATION: (40)..(40)
<223> OTHER INFORMATION: X = any amino acid

<400> SEQUENCE: 11

Phe Val Arg His Xaa Phe Asn Arg Xaa Gly Xaa Xaa Gly Xaa Xaa Xaa
1               5                   10                  15

Pro Xaa Asp Leu Xaa Ile Xaa Gly Xaa Xaa Xaa Gly Xaa Xaa Xaa Xaa
            20                  25                  30

Xaa Xaa Xaa Xaa Xaa Xaa Xaa Xaa Thr
        35                  40

<210> SEQ ID NO 12
<211> LENGTH: 8
<212> TYPE: PRT
<213> ORGANISM: artificial sequence
<220> FEATURE:
<223> OTHER INFORMATION: synthetic peptide

<400> SEQUENCE: 12

Trp Ser His Pro Gln Phe Glu Lys
1               5

<210> SEQ ID NO 13
<211> LENGTH: 19
<212> TYPE: RNA
<213> ORGANISM: artificial sequence
<220> FEATURE:
<223> OTHER INFORMATION: synthetic oligonucleotide
```

```
<400> SEQUENCE: 13
uacaacaaac cguugugug                                                    19

<210> SEQ ID NO 14
<211> LENGTH: 19
<212> TYPE: RNA
<213> ORGANISM: artificial sequence
<220> FEATURE:
<223> OTHER INFORMATION: synthetic oligonucleotide

<400> SEQUENCE: 14
cuaacuaaca cuggguuau                                                    19

<210> SEQ ID NO 15
<211> LENGTH: 21
<212> TYPE: RNA
<213> ORGANISM: artificial sequence
<220> FEATURE:
<223> OTHER INFORMATION: synthetic oligonucleotide
<220> FEATURE:
<221> NAME/KEY: misc_feature
<222> LOCATION: (20)..(21)
<223> OTHER INFORMATION: n = t

<400> SEQUENCE: 15
gagguauaug acuuugcuun n                                                 21

<210> SEQ ID NO 16
<211> LENGTH: 21
<212> TYPE: RNA
<213> ORGANISM: artificial sequence
<220> FEATURE:
<223> OTHER INFORMATION: synthetic oligonucleotide
<220> FEATURE:
<221> NAME/KEY: misc_feature
<222> LOCATION: (1)..(2)
<223> OTHER INFORMATION: n = t

<400> SEQUENCE: 16
nncuccauau acugaaacga a                                                 21

<210> SEQ ID NO 17
<211> LENGTH: 21
<212> TYPE: RNA
<213> ORGANISM: artificial sequence
<220> FEATURE:
<223> OTHER INFORMATION: synthetic oligonucleotide
<220> FEATURE:
<221> NAME/KEY: misc_feature
<222> LOCATION: (20)..(21)
<223> OTHER INFORMATION: n = t

<400> SEQUENCE: 17
aggaggauga aauagauggn n                                                 21

<210> SEQ ID NO 18
<211> LENGTH: 21
<212> TYPE: RNA
<213> ORGANISM: artificial sequence
<220> FEATURE:
<223> OTHER INFORMATION: synthetic oligonucleotide
<220> FEATURE:
<221> NAME/KEY: misc_feature
<222> LOCATION: (1)..(2)
<223> OTHER INFORMATION: n = t

<400> SEQUENCE: 18
nnuccuccua cuuuaucuac c                                                 21
```

<210> SEQ ID NO 19
<211> LENGTH: 47
<212> TYPE: DNA
<213> ORGANISM: artificial sequence
<220> FEATURE:
<223> OTHER INFORMATION: synthetic oligonucleotide

<400> SEQUENCE: 19
caccagagtt caaaagccct tcatcgaaat gaagggcttt tgaactc        47

<210> SEQ ID NO 20
<211> LENGTH: 47
<212> TYPE: DNA
<213> ORGANISM: artificial sequence
<220> FEATURE:
<223> OTHER INFORMATION: synthetic oligonucleotide

<400> SEQUENCE: 20
aaaaagagtt caaaagccct tcatttcgat gaagggcttt tgaactc        47

<210> SEQ ID NO 21
<211> LENGTH: 47
<212> TYPE: DNA
<213> ORGANISM: artificial sequence
<220> FEATURE:
<223> OTHER INFORMATION: synthetic oligonucleotide

<400> SEQUENCE: 21
caccgctaca caaatcagcg atttcgaaaa atcgctgatt tgtgtag        47

<210> SEQ ID NO 22
<211> LENGTH: 47
<212> TYPE: DNA
<213> ORGANISM: artificial sequence
<220> FEATURE:
<223> OTHER INFORMATION: synthetic oligonucleotide

<400> SEQUENCE: 22
aaaactacac aaatcagcga tttttcgaaa tcgctgattt gtgtagc        47

<210> SEQ ID NO 23
<211> LENGTH: 49
<212> TYPE: DNA
<213> ORGANISM: artificial sequence
<220> FEATURE:
<223> OTHER INFORMATION: synthetic oligonucleotide

<400> SEQUENCE: 23
caccaggagg atgaaataga tggttcgaaa accatctatt tcatcctcc        49

<210> SEQ ID NO 24
<211> LENGTH: 49
<212> TYPE: DNA
<213> ORGANISM: artificial sequence
<220> FEATURE:
<223> OTHER INFORMATION: synthetic oligonucleotide

<400> SEQUENCE: 24
aaaaggagga tgaaatagat ggttttcgaa ccatctattt catcctcct        49

<210> SEQ ID NO 25
<211> LENGTH: 50
<212> TYPE: DNA
<213> ORGANISM: artificial sequence
<220> FEATURE:

<223> OTHER INFORMATION: synthetic oligonucleotide

<400> SEQUENCE: 25
caccgcccat tacaatattg taacccgaag gttacaatat tgtaatgggc    50

<210> SEQ ID NO 26
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 26
aaaagcccat tacaatattg taaccttcgg gttacaatat tgtaatgggc    50

<210> SEQ ID NO 27
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 27
caacgaggta tatgactttg cttttcgaaa aaagcaaagt catatacctc    50

<210> SEQ ID NO 28
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 28
aaaagaggta tatgactttg cttttttcga aaagcaaagt catatacctc    50

<210> SEQ ID NO 29
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 29
caccggtcga tgtatgtctt gttgccgaag caacaagaca tacatcgacc    50

<210> SEQ ID NO 30
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 30
aaaaggtcga tgtatgtctt cttgcttcgg caacaagaca tacatcgacc    50

<210> SEQ ID NO 31
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 31
caccaaaaga gaactgcaat gt    22

```
<210> SEQ ID NO 32
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 32
ttgctgttct aatgttgttc ca                                         22

<210> SEQ ID NO 33
<211> LENGTH: 23
<212> TYPE: DNA
<213> ORGANISM: artificial sequence
<220> FEATURE:
<223> OTHER INFORMATION: synthetic oligonucleotide

<400> SEQUENCE: 33
ggagatacac ctacattgca tga                                        23

<210> SEQ ID NO 34
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 34
ggggcacaca attcctagtg                                            20

<210> SEQ ID NO 35
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 35
acagtccatg ccatcactgc c                                          21

<210> SEQ ID NO 36
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 36
gcctgcttca ccaccttctt g                                          21

<210> SEQ ID NO 37
<211> LENGTH: 31
<212> TYPE: DNA
<213> ORGANISM: artificial sequence
<220> FEATURE:
<223> OTHER INFORMATION: synthetic oligonucleotide

<400> SEQUENCE: 37
ggatcccacc atgagcctgt ggagacccag c                               31

<210> SEQ ID NO 38
<211> LENGTH: 33
<212> TYPE: DNA
<213> ORGANISM: artificial sequence
<220> FEATURE:
<223> OTHER INFORMATION: synthetic oligonucleotide
```

```
<400> SEQUENCE: 38
ggaagcttat gtggtggtgc tggcgctggg ggc                              33

<210> SEQ ID NO 39
<211> LENGTH: 34
<212> TYPE: DNA
<213> ORGANISM: artificial sequence
<220> FEATURE:
<223> OTHER INFORMATION: synthetic oligonucleotide

<400> SEQUENCE: 39
gcaagcttag gcctgcagca ggaactttct gccc                             34

<210> SEQ ID NO 40
<211> LENGTH: 30
<212> TYPE: DNA
<213> ORGANISM: artificial sequence
<220> FEATURE:
<223> OTHER INFORMATION: synthetic oligonucleotide

<400> SEQUENCE: 40
ccgctagcca ccatgagcct gtggagaccc                                  30

<210> SEQ ID NO 41
<211> LENGTH: 39
<212> TYPE: DNA
<213> ORGANISM: artificial sequence
<220> FEATURE:
<223> OTHER INFORMATION: synthetic oligonucleotide

<400> SEQUENCE: 41
ctctctgctg gcggggtcgt tgaagaagtg ccgcacgaa                        39

<210> SEQ ID NO 42
<211> LENGTH: 30
<212> TYPE: DNA
<213> ORGANISM: artificial sequence
<220> FEATURE:
<223> OTHER INFORMATION: synthetic oligonucleotide

<400> SEQUENCE: 42
cggaattcta tcacttcttg gttttcttcc                                  30

<210> SEQ ID NO 43
<211> LENGTH: 39
<212> TYPE: DNA
<213> ORGANISM: artificial sequence
<220> FEATURE:
<223> OTHER INFORMATION: synthetic oligonucleotide

<400> SEQUENCE: 43
gaccccgcca gcagagagag aagcggcacc gtgggcgag                        39

<210> SEQ ID NO 44
<211> LENGTH: 9
<212> TYPE: PRT
<213> ORGANISM: artificial sequence
<220> FEATURE:
<223> OTHER INFORMATION: synthetic peptide

<400> SEQUENCE: 44

Ser Val Pro Thr Asp Leu Tyr Ile Lys
1               5

<210> SEQ ID NO 45
```

```
<211> LENGTH: 10
<212> TYPE: PRT
<213> ORGANISM: artificial sequence
<220> FEATURE:
<223> OTHER INFORMATION: synthetic peptide

<400> SEQUENCE: 45

Arg His Phe Phe Asn Arg Ser Gly Thr Val
1               5                   10

<210> SEQ ID NO 46
<211> LENGTH: 5
<212> TYPE: PRT
<213> ORGANISM: artificial sequence
<220> FEATURE:
<223> OTHER INFORMATION: synthetic peptide

<400> SEQUENCE: 46

Asp Leu Ile Tyr Lys
1               5

<210> SEQ ID NO 47
<211> LENGTH: 8
<212> TYPE: PRT
<213> ORGANISM: artificial sequence
<220> FEATURE:
<223> OTHER INFORMATION: synthetic peptide

<400> SEQUENCE: 47

Arg His Phe Phe Asn Arg Ser Gly
1               5

<210> SEQ ID NO 48
<211> LENGTH: 9
<212> TYPE: PRT
<213> ORGANISM: artificial sequence
<220> FEATURE:
<223> OTHER INFORMATION: synthetic peptide

<400> SEQUENCE: 48

Ser Gly Thr Val Gly Glu Ser Val Pro
1               5

<210> SEQ ID NO 49
<211> LENGTH: 6
<212> TYPE: PRT
<213> ORGANISM: artificial sequence
<220> FEATURE:
<223> OTHER INFORMATION: synthetic peptide

<400> SEQUENCE: 49

Arg Ser Gly Thr Val Gly
1               5

<210> SEQ ID NO 50
<211> LENGTH: 9
<212> TYPE: PRT
<213> ORGANISM: artificial sequence
<220> FEATURE:
<223> OTHER INFORMATION: synthetic peptide

<400> SEQUENCE: 50

Arg Ser Gly Thr Val Gly Glu Ser Val
1               5

<210> SEQ ID NO 51
<211> LENGTH: 31
```

<210> SEQ ID NO 51
<211> LENGTH: 31
<212> TYPE: DNA
<213> ORGANISM: artificial sequence
<220> FEATURE:
<223> OTHER INFORMATION: synthetic oligonucleotide

<400> SEQUENCE: 51
ggatcccacc atgagcctgt ggagacccag c        31

<210> SEQ ID NO 52
<211> LENGTH: 31
<212> TYPE: DNA
<213> ORGANISM: artificial sequence
<220> FEATURE:
<223> OTHER INFORMATION: synthetic oligonucleotide

<400> SEQUENCE: 52
aagctttcac ttcttggttt tcttccgctt g        31

<210> SEQ ID NO 53
<211> LENGTH: 49
<212> TYPE: DNA
<213> ORGANISM: artificial sequence
<220> FEATURE:
<223> OTHER INFORMATION: synthetic oligonucleotide

<400> SEQUENCE: 53
cttctcgaac tggggtggc tccagttctc ggtgtcgtcc agcttgttc        49

<210> SEQ ID NO 54
<211> LENGTH: 48
<212> TYPE: DNA
<213> ORGANISM: ARTIFICIAL SEQUENCE
<220> FEATURE:
<223> OTHER INFORMATION: synthetic oligonucleotide

<400> SEQUENCE: 54
tggagccacc cccagttcga aaggccagc gcctacgccg ccaacgcc        48

<210> SEQ ID NO 55
<211> LENGTH: 31
<212> TYPE: DNA
<213> ORGANISM: artificial sequence
<220> FEATURE:
<223> OTHER INFORMATION: synthetic oligonucleotide

<400> SEQUENCE: 55
aagctttcac ttcttggttt tcttccgctt g        31

<210> SEQ ID NO 56
<211> LENGTH: 31
<212> TYPE: DNA
<213> ORGANISM: artificial sequence
<220> FEATURE:
<223> OTHER INFORMATION: synthetic oligonucleotide

<400> SEQUENCE: 56
ggatcccacc atgagcctgt ggagacccag c        31

<210> SEQ ID NO 57
<211> LENGTH: 44
<212> TYPE: DNA
<213> ORGANISM: artificial sequence
<220> FEATURE:
<223> OTHER INFORMATION: synthetic oligonucleotide

<400> SEQUENCE: 57
cgggtctaga gaattctcga gagggcctcc ggcgtatctg ttgc    44

<210> SEQ ID NO 58
<211> LENGTH: 42
<212> TYPE: DNA
<213> ORGANISM: artificial sequence
<220> FEATURE:
<223> OTHER INFORMATION: synthetic peptide

<400> SEQUENCE: 58
ctcgagaatt ctctagaccc gggcaccgat aacagggagt gc    42

<210> SEQ ID NO 59
<211> LENGTH: 27
<212> TYPE: DNA
<213> ORGANISM: artificial sequence
<220> FEATURE:
<223> OTHER INFORMATION: synthetic oligonucleotide

<400> SEQUENCE: 59
cccgggggcc agggtgtcgg tggcggt    27

<210> SEQ ID NO 60
<211> LENGTH: 30
<212> TYPE: DNA
<213> ORGANISM: artificial sequence
<220> FEATURE:
<223> OTHER INFORMATION: synthetic oligonucleotide

<400> SEQUENCE: 60
ctcgaggcca gcgccaccca gctgtacaag    30

<210> SEQ ID NO 61
<211> LENGTH: 31
<212> TYPE: DNA
<213> ORGANISM: artificial sequence
<220> FEATURE:
<223> OTHER INFORMATION: synthetic oligonucleotide

<400> SEQUENCE: 61
gtcgaccatg tagtagctgg ggtgcaggat g    31

<210> SEQ ID NO 62
<211> LENGTH: 35
<212> TYPE: DNA
<213> ORGANISM: artificial sequence
<220> FEATURE:
<223> OTHER INFORMATION: synthetic oligonucleotide

<400> SEQUENCE: 62
ccggatccgc caccatggcc agcgccaccc agctg    35

<210> SEQ ID NO 63
<211> LENGTH: 39
<212> TYPE: DNA
<213> ORGANISM: artificial sequence
<220> FEATURE:
<223> OTHER INFORMATION: synthetic oligonucleotide

<400> SEQUENCE: 63
ccctctagag ccaccatggc cagcgccacc cagctgtac    39

<210> SEQ ID NO 64
<211> LENGTH: 37
<212> TYPE: DNA
<213> ORGANISM: artificial sequence -continued

```
<220> FEATURE:
<223> OTHER INFORMATION: synthetic oligonucleotide

<400> SEQUENCE: 64
gcggccgcta tcacaggatg tagtagctgg ggtgcag                            37

<210> SEQ ID NO 65
<211> LENGTH: 6
<212> TYPE: PRT
<213> ORGANISM: artificial sequence
<220> FEATURE:
<223> OTHER INFORMATION: synthetic peptide

<400> SEQUENCE: 65

Asp Pro Ala Ser Arg Glu
1               5
```